US009775730B1

(12) United States Patent
Walzman

(10) Patent No.: US 9,775,730 B1
(45) Date of Patent: Oct. 3, 2017

(54) FLOW-DIVERTING COVERED STENT

(71) Applicant: Walzman Innovations, LLC, Boynton Beach, FL (US)

(72) Inventor: Daniel Walzman, Bergenfield, NJ (US)

(*) Notice: Subject to any disclaimer, the term of this patent is extended or adjusted under 35 U.S.C. 154(b) by 0 days.

(21) Appl. No.: 15/341,820

(22) Filed: Nov. 2, 2016

(51) Int. Cl.
*A61F 2/06* (2013.01)
*A61F 2/86* (2013.01)
*A61F 2/958* (2013.01)

(52) U.S. Cl.
CPC ........ *A61F 2/86* (2013.01); *A61F 2/06* (2013.01); *A61F 2/958* (2013.01); *A61F 2002/068* (2013.01); *A61F 2002/9583* (2013.01); *A61F 2210/0071* (2013.01)

(58) Field of Classification Search
CPC .......... A61F 2/82; A61F 2002/821; A61F 2002/823; A61F 2002/825; A61F 2002/826; A61F 2/856; A61F 2/86; A61F 2/88; A61F 2/885; A61F 2/89; A61F 2/90; A61F 2/91; A61F 2/915; A61F 2/91508; A61F 2/91516; A61F 2/91525; A61F 2/91533; A61F 2/848; A61F 2002/8483; A61F 2002/8486; A61F 2002/91541; A61F 2002/9155; A61F 2002/91558; A61F 2002/91566; A61F 2002/91575; A61F 2002/91583; A61F 2002/91591; A61F 2/07; A61F 2002/072; A61F 2002/075; A61F 2002/077
See application file for complete search history.

(56) References Cited

U.S. PATENT DOCUMENTS

2013/0245745 A1* 9/2013 Vong .............. A61F 2/885
623/1.12

OTHER PUBLICATIONS

Merriam-Webster definition for "sheet" as accessed Jan. 4, 2017; https://www.merriam-webster.com/dictionary/sheet.*
Bonneville F., et al., "Intracranial aneurysms: an overview", Neuroimag Clin N Am, 2006, vol. 16, pp. 371-382.
Phillips L.H., et al., "The unchanging pattern of subarachnoid hemorrhage in a community", Neurology, 1980, vol. 30, pp. 1034-1040.
Seibert B., et al., "Intracranial aneurysms: review of current treatment options and outcomes", Frontiers in Neurology, 2011, vol. 2, pp. 1-11.
Stehbens W.E., et al., "Early berry aneurysm formation in marfan's syndrome", Surg. Neurol. 1989, vol. 31, pp. 200-2002.
Stehbens W.E., "Pathology and pathogenesis of intracranial berry aneurysms", Neurological Research, 1990, vol. 12, pp. 29-33.
Thanvi B., et al., "Carotid and verbal artery dissection syndromes" Postgrad Med J, 2005, vol. 81, pp. 383-388.
(Continued)

*Primary Examiner* — Jonathan Miles

(57) ABSTRACT

The described invention provides an endovascular stent device comprising a tubular structure comprising a circumference; wherein a flow-diverting portion of the circumference is covered by a flow-diverting material; a length (l) from a proximal end to a distal end; and an inner diameter (d); wherein the flow-diverting portion of the circumference comprises a length (l'); and the flow-diverting portion of the circumference covers at least 1% to at least 100% of the endovascular stent device. According to some embodiments, the flow-diverting material is adapted to increase blood vessel wall adherence and minimize risk of an endoleak.

22 Claims, 9 Drawing Sheets

(56) References Cited

OTHER PUBLICATIONS

Yong-Zhong G., et al., " Pathogenesis and histopathology of saccular aneurysms: review of the literature", Neurological Research, 1990, vol. 12, pp. 249-253.
Stiebel-Kalish H., et al., "Presentation, natural history, and management of carotid cavernous aneurysms", Neurosurgery, 2005, vol. 57, pp. 850-857.
Tanweer O., et al., "Cavernous carotid aneurysms in the eral of flow diversion: A need to revisit treatment paradigms", AJNR Am J. Neuroradiol, 2014, vol. 35, pp. 2334-2340.
Tsutsumi K., et al., "Risk of aneurysm recurrence in patients with clipped cerebral aneurysms: Results of long-term follow-up angiography", Stroke, 2001, vol. 32, pp. 1191-1194.
Van Gijn J., et al., "Subarachnoid haemorrhage", Lancet, 2007, vol. 369, pp. 306-318.
Wagner M., et al., "Unruptured intracrannial aneurysms: Using evidence and outcomes to guide patient teaching", Crit Care Nurs Q, 2005, vol. 28, pp. 341-344.
Wiebers D.O., " Unruptured intracranial aneurysms: natural history, clinical outcome, and risks of surgical and endovascular treatment", Lancet, 2003, vol. 362, pp. 103-110.
Yurt A., et al., "Biomarkers of connective tissue disease in patients with intracranial aneurysms", Journal of Clinical Neuroscience, 2010, vol. 17, pp. 1119-1121.
Al-Yamany B., et al., "Giant fusiform aneurysm of the middle cerebral artery: successful hunterian ligation with out distal bypass", British Journal of Neurosurgery, 1998, vol. 12, pp. 572-575.
Alvarez-Tostado J.A., et al., "The brachial artery: A critical access for endovascular procedures", Peripheral Vascular Surgery Society, J Vasc Surg, 2009, vol. 49, pp. 378-385.
Anson, J.A., et al., "Characteristics and surgical treatment of dolichoectatic and fusiform aneurysms", J. Neurosurg, 1996, vol. 84, pp. 185-193.
Austin G., et al., "The significance of the extracellular matrix in intracranial aneurysms", Annals of Clinical and Laboratory Science, 1993, vol. 23, pp. 97-105, Institute for Clinical Science, Inc.
Bassetti C., et al., "Recurrence of cervical artery dissection", Stroke, 1996, vol. 27, pp. 1804-1807.
Bhatia K.D., et al., "Sucessful treatment of six cases of indirect carotid-cavernous fistula with ethylene vinyl alcohol copoymer (Onyx) transvenous embolization", J. Neuro-Opthalmol, 2009, vol. 29, pp. 1-8.
Campi A., et al., "Retreatment of ruptured cerebral aneurysms in patients randomized by coiling or clipping in the International subarachnoid aneurysm trial (ISAT)" Stroke, 2007, vol. 38, pp. 1538-1544.
Ceylan S., et al., "Reconstruction of the middle cerebral artery after excision of a giant fusiform aneurysm", Neurosurg. Rev., 1998, vol. 21, p. 189-193.
Corr P., et al., "Endocarditis-related cerebral aneurysms: Radiologic changes with treatment", AJNR Am J Neuroradiol, 1995, vol. 16; pp. 745-748.
Cousins T.R., et al., "Arterial cannulation: A critical review", AANA Journal, 2004, vol. 72, pp. 267-271.
Day A.L., et al., "Spontaneous fusiform middle cerebral artery aneurysms: characteristics and a proposed mechanism of formation", J Neurosurg, 2003, pp. 228-240.
Drake C.G., et al., "Giant fusiform intracranial aneurysms: review of 120 patients treated surgically from 1965-1992", J. Neurosurg, 1997, vol. 87, pp. 141-162.
Ducruet A.F., et al., "Intracranial infectious aneurysms: a comprehensive review", Neurosurg Rev, 2010, vol. 33, pp. 37-46.
Eddleman C.S., et al., "Cavernous carotid aneurysms: to treat or not to treat", Neurosurg Focus, 2009, vol. 26, pp. 1-10.
Findlay J.M., et al., "Non-atherosclerosis fusiform cerebral aneurysms", Can. J. Neurol. Sci. 2002, vol. 29, pp. 41-48.
Gasparotti R., et al., "Intracranial aneurysms", Eur Radio, 2005, vol. 15, pp. 441-447.

Giroud M., et al., "Incidence of internal carotid artery dissection in the community of dijon", J Neurol Neurosurg Psychiatry, 1994, vol. 57, p. 1443.
Gobin Y.P., et al., "In vitro study of haemodynamics in a giant saccular aneurysm model: influence of flow dynamics in the parent vessel and effects of coil embolisation", Neuroradiology, 1994, vol. 36, pp. 530-536.
Gonzalez N., et al., "Treatment of unruptured aneurysms with GDCs: Clinical experience with 247 aneurysms", AJNR Am J Neuroradiol, 2004, vol. 25, pp. 577-583.
Hademenos G.J., et al., "Biophysical mechanisms of stroke", Stroke, 1997, vol. 28, pp. 2067-2077.
Hademenos G.J., et al., "The physics of cerebral aneurysms", Physics Today, 1995, pp. 24-30.
Hart R.G., et al., "Hematologic disorders and ischemic stroke", Stroke, 1990, vol. 21, pp. 1111-1121.
Hurst R.W., et al., "Myocotic aneurysm and cerebral infarction resulting from fungal sinustis: Imaging and pathologic correlation", AJNR Am J Neuroradiol, 2001, vol. 22, pp. 858-863.
Kanaan H., et al., "In-stent thrombosis and stenosis afer neck-remodeling device-assisted coil embolization of intracranial aneurysms", Neurosurgery, 2010, vol. 67, pp. 1523-1533.
Karaman E., et al., "Carotid-cavernous fistula after functional endoscopic sinus surgery", The Journal of Craniofacial Surgery, 2009, vol. 20, pp. 556-558.
Keedy A., "An overview of intracrannial aneurysms", MJM, 2006, vol. 9, pp. 141-146.
Kondo S., et al., "Cerebral aneurysms arising at nonbranching sites", Stroke, 1997, vol. 28, pp. 398-404.
Krex D., et al., "Genesis of cerebral aneurysms—An update", Acta Neurochair (Wien), 2001, vol. 143: pp. 429-449.
Kulcsar Z., et al., "Intra-Aneurysmal thrombosis as a possible cause fo delayed aneurysms rupture after flow-diversion treatment", AJNR Am J Neuroradiol, 2011, vol. 32, pp. 20-25.
Kuppersmith M.J., et al., "Cavernous carotid aneurysms rarely cause subarachnoid hemorrhage or major neurologic morbidity", Journal of Stroke and Cerebrovascular Diseases, 2002, vol. 11, pp. 9-14.
Lee W-K, et al., "Infected (Myocotic) aneurysms: Spectrum of imaging appearances and managment", Radiographics, 2008, vol. 28, pp. 1853-1868.
Lubicz B., et al., "Flow-diverter stent for the endovascular treatment of intracranial aneurysms": A study in 29 patients with 34 aneurysms, Stroke, 2010, vol. 41: 2247-2253.
Mason A.M., et al., "Surgical managment of intracranial aneurysms in the endovascular era: Review article", J Korean Neurosurg Soc, 2009, vol. 45, pp. 133-142.
Masuda H., et al., "Adaptive remodeling of internal elastic lamina and endothelial dining during flow-induced arterial enlargement", Arterioscler Thromb Vasc Biol., 1999, vol. 19, pp. 2298-2307.
Meng H., et al., "Complex hemodynamics at the apex of an arterial bifurcation induces vascular remodeling resembling cerebral aneurysm initiation", Stroke, 2007, vol. 38, pp. 1924-1931.
Minnerup J., et al., "Development of a mycotic aneurysm within 4 days", Neurology, 2008, vol. 71, p. 1745.
Mocco J, et al., "Treatment of intracranial aneurysms with the enterprise stent: a multicenter registry", J Neurosurg, 2009, vol. 110, pp. 35-39.
Murayama Y., et al., "Gugliemi detachable coil embolization of cerebral aneurysms: 11 years' experience", J. Neurosurg, 2003, vol. 98, pp. 959-966.
Nakayama Y., et al., "Giant fusiform aneurysm of the basilar artery: Consideration of its pathogenesis", Surg Neurol, 1999, vol. 51, pp. 140-145.
Ong C.K., et al., "Onyx embolisation of cavernous sinus dural arteriovenous fistula via direct percutaneous transorbital puncture", Journal of Medical Imaging and Radiation Oncology, 2009, vol. 53, pp. 291-295.
Otawara Y., et al., "Dissecting aneurysms of the anterior cerebral artery and accessory middle cerebral artery. Case Report", Neurosurg. Rev., 1997, vol. 20, pp. 145-148.

(56) References Cited

OTHER PUBLICATIONS

Park K-W, et al., "Vertebral artery dissection: Natural History, Clinical Features and Therapeutic Considerations", J Korean Neurosurg Soc, 2008, vol. 44, pp. 109-115.

Peters P.J., et al., "A dangerous dilemma: managment of infectious intracranial aneurysms complicating endocarditis", Lancet Infect Dis, 2006, vol. 6, pp. 742-748.

Schievink W.I., et al., "Coexistence of fibromuscular dysplasia and cystic medial necrosis in a patient with marfan's syndrome and bilateral carotid artery dissections", Stroke, 1994, vol. 25, pp. 2492-2496.

Schievink W.I., et al., "Neurovascular manifestations of heritable connective tissue disorders: A review", Stroke, 1994, vol. 25, pp. 889-903.

Schievink W.I., et al., "Recurrent spontaneous cervical-artery dissection", The New England Journal of Medicine, 1994, vol. 330, pp. 393-397.

Schievink W.I., et al., "Spontaneous dissection of the carotid and vertebral arteries", The New England Journal of Medicine, 2001, vol. 344, pp. 898-905.

Schievink W.I., et al., "The treatment of spontaneous carotid and vertebral artery dissections", Current Opinions in Cardiology, 2000, vol. 15, pp. 316-321.

Selviaridis P., et al., "Fusiform aneurysm of the posterior cerebral artery: Report of two cases", Acta Neurochir (Wien), 2002, vol. 144, pp. 295-299.

Shojima M., et al., "Magnitude and role of wall shear stress on cerebral aneurysm", Stroke, 2004, vol. 35, pp. 2500-2505.

Horten B.C., et al., "Fungal aneurysms of intracranial vessels", Arch Neurol, 1976, vol. 33, pp. 577-579.

\* cited by examiner

FLOW-DIVERTING COVERED STENT

FIELD OF THE INVENTION

The described invention relates generally to endovascular devices.

BACKGROUND OF THE INVENTION

Blood Vessel Structure and Function

Blood vessels are dynamic structures that constrict, relax, pulsate, and proliferate. Within the body, blood vessels form a closed delivery system that begins and ends at the heart. There are three major types of blood vessels: (i) arteries; (ii) capillaries and (iii) veins. As the heart contracts, it forces blood into the large arteries leaving the ventricles. Blood then moves into smaller arteries successively, until finally reaching the smallest branches, the arterioles, which feed into the capillary beds of organs and tissues. Blood drains from the capillaries into venules, the smallest veins, and then into larger veins that merge and ultimately empty into the heart.

Arteries carry blood away from the heart and "branch" as they form smaller and smaller divisions. Arterial walls consist of three layers: an intima (innermost layer); a media (middle muscular layer); and an adventitia (outermost layer) (Park K-W et al. J. Korean Neurosurg. Soc. 2008; 44(3): 109-115). In contrast, veins carry blood toward the heart and "merge" into larger and larger vessels approaching the heart. In the systemic circulation, arteries carry oxygenated blood and veins carry oxygen-poor blood. In the pulmonary circulation, the opposite is true. The arteries (still defined as the vessels leading away from the heart), carry oxygen-poor blood to the lungs, and the veins carry oxygen-rich blood from the lungs to the heart.

The only blood vessels that have intimate contact with tissue cells in the human body are capillaries. In this way, capillaries help serve cellular needs. Exchanges between the blood and tissue cells occur primarily through the thin capillary walls.

The walls of most blood vessels (the exception being the smallest vessels, e.g., venules), have three layers, or tunics, that surround a central blood-containing space called the vessel lumen.

The innermost tunic (layer) is the tunica intima. The tunica intima contains the endothelium, the simple squamous epithelium that lines the lumen of all vessels. The endothelium is continuous with the endocardial lining of the heart, and its flat cells fit closely together, forming a slippery surface that minimizes friction so blood moves smoothly through the lumen. In vessels larger than 1 mm in diameter, a sub-endothelial layer, consisting of a basement membrane and loose connective tissue, supports the endothelium.

The middle tunic (layer), the tunica media, contains mostly circularly arranged smooth muscle cells and sheets of elastin. The activity of the smooth muscle is regulated by sympathetic vasomotor nerve fibers of the autonomic nervous system. Depending on the body's needs at any given time, regulation causes either vasoconstriction (lumen diameter decreases) or vasodilation (lumen diameter increases). The activities of the tunica media are critical in regulating the circulatory system, because small changes in vessel diameter greatly influence blood flow and blood pressure. Generally, the tunica media is the bulkiest layer in arteries, which bear the chief responsibility for maintaining blood pressure and proper circulation.

The outer layer of a blood vessel wall, the tunica externa, is primarily composed of collagen fibers that protect, reinforce and anchor the vessel to surrounding structures. The tunica externa contains nerve fibers, lymphatic vessels, and elastic fibers (e.g., in large veins). In large vessels, the tunica externa contains a structure known as the vasa vasorum, which literally means "vessels of vessels". The vasa vasorum nourishes external tissues of the blood vessel wall. Interior layers of blood vessels receive nutrients directly from blood in the lumen (See, e.g., The Cardiovascular System at a Glance, 4$^{th}$ Edition, Philip I. Aaronson, Jeremy P. T. Ward, Michelle J. Connolly, November 2012, © 2012, Wiley-Blackwell, Hoboken, N.J.).

Brain Circulation/Cerebral Arteries

FIGS. 1 and 2 are schematic illustrations of the brain's blood vessels. Each cerebral hemisphere is supplied by an internal carotid artery, which arises from a common carotid artery beneath the angle of the jaw, enters the cranium through the carotid foramen, traverses the cavernosus sinus (giving off the ophthalmic artery), penetrates the dura and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it also gives off the anterior choroidal artery, which supplies the anterior hippocampus and, at a caudal level, the posterior limb of the internal capsule. Each vertebral artery arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, pp. 854-56 (1985)).

Interconnections between blood vessels (anastomoses) protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 85¬56 (1985)).

The circle of Willis at the base of the brain is the principal arterial anastomotic trunk of the brain. Blood reaches it mainly via the vertebral and internal carotid arteries. Anastomoses (interconnections between blood vessels) occur between arterial branches of the circle of Willis over the cerebral hemispheres and via extracranial arteries that penetrate the skull through various foramina.

The circle of Willis is formed by anastamoses between the internal carotid, basilar, anterior cerebral, anterior communicating, posterior cerebral, and posterior communicating arteries. The internal carotid artery terminates in the anterior cerebral and middle cerebral arteries. Near its termination, the internal carotid artery gives rise to the posterior communicating artery, which joins caudally with the posterior cerebral artery. The anterior cerebral arteries connect via the anterior communicating artery.

The lateral surface of each cerebral hemisphere is supplied mainly by the middle cerebral artery. The medial and inferior surfaces of the cerebral hemispheres are supplied by the anterior cerebral and posterior cerebral arteries.

The middle cerebral artery, a terminal branch of the internal carotid artery, enters the lateral cerebral fissure and divides into cortical branches that supply the adjacent frontal, temporal, parietal and occipital lobes. Small penetrating arteries, the lenticulostriate arteries, arise from the basal portion of the middle cerebral artery to supply the internal capsule and adjacent structures.

The anterior cerebral artery extends medially from its origin from the internal carotid artery into the longitudinal cerebral fissure to the genu of the corpus callosum, where it turns posteriorly close to the corpus callosum. It gives branches to the medial frontal and parietal lobes and to the adjacent cortex along the medial surface of these lobes.

The posterior cerebral artery arises from the basilar artery at its rostral end usually at the level of the midbrain, curves dorsally around the cerebral peduncle, and sends branches to the medial and inferior surfaces of the temporal lobe and to the medial occipital lobe. Branches include the calcarine artery and perforating branches to the posterior thalamus and subthalamus.

The basilar artery is formed by the junction of the vertebral arteries. It supplies the upper brain stem via short paramedian, short circumferential, and long circumferential branches.

The midbrain is supplied by the basilar, posterior cerebral, and superior cerebellar arteries. The pons is supplied by the basilar, anterior cerebellar, inferior cerebellar, and superior cerebellar arteries. The medulla oblongata is supplied by the vertebral, anterior spinal, posterior spinal, posterior inferior cerebellar, and basilar arteries. The cerebellum is supplied by the cerebellar arteries (superior cerebellar, anterior inferior cerebellar, and posterior inferior cerebellar arteries).

The choroid plexuses of the third and lateral ventricles are supplied by branches of the internal carotid and posterior cerebral arteries. The choroid plexus of the fourth ventricle is supplied by the posterior inferior cerebellar arteries.

Femoral Artery

The femoral artery is the main artery that provides oxygenated blood to the tissues of the leg. It passes through the deep tissues of the femoral (or thigh) region of the leg parallel to the femur.

The common femoral artery is the largest artery found in the femoral (thigh) region of the body. It begins as a continuation of the external iliac artery at the inguinal ligament which serves as the dividing line between the pelvis and the leg. From the inguinal ligament, the femoral artery follows the medial side of the head and neck of the femur inferiorly and laterally before splitting into the deep femoral artery and the superficial femoral artery.

The superficial femoral artery flexes to follow the femur inferiorly and medially. At its distal end, it flexes again and descends posterior to the femur before forming the popliteal artery of the posterior knee and continuing on into the lower leg and foot. Several smaller arteries branch off from the superficial femoral artery to provide blood to the skin and superficial muscles of the thigh.

The deep femoral artery follows the same path as the superficial branch, but follows a deeper path through the tissues of the thigh, closer to the femur. It branches off into the lateral and medial circumflex arteries and the perforating arteries that wrap around the femur and deliver blood to the femur and deep muscles of the thigh. Unlike the superficial femoral artery, none of the branches of the deep femoral artery continue into the lower leg or foot.

Like most blood vessels, the femoral artery is made of several distinct tissue layers that help it to deliver blood to the tissues of the leg. The innermost layer, known as the endothelium or tunica intima, is made of thin, simple squamous epithelium that holds the blood inside the hollow lumen of the blood vessel and prevents platelets from sticking to the surface and forming blood clots. Surrounding the tunica intima is a thicker middle layer of connective tissues known as the tunica media. The tunica media contains many elastic and collagen fibers that give the femoral artery its strength and elasticity to withstand the force of blood pressure inside the vessel. Visceral muscle in the tunica media may contract or relax to help regulate the amount of blood flow. Finally, the tunica externa is the outermost layer of the femoral artery that contains many collagen fibers to reinforce the artery and anchor it to the surrounding tissues so that it remains stationary.

The femoral artery is classified as an elastic artery, meaning that it contains many elastic fibers that allow it to stretch in response to blood pressure. Every contraction of the heart causes a sudden increase in the blood pressure in the femoral artery, and the artery wall expands to accommodate the blood. This property allows the femoral artery to be used to detect a person's pulse through the skin (See, e.g., The Cardiovascular System at a Glance, $4^{th}$ Edition, Philip I. Aaronson, Jeremy P. T. Ward, Michelle J. Connolly, November 2012, © 2012, Wiley-Blackwell, Hoboken, N.J.).

Use of the Femoral Artery for Endovascular Procedures

Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort (Alvarez-Tostado J. A. et al. Journal of Vascular Surgery 2009; 49(2): 378-385). Femoral puncture also allows access to virtually all of the arterial territories and affords favorable ergonomics for the operator in most instances (Alvarez-Tostado J. A. et al. Journal of Vascular Surgery 2009; 49(2): 378-385).

Brachial Artery

The brachial artery is a major blood vessel located in the upper arm and is the main supplier of blood to the arm and hand. It continues from the axillary artery at the shoulder and travels down the underside of the arm. Along with the medial cubital vein and bicep tendon, it forms the cubital fossa, a triangular pit on the inside of the elbow. Below the cubital fossa, the brachial artery divides into two arteries running down the forearm: the ulnar and the radial; the two main branches of the brachial artery. Other branches of the brachial artery include the inferior ulnar collateral, profunda brachii, and superior ulnar arteries (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N.J.).

Use of the Brachial Artery for Endovascular Procedures

Brachial artery access is a critical component of complex endovascular procedures, especially in instances where femoral access is difficult or contraindicated, such as the absence of palpable femoral pulses, severe common femoral occlusive disease, recent femoral intervention or surgery or femoral aneurysms/pseudoaneurysms. It is a straightforward procedure with a high success rate for percutaneous cannulation (Alvarez-Tostado J. A. et al. Journal of Vascular Surgery 2009; 49(2): 378-385). However, there is a general reluctance to puncture the right brachial artery due to the need to navigate through the innominate artery and arch and due to the risk for complications such as direct nerve trauma and ischemic occlusion resulting in long-term disability (Alvarez-Tostado J. A. et al. Journal of Vascular Surgery 2009; 49(2): 378-385; Cousins T. R. and O'Donnell J. M. AANA Journal 2004; 72(4): 267-271).

Cerebral/Intracranial Aneurysms

An aneurysm in the brain (i.e., cerebral or intracranial aneurysm) is a weak area in the wall of a cerebral blood vessel that causes the blood vessel to bulge or balloon out. Aneurysms typically develop during adulthood and rupture risk increases with age. Subarachnoid hemorrhage (SAH) is the most serious presentation of ruptured intracranial aneurysms (Seibert B et al. Frontiers in Neurology 2011; 2(45): 1-11). The mean age for aneurysmal SAH is about 50 years (Phillips L H et al. Neurology 1980; 30, 1034-1040). Estimated annual incidence rates of SAH range from 10 to 15 cases per 100,000; roughly 30,000 cases of SAH in the United States each year. Two-thirds of patients with aneurysm rupture either die or have a disabling neurological deficit (Stapf C and Mohr J P (2004) "Aneurysms and subarachnoid hemorrhage—epidemiology," in Management of Cerebral Aneurysms, eds. LeRoux P D, Winn H R, Newell D W, editors. (Philadelphia: Saunders), 183-187). More specifically, ruptured aneurysms account for approximately 85% of non-traumatic SAH and are associated with a 30-day mortality rate of 45% and a morbidity rate of 25% (van Gijn J et al. Lancet 2007; 369 (9558): 306-318).

Typical locations at risk for the development of aneurysms are vessel branching points, where structural irregularities in the collagen matrix exist, and elevated hemodynamic stresses due to segments involving short radii of curvature are more observed (Meng H et al. Stroke 2007; 38(6): 1924-1931; Finlay H M et al. Stroke 1998; 29(8): 1595-1601; Rowe A J et al. J. Vasc. Res. 2003; 40(4): 406-415). Studies have shown that abnormal hemodynamic stress plays an important role in aneurysm formation and growth (Meng H et al. Stroke 2007; 38(6): 1924-1931).

Classification of Cerebral/Intracranial Aneurysms

Several schemes are used to classify intracranial aneurysms; the most obvious being ruptured lesions versus unruptured lesions (Seibert B et al. Frontiers in Neurology 2011; 2(45): 1-11). With respect to morphology, aneurysms are classified as saccular (rounded shape) or non-saccular. Non-saccular intracranial aneurysms such as fusiform (spindle-shaped), dolichoectatic (widening of a segment of an artery around the entire blood vessel), and dissecting aneurysms (artery wall rips longitudinally) are rare with an incidence of less than 0.1% (Anson J A et al. J. Neurosurg. 1996; 84(2): 185-193). Intracranial aneurysms also are classified by aneurysm location. The predominant location for saccular aneurysms is the anterior circulation (about 90%), with most arising from the circle of Willis (Bonneville F et al. Neuroimaging Clin. N. Am. 2006; 16(3): 371-382). The anterior communicating complex is the most common location (roughly 30-35%), followed by the internal carotid artery (roughly 30%). The basilar apex represents the most common location in the posterior circulation and accounts for about 10% of all intracranial aneurysms (Bonneville F et al. Neuroimaging Clin. N. Am. 2006; 16(3): 371-382). Aneurysms are also classified by size. Size classification subgroups include small (<10 mm), large (10-25 mm), and giant (>25 mm) in diameter. According to Wiebers et al., aneurysms smaller than 12 mm in dome size account for more than 75% of unruptured aneurysms (Wiebers D O et al. Lancet 2003; 362(9378): 103-110). The establishment of endovascular therapy has led to further classification of aneurysms based on the size of the aneurysmal neck (Seibert B et al. Frontiers in Neurology 2011; 2(45): 1-11).

Pathophysiology of Cerebral/Intracranial Aneurysms

Formation of an intracranial aneurysm is thought to be a consequence of a systemic vascular pathology, which is associated with pleomorphisms in different candidate genes (Krex D et al. Acta Neurochir. (Wien) 2001; 143(5): 429-448; Yurt A et al. J. Clin. Neurosci. 2010; 17(9): 1119-1121). A higher prevalence of aneurysms in the cerebrovascular system may also be attributed to alterations in hemodynamic and histological features (Stehbens W E et al. Neurol. Res. 1990; 12(1): 29-34; Kondo S et al. Stroke 1997; 28(2): 398-403; Rowe A J et al. J. Vasc. Res. 2003; 40(4): 406-415; Shojima M et al. Stroke 2004; 35(11): 2500-2505). Cerebral arteries are particularly susceptible to aneurysm formation due to the absence of an external elastic lamina (tissue that forms the outermost part of the tunica intima), lack of supportive perivascular tissues, attenuated tunica media, and irregularities near bifurcations (Stehbens W E et al. Neurol. Res. 1990; 12(1): 29-34; Rowe A J et al. J. Vasc. Res. 2003; 40(4): 406-415). The internal elastic lamina is an important layer of the arterial wall, especially in cerebral vessels. Disruption of this layer would promote formation of aneurysms (Yong-Zhong G and van Alphen H A Neurol. Res. 1990; 12(4): 249-255). Particularly, the regions around the bifurcations have atypical wall structures with a discontinuity of the muscle cells of the tunica media as a medial defect in connection with a predominance of collagen fibers over elastic fibers (Rowe A J et al. J. Vasc. Res. 2003; 40(4): 406-415; Seibert B et al. Frontiers in Neurology 2011; 2(45): 1-11). In addition to these atypical wall structures, non-uniform collagen framework in the bifurcation region of brain arteries may further induce development of intracranial aneurysms (Rowe A J et al. J. Vasc. Res. 2003; 40(4): 406-415).

Several studies have demonstrated that arterial blood flow disturbance and hypertension in the brain vessels lead to increased hemodynamic stress on arterial walls. Some studies also present strong association between wall shear stress (WSS) and initiation of cerebral aneurysm formation in experimental models (Kondo S. et al. Stroke 1997; 28(2): 398-403; Shojima M et al. Stroke 2004; 35(11): 2500-2505). A prolonged high WSS induces matrix metalloproteinase production and fragmentation of the internal elastic lamina at, or immediately adjacent to, the apex of vessel bifurcations (Masuda H et al. Arterioscler. Thromb. Vasc. Biol. 1999: 19(10): 2298-2307; Shojima M et al. Stroke 2004; 35(11): 2500-2505; Meng H et al. Stroke 2007; 38(6): 1924-1931). Prolonged elevation of blood pressure leads to excessive mechanical loading and causes remodeling of the arterial wall. The exact mechanisms involved in the tissue remodeling are not completely understood, but decreased structural integrity of the tissue may be one of the underlying factors contributing to aneurysm formation and growth (Seibert B et al. Frontiers in Neurology 2011; 2(45): 1-11).

Types of Cerebral/Intracranial Aneurysms

Saccular Intracranial Aneurysms

Saccular intracranial aneurysms, which account for 90% of intracranial aneurysms, are a result of aberrations to the normal arterial structure, which consists of the tunica intima (adjacent to the lumen of the vessel), the tunica media (the muscular middle layer), and the tunica adventitia (the outer layer composed mainly of connective tissue) (Keedy A Mcgill J. Med. 2006; 9(2): 141-146). Saccular aneurysms occur when there is collagen deficiency in the internal elastic lamina and breakdown of the tunica media. An outpouching, consisting of only tunica intima and adventitia, protrudes through the defect in the internal elastic lamina and tunica media to produce the aneurysmal sac (Austin G et al. Ann. Clin. Lab. Sci. 1993; 23(2): 97-105; Stehbens W E et al. Surg. Neurol. 1989; 31(3): 200-202). The impaired integrity of the wall may be due to congenital weakness or absence of the tunica media or adventitia, degenerative alterations of the internal elastic lamina (from hypertension, turbulent flow, or atherosclerotic deposits in the wall), or both (Gasparotti R et al. Eur. Radiol. 2005; 15(3): 441-447). Low collagen and elevated plasma elastase have been observed in patients with aneurysms, suggesting that vascular remodeling involving collagen and elastin plays a role saccular intracranial aneurysm formation (Wagner M and Stenger K Crit. Care Nurs. Q. 2005; 28(4): 341-354).

Fusiform Intracranial Aneurysms

Fusiform aneurysms are nonsaccular dilatations involving the entire vessel wall for a short distance, exhibiting a spindle shape when viewed externally (Al-Yamany M and Ross I B Br. J. Neurosurg. 1998; 12(6):572-57; Ceylan S et al. Neurosurg. Rev. 1998; 21(2-3):189-193; Day A L et al. J. Neurosurg. 2003; 99(2):228-240; Findlay J M et al. Can. J. Neurol. Sci. 2002; 29(1): 41-48; Nakayama Y et al. Surg. Neurol. 1999; 51(2): 140-145). This type of aneurysm may be caused by dissection or atherosclerosis, by disorders of collagen and elastin metabolism, by infections and, although rare, by neoplastic invasion of the arterial wall (Ceylan S et al. Neurosurg. Rev. 1998; 21(2-3):189-193; Day A L et al. J. Neurosurg. 2003; 99(2):228-240; Otawara Y et al. Neurosurg. Rev. 1997; 20(2):145-148; Selviaridis P et al. Acta Neurochir (Wien) 2002; 144(3): 295-299). Fusiform aneurysms have different underlying pathologies, hemodynamics, anatomical distributions, natural histories and treatments than do the saccular variety (Day A L et al. J. Neurosurg. 2003; 99(2):228-240). Intracranial fusiform aneurysms are rare, although the number of cases has increased in recent years. They represent approximately 3%-13% of all intracranial aneurysms and are usually located in the vertebrobasilar system (Al-Yamany M and Ross I B Br. J. Neurosurg. 1998; 12(6):572-57; Drake C G and Peerless S J J. Neurosurg. 1997; 87(2); 141-162; Findlay J M et al. Can. J. Neurol. Sci. 2002; 29(1): 41-48).

Intracranial Vertebral Artery Dissecting Aneurysms

Intracranial vertebral artery dissecting (VAD) aneurysms result from a tear in the wall of an artery leading to the intrusion of blood within the layers of the arterial wall, more specifically, from a tear in the wall of a major artery leading to the intrusion of blood (intramural hematoma) between the media and the adventitia (Park K-W et al. J. Korean Neurosurg. Soc. 2008; 44(3): 109-115; Thanvi B et al. Postgrad. Med. J. 2005; 81(956): 383-388). The overall incidence of VAD is approximately 1-1.5 per 100,000 (Park K-W et al. J. Korean Neurosurg. Soc. 2008; 44(3): 109-115). Spontaneous dissections of the carotid and vertebral artery account for only about 2 percent of ischemic strokes, but they are a major cause of ischemic stroke in young and middle-aged patients (roughly 10% to 25%) (Bassetti C et al. Stroke 1996; 27(10): 1804-1807; Giroud M et al. J. Neurol. Neurosurg. Psychiatry 1994; 57(11): 1443; Schievink W I Curr. Opin. Cardiol. 2000; 15(5): 316-321; Schievink W I et al. Neruology 1994; 330(6): 393-397). Spontaneous dissections of the vertebral arteries affect all age groups, including children, but there is a distinct peak in the fifth decade of life (Bassetti C et al. Stroke 1996; 27(10): 1804-1807; Schievink W I et al. Neurology 1994; 330(6): 393-397; Schievink W I et al. Neurology 1994; 44(9): 1607-1612).

Patients with a spontaneous dissection of the vertebral artery are thought to have an underlying structural defect of the arterial wall (Park K-W et al. J. Korean Neurosurg. Soc. 2008; 44(3): 109-115; Schievink W I N. Eng. J. Med. 2001; 344(12): 898-906). Heritable connective tissue disorders, such as Ehlers-Danlos syndrome type IV, Marfan's syndrome, autosomal dominant polycystic kidney disease, and osteogenesis imperfecta type I, are believed to be associated with an increased risk of spontaneous dissections of the vertebral arteries (Schievink W I et al. Stroke 1994; 25(12): 2492-2496; Schievink W I et al. Stroke 1994; 25(4): 889-903).

Mycotic Intracranial Aneurysms

Cerebral mycotic aneurysms (CMAs) or infectious intracranial aneurysms represent less than 5% of all intracerebral aneurysms (Kannoth S et al. J. Neurolog. Sci. 2007; 256: 3-9). CMAs are most commonly seen in patients with septicemia and HIV/AIDS and are a particularly well-known complication of infective endocarditis (IE). Intravenous drug abuse and "relative immunocompromised" states such as diabetes are becoming more commonly associated with CMAs (Corr P et al. Am. J. Neuroradiol. 1995; 16: 745-48; Peters P J et al. Lancet Infect. Dis. 2006; 6: 742-748; Lee W K et al. Radiographics 2008; 28: 1853-1868). Studies have shown that between 1%-10% of patients with IE have CMAs; and of patients with CMAs, approximately 65% have IE (Peters P J et al. Lancet Infect. Dis. 2006; 6: 742-748; Ducruet A F et al. Neurosurg. Rev. 2010; 33: 37-46). In "strongly immunocompromised" patients, CMAs are prone to more rapid growth and rupture (Hurst R W et al. Am. J. Neuroradiol. 2001; 22: 858-863; Horten B C et al. Arch. Neurol. 1976; 33: 577-579; Minnerup J et al. Neurology 2008; 71: 1745). If there is direct meningeal extension of infection, CMAs are often located more proximally than their usual location at distal branch points. In addition, CMAs from atypical infections, especially fungal infections, are particularly lethal (Hurst R W et al. Am. J. Neuroradiol. 2001; 22: 858-863; Horten B C et al. Arch. Neurol. 1976; 33: 577-579; Minnerup J et al. Neurology 2008; 71: 1745).

Cavernous Carotid Aneurysms (CCAs)

Cavernous carotid aneurysms (CCAs) are considered benign lesions of the cavernous internal carotid artery which are most often asymptomatic (Eddleman C S et al. Neurosurgical Focus 2009; 26(5): E4). These aneurysms, especially when small, rarely rupture and thus have a low risk of causing major morbidity and mortality (Eddleman C S et al. Neurosurgical Focus 2009; 26(5): E4; Kupersmith M J et al. J Stroke Cerebrovasc Dis 2002; 11:9-14; Stiebel-Kalish H, et al. Neurosurgery 2005; 57:850-57; Wiebers D. Lancet 2003; 362:103-10). Larger CCAs (>13 mm) have a 5-year rupture rate of 9.4% (Wiebers D. Lancet 2003; 362:103-10). When they do rupture, CCAs typically rupture into the cavernous sinus, which leads to carotid cavernous fistula formation (a short-circuiting of the arterial blood into the venous system of the cavernous sinuses; See Karaman E et al. J. Craniofac. Surg. 2009; 20(2); 556-558); a far less catastrophic event than rupture of intradural aneurysms (Tanweer O et al. Am. J. Neuroradiol. 2014; 35: 2334-2340). However, although rare, once CCAs reach the size at which they penetrate or protrude through the dura, they carry the risk of subarachnoid hemorrhage (SAH) (Eddleman C S et al. Neurosurgical Focus 2009; 26(5): E4; Tanweer O et al. Am. J. Neuroradiol. 2014; 35: 2334-2340).

Treatment of Aneurysms

Surgical Clipping

Surgical clipping of an intracranial aneurysm, which involves the application of a silver clip across the neck of the aneurysm, has the advantage of being a time-honored, durable and versatile method for treating most intracranial aneurysms (Seibert B et al. Front. Neruol. 2011; 2(45): 1-11). It is rare for an intracranial aneurysm to recur once it has been properly clipped, and there are very few aneurysms that are not amenable to some surgical repair technique (Campi A et al. Stroke 2007; 38(5): 1538-1544; Tsutsumi K et al. Stroke 2001; 32(5): 1191-1194).

However, surgical repair of intracranial aneurysms does have several disadvantages; including that it requires an open operation and physical manipulation of the brain (Mason A M et al. J. Korean Neurosurg. Soc. 2009; 45(3): 133-142). A number of characteristics of either the patient and/or the aneurysm can make them undesirable for surgical management as well, including aneurysms in elderly patients, patients in very poor medical condition or who present with cerebral vasospasm, patients who have multiple aneurysms or aneurysms that have calcified necks or unfavorable surgical anatomy (e.g., fusiform aneurysms, blister-like aneurysms, wide-neck aneurysms, thrombotic aneurysms, giant aneurysms, aneurysms <3 mm in size, etc.) (Mason A M et al. J. Korean Neurosurg. Soc. 2009; 45(3): 133-142).

Endovascular Coiling

Endovascular coiling is a minimally invasive technique performed to prevent blood from flowing into an aneurysm. During endovascular coiling, a catheter is passed through the groin up to the artery containing the aneurysm. A microcatheter with a coil attached is inserted through the initial catheter. When the microcatheter has reached and been inserted into the aneurysm, an electrical current is used to separate the coil from the catheter. The coil is permanently left to seal off the opening of the aneurysm. Depending on the size of the aneurysm, more than one coil may be needed to completely seal off the aneurysm. The coil induces embolization (clotting) of the aneurysm, which prevents blood from flowing into the aneurysm, which in turn, prevents subarachnoid hemorrhage (Seibert B et al. Frontiers in Neurology 2011; 2(45): 1-11).

While endovascular coiling of intracranial aneurysms has offered an alternative treatment option to open surgery (i.e., surgical clipping), there are serious risks to consider. Some of these risks overlap with those seen in surgical clipping and others are unique to endovascular therapy. Procedural complications include thromboembolism, cerebral embolization, aneurysm perforation, parent artery occlusion, coil migration, arterial dissection, and vasospasm (Murayama Y et al. J. Neurosurg. 2003; 98(5): 959-966; Gonzalez N et al. Am. J. Neuroradiol. 2004; 25(4): 577-583).

Stent-Assisted Coiling

Stent-assisted coiling has improved the ability to treat difficult and complicated aneurysms. However, while these devices provide another treatment option for endovascular repair, additional risks are associated with stent placement compared to coiling alone (Seibert B et al. Frontiers in Neurology 2011; 2(45): 1-11). Placing a stent in the parent artery requires lifetime use of anti-platelet agents to reduce the risk of thrombosis based stenosis within the stent (Kanaan H et al. Neurosurgery 2010; 67(6): 1523-1532). The need for anti-platelet therapy limits the role of stent placement in patients with ruptured aneurysms. These patients may need additional invasive procedures such as ventriculostomy, decompressive craniectomy, tracheostomy, or gastrostomy (Seibert B et al. Frontiers in Neurology 2011; 2(45): 1-11). The risk of these procedures is increased due to anti-platelet or anticoagulation therapy (Mocco J et al. J. Neurosurg. 2009; 110(1): 35-39).

Flow Diversion

The primary goal of a flow diversion device is to divert flow away from the aneurysm by placing a mesh stent or a structure similar to a stent, on the aneurysm neck along the parent artery. By decoupling blood flow between the parent artery and aneurysmal sack, a flow diverter can create blood stasis to allow for thrombus formation inside the aneurysm. In terms of design, flow diversion devices consist of a highly flexible tubular structure with a mesh. The porosity of the mesh is less than that of typical stents (Seibert B et al. Frontiers in Neurology 2011; 2(45): 1-11).

These devices are typically deployed in situations where established techniques, such as coiling and stent-assisted coiling, are not viable options. However, increased technical complications with deployment of flow diverters have been reported. In one study, an overall complication rate of 38%, including parent artery stenosis, distal embolism, in-device thrombosis, branch occlusion, and hemorrhage or mass effects was reported (Lubicz B et al. Stroke 2010; 41(10): 2247-2253). In another study, parent artery occlusion was seen in seven (14%) patients, with additional arterial narrowing in three (6%) patients (Byrne J et al. Plos ONE 2010; 2; 5(9). pii: e12492. Doi: 10.1371/journal.pone.0012492).

In addition, clinicians must use caution in deployment of flow diverters when aneurysms are located near regions of side branching arteries. Incorrect placement could prevent blood flow to an otherwise healthy artery. Another concern with flow diverters is that the low porosity (i.e., small open spaces in the mesh) needed to reduce blood flow, will be problematic if additional coiling is needed after deployment. Anti-coagulants required for flow diverters may be beneficial for prevention of in-device thrombus, but could negatively impact the time for thrombus formation inside the aneurysm without the additional coil packing used with stents. The interaction of thrombus formation inside aneurysms is not clearly understood. It has been suggested that such thrombus formation could lead to rupture after deployment of a flow diverter (Kulcsar Z et al. Am. J. Neuroadiol. 2011; 32(1): 20-25).

A common complication of endovascular aneurysm repair is the occurrence of an endoleak (persistent blood within the aneurysmal sac following a flow diversion and/or covered stent procedure), which is found in 30-40% of patients intraoperatively (detected by on-table angiogram after flow-diverter and/or peripheral covered stent deployment) and 20-40% of patients during a follow-up examination. Some endoleaks are unavoidable due to the presence of pre-existing patent branch vessels arising from the aneurysm sac, while others occur as a result of poor patient/flow-diverter/covered stent selection. In the latter group, some regions of the stent are poorly apposed to the vessel wall after deployment of the device, allowing "leakage" of a stream of blood between the device and the vessel wall, which continues to fill the aneurysm and/or fistula.

Carotid-Cavernous Fistulas (CCF)

A carotid cavernous fistula (CCF) results from an abnormal communication between the arterial and venous systems within the cavernous sinus in the skull. As arterial blood under high pressure enters the cavernous sinus, the normal venous return to the cavernous sinus is impeded. This causes engorgement of the draining veins, manifesting most dramatically as a sudden engorgement and redness of the eye of the same side. A CCF may form following closed or penetrating head trauma, surgical damage, rupture of an intracavernous aneurysm or in association with connective tissue disorders, vascular diseases and dural fistulas.

Classification of CCFs

Various classifications have been proposed for CCF. For example, CCFs may be divided into low-flow or high-flow, traumatic or spontaneous, and direct or indirect. A traumatic CCF typically occurs after a basal skull fracture. A spontaneous dural cavernous fistula, which is more common, usually results from a degenerative process in older patients with systemic hypertension and atherosclerosis. Direct fistulas occur when the internal carotid artery (ICA) fistulizes into the cavernous sinus whereas indirect fistulas occur when a branch of the ICA or external carotid artery (ECA) communicates with the cavernous sinus.

Table 1 shows one classification system that divides CCF into four varieties based on the type of arterial supply.

TABLE 1

CCF classification based on arterial blood supply.

| Classification Type | Classification Description |
|---|---|
| A | Fistulous supply from the internal carotid artery |
| B | Supply from the dural branches of internal carotid artery (ICA) |
| C | Supply from meningeal branches of external carotid artery (ECA) |
| D | Combined supply from ICA and ECA |

Symptoms of CCF

CCF symptoms include pain, bruit (a humming sound within the skull due to high blood flow through the arteriovenous fistula), progressive visual loss, and pulsatile or progressive proptosis (bulging of the eye anteriorly out of the orbit).

Diagnosis of CCF

Diagnosis is based on magnetic resonance imaging (MRI) scan, magnetic resonance angiography and computerized tomography (CT) scan. A cerebral digital subtraction angiography (DSA) enhances visualization of the fistula. CT scans classically show an enlarged superior ophthalmic vein, cavernous sinus enlargement ipsilateral (on the same side) to the abnormality, and possibly diffuse enlargement of all the extraocular muscles resulting from venous engorgement. Selective arteriography is used to evaluate arteriovenous fistulas.

Treatment of CCF

Endovascular therapy is the mainstay of treatment for CCF. This may be trans-arterial (mostly in the case of direct CCF) or trans-venous (most commonly in indirect CCF). Occasionally, more direct approaches, such as direct transorbital puncture of the cavernous sinus or cannulation of the draining superior orbital vein are used when conventional approaches are not possible. Spontaneous resolution of indirect fistulae has been reported but is uncommon. Staged manual compression of the ipsilateral carotid has been reported to assist with spontaneous closure in selected cases.

Direct CCFs may be treated by occlusion of the affected cavernous sinus (with coils, balloon, liquid agents, etc.), or by reconstruction of the damaged internal carotid artery (using stent, coils or liquid agents). Indirect CCFs may be treated by occlusion of the affected cavernous sinus with coils, liquid agents or a combination of both (Ong C K et al. Journal of Medical Imaging and Radiation Oncology. 2009; 53(3): 291-295; Bhatia K D et al. Journal of Neuro-Ophthalmology. 2009; 29(1): 3-8; Nadarajah M et al. Journal of NeuroInterventional Surgery. 2011; 4(3): e1).

A need exists for an endovascular device capable of treating diseases that require endovascular intervention in a patient suffering from an intracranial aneurysm or a carotid cavernous fistula. The advantages that the described invention possess over comparable devices in treating intracranial aneurysms and carotid cavernous fistulas would be apparent to those skilled in the art. The described invention provides a covered stent device capable of effectively treating such patients by diverting blood flow away from an aneurysm or fistula while allowing blood to flow to critical, healthy adjacent side branching arteries, resulting in blood stasis and thrombus formation inside the aneurysm or fistula.

SUMMARY OF THE INVENTION

According to one aspect, the described invention provides an endovascular stent device comprising a tubular structure comprising a circumference; wherein a flow-diverting portion of the circumference is covered by a flow-diverting material; a length (l) from a proximal end to a distal end ranging in size from about 1 mm to about 800 mm; and an inner diameter (d) ranging from about 0.1 mm to about 150 mm; wherein the flow-diverting portion of the circumference comprises a length (l') ranging from about 1 mm to about 800 mm; and the flow-diverting portion of the circumference covers at least 1% to at least 100% of the endovascular stent device.

According to one embodiment, the flow-diverting portion is located: a. at the distal end of the stent; or b. at the proximal end of the stent; or c. an equidistance from the distal end and proximal end of the stent; or d. at any location along the length (l) of the stent; or e. at multiple locations along the length (l) of the stent; or f. on one side of the circumference of the stent; or g. on a portion of the circumference of the stent.

According to one embodiment, (a) the flow-diverting material is a non-permeable material or a selectively permeable material; or (b) the flow-diverting material is a thermoplastic, a hydrogel or a combination thereof; or (c) the flow-diverting material is in form of a sheet; or (d) the flow-diverting material is in form of closely approximated struts; or (e) a combination of (a) and (b); or (f) a combination of (a) and (c); or (g) a combination of (a) and (d); or (h) a combination of (b) and (c); or (i) a combination of (b) and (d); or (j) a combination of (c) and (d).

According to one embodiment, the thermoplastic is selected from the group consisting of nylon, polyethylene terephthalate (PET) (Dacron®), urethane, polyethylene, polyvinyl chloride (PVC), polyether ether ketone (PEEK) and polyester. According to another embodiment, the thermoplastic is polyethylene terephthalate (PET) (Dacron®).

According to one embodiment, (a) the hydrogel is a non-biodegradable polymer; or (b) the hydrogel is selected from the group consisting of a synthetic polymer, a natural polymer and a mixed synthetic-natural polymer; or (c) the hydrogel is adapted to be applied to the stent or is adapted to be applied to a filament woven onto the stent; or is adapted to be directly adhered to the struts of the stent (d) the hydrogel is adapted to expand upon exposure to blood; or (e) the hydrogel is adapted to expand upon exposure to blood to cover at least 1% to at least 100% of the length (l') of the flow-diverting portion of the stent; or (f) the hydrogel is adapted to expand in vivo to decrease permeability of the flow-diverting portion of the stent; or (g) the hydrogel is a crosslinked acrylamide-sodium acrylate co-polymer.

According to one embodiment, (a) the sheet is adapted to cover the outside of the flow-diverting portion of the stent; or (b) the sheet is adapted to cover the inside of the flow-diverting portion of the stent; or (c) the sheet is adapted to cover between struts of the flow-diverting portion of the stent; or (d) the sheet comprises a thermoplastic selected from the group consisting of nylon, polyethylene terephthalate (PET) (Dacron®), urethane, polyethylene, polyvinyl chloride (PVC), polyether ether ketone (PEEK) and polyester.

According to another embodiment, (a) the flow-diverting material is a hydrogel-coated polyethylene terephthalate (PET) (Dacron®); or (b) the flow-diverting material is adapted to increase blood vessel wall adherence and minimize risk of an endoleak; or (c) the flow-diverting material is adapted to increase blood vessel wall adherence and minimize risk of an endoleak by coating the flow-diverting material with a hydrogel.

According to one embodiment, the endovascular stent device comprises a non-anchor portion and an anchor portion adapted to anchor the stent in a blood vessel.

According to one embodiment, (a) the anchor portion is located at the distal end of the stent device; or (b) the anchor portion is located at the proximal end of the stent device; or (c) the anchor portion is located at both the distal end and the proximal end of the stent device; or (d) the anchor portion is located at multiple intervals along the length (l) of the stent.

According to one embodiment, (a) the non-anchor portion and the anchor portion comprise interstices; or (b) the interstices of the anchor portion are larger than the interstices of the non-anchor portion; or (c) the insterstices in a non-flow diverting portion are larger than the interstices in the flow-diverting portion.

According to one embodiment, the endovascular stent device comprises (a) a constraint so that its diameter is smaller than a blood vessel until delivery to the blood vessel, and is adapted to self-expand upon removal of the constraint; or (b) a constraint and a balloon so that its diameter is smaller than a blood vessel until delivery to the blood vessel, and the balloon is adapted to expand the stent to blood vessel diameter after inflation; or (c) a constraint so that a portion of its diameter is smaller than a blood vessel until delivery to the blood vessel, and is adapted to self-expand upon removal of the constraint; or (d) a constraint and a balloon so that a portion of its diameter is smaller than a blood vessel until delivery to the blood vessel, and the balloon is adapted to expand the stent to blood vessel diameter after inflation; or (e) a combination of (a) and (b); or (f) a combination of (c) and (d); or (g) a combination of (a) and (d); or (h) a combination of (b) and (c).

According to one embodiment, the endovascular stent device comprises a radiopaque marker for positioning the stent in the blood vessel, wherein: a. the radiopaque marker is at the distal end of the stent device; or b. the radiopaque marker is at the proximal end of the stent device; or c. the radiopaque marker is at both the distal end and the proximal end of the stent device; or d. the radiopaque marker is at a distal end of the flow-diverting portion of the stent device; or e. the radiopaque marker is at a proximal end of the flow-diverting portion of the stent device; or f. the radiopaque marker is at both a distal end and a proximal end of the flow-diverting portion of the stent device; or g. the radiopaque marker is at a distal end of a covered portion of the stent device; or h. the radiopaque marker is at a proximal end of a covered portion stent device; or i. the radiopaque marker is at both a distal end and a proximal end of a covered portion of the stent; or j. the radiopaque marker is at a distal end of the flow-diverting portion and at a distal end of a covered portion of the stent device; or k. the radiopaque marker is at a proximal end of the flow-diverting portion and at a proximal end of a covered portion of the stent device; or l. the radiopaque marker is at both distal and proximal ends of the flow-diverting portion and a covered portion of the stent device; or m. the stent device comprises multiple radiopaque markers along the length (l) of the stent device and throughout the circumference of the stent device.

According to one embodiment, (a) the endovascular stent device is adapted for intracranial blood vessels; or (b) the endovascular stent device is adapted for peripheral blood vessels; or (c) the endovascular stent device is adapted for cardiac vessels.

According to one embodiment, (a) the endovascular stent device is adapted to be retrieved from a blood vessel when about 0% to about 100% of the stent device is deployed in the blood vessel; or (b) the endovascular stent device is adapted to be re-positioned in a blood vessel when about 0% to about 100% of the stent device is deployed in the blood vessel; or (c) the endovascular stent device is adapted to be re-sheathed in a blood vessel when about 0% to about 100% of the stent device is deployed in the blood vessel.

According to one embodiment, (a) the endovascular stent device is connected to a wire; or (b) the endovascular stent device is connected to a single site on a wire; or (c) multiple sites on the endovascular stent device connect to a single site on a wire; or (d) multiple sites on the endovascular stent device connect to multiple sites on a wire; or (e) the endovascular stent device is connected to a detachable site on a wire; or (f) the endovascular stent device is connected to a single detachable site on a wire; or (g) multiple sites on the endovascular stent device connect to a single detachable site on a wire; or (h) multiple sites on the endovascular stent device connect to multiple detachable sites on a wire; or (i) the endovascular stent device is not connected to a wire.

According to one embodiment, (a) the detachable site on the wire is a mechanically detachable site; or (b) the detachable site on the wire is an electrolytically detachable site; or (c) the detachable site on the wire is a hydrostatically detachable site; or (d) the multiple detachable sites on the wire are mechanically detachable sites; or (e) the multiple detachable sites on the wire are electrolytically detachable sites; or (f) the multiple detachable sites on the wire are hydrostatically detachable sites.

According to one embodiment, (a) the endovascular stent device is tapered at the proximal end; or (b) the endovascular stent device is tapered at the distal end; or (c) the endovascular stent device is tapered at a site along the length (l) of the stent; or (d) the endovascular stent device is tapered at multiple sites along the length (l) of the stent; or (e) the endovascular stent device is flared at the proximal end; or (f) the endovascular stent device is flared at the distal end; or (g) the endovascular stent device is flared at a site along the length (l) of the stent; or (h) the endovascular stent device is flared at multiple sites along the length (l) of the stent; or (i) a combination thereof.

According to one embodiment, the endovascular device comprises two or more struts adapted to resist compression spaced at intervals along the length 1 of the stent. According to another embodiment, (a) the struts are spaced evenly or unevenly along the length 1 of the stent; or (b) the flow-diverting portion comprises two or more struts; or (c) the two or more struts are connected to a wire; or (d) the two or more struts comprise a hydrogel and/or have a hydrogel adhered to it; or (e) the endovascular stent device is adapted to be retrieved from a blood vessel when about 0% to about 100% of the stent device is deployed in the blood vessel; or (f) the endovascular stent device is adapted to be re-positioned in a blood vessel when about 0% to about 100% of the stent device is deployed in the blood vessel; or (g) the endovascular stent device is adapted to be re-sheathed in a blood vessel when about 0% to about 100% of the stent device is deployed in the blood vessel; or (h) the endovascular stent device is tapered at the proximal end; or (i) the endovascular stent device is tapered at the distal end; or (j) the endovascular stent device is tapered at a site along the length (l) of the stent; or (k) the endovascular stent device is tapered at multiple sites along the length (l) of the stent; or (l) the endovascular stent device is flared at the proximal end; or (m) the endovascular stent device is flared at the distal end; or (n) the endovascular stent device is flared at a site along the length (l) of the stent; or (o) the endovascular stent device is flared at multiple sites along the length (l) of the stent; or (p) a combination thereof.

According to one embodiment, (a) the hydrogel is applied to each strut; or (b) the hydrogel is applied to select strut or struts and/or select regions of one or more struts; or (c) the hydrogel is applied to an inner wall of each strut; or (d) the hydrogel is applied to an outer wall of each strut; or (e) the hydrogel is applied to a surface of the strut facing other adjacent struts; or (f) the hydrogel is a non-biodegradable polymer; or (g) the hydrogel is a non-biodegradable polymer selected from the group consisting of a synthetic polymer, a natural polymer and a mixed synthetic-natural polymer; or (h) the hydrogel expands upon exposure to blood; (i) the hydrogel expands upon exposure to body temperature; or (j) the hydrogel applied to one strut is adapted to expand to reach the hydrogel applied to adjacent struts; or (k) the hydrogel is adapted to expand upon exposure to blood to cover at least 1% to at least 100% of the length (l') of the flow-diverting portion of the stent; or (g) the hydrogel is adapted to expand in vivo to decrease permeability of the flow-diverting portion of the stent.

According to one embodiment, (a) the endovascular stent device is connected to a wire; or (b) the endovascular stent device is connected to a single site on a wire; or (c) multiple sites on the endovascular stent device connect to a single site on a wire; or (d) multiple sites on the endovascular stent device connect to multiple sites on a wire; or (e) the endovascular stent device is connected to a detachable site on a wire; or (f) the endovascular stent device is connected to a single detachable site on a wire; or (g) multiple sites on the endovascular stent device connect to a single detachable site on a wire; or (h) multiple sites on the endovascular stent device connect to multiple detachable sites on a wire; or (i) the endovascular stent device is not connected to a wire.

According to one embodiment, (a) the detachable site on the wire is a mechanically detachable site; or (b) the detachable site on the wire is an electrolytically detachable site; or (c) the detachable site on the wire is a hydrostatically detachable site; or (d) the multiple detachable sites on the wire are mechanically detachable sites; or (e) the multiple detachable sites on the wire are electrolytically detachable sites; or (f) the multiple detachable sites on the wire are hydrostatically detachable sites.

According to one embodiment, the endovascular stent device comprises (a) a constraint so that its diameter is smaller than a blood vessel until delivery to the blood vessel, and is adapted to self-expand upon removal of the constraint; or (b) a constraint and a balloon so that its diameter is smaller than a blood vessel until delivery to the blood vessel, and the balloon is adapted to expand the stent to blood vessel diameter after inflation; or (c) a constraint so that a portion of its diameter is smaller than a blood vessel until delivery to the blood vessel, and is adapted to self-expand upon removal of the constraint; or (d) a constraint and a balloon so that a portion of its diameter is smaller than a blood vessel until delivery to the blood vessel, and the balloon is adapted to expand the stent to blood vessel diameter after inflation; or (e) a combination of (a) and (b); or (f) a combination of (c) and (d); or (g) a combination of (a) and (d); or (h) a combination of (b) and (c).

According to one embodiment, the endovascular stent device comprises a radiopaque marker for positioning the stent in the blood vessel, wherein: a. the radiopaque marker is at the distal end of the stent device; or b. the radiopaque marker is at the proximal end of the stent device; or c. the radiopaque marker is at both the distal end and the proximal end of the stent device; or d. the radiopaque marker is at a distal end of the flow-diverting portion of the stent device; or e. the radiopaque marker is at a proximal end of the flow-diverting portion of the stent device; or f. the radiopaque marker is at both a distal end and a proximal end of the flow-diverting portion of the stent device; or g. the radiopaque marker is at a distal end of a covered portion of the stent device; or h. the radiopaque marker is at a proximal end of a covered portion stent device; or i. the radiopaque marker is at both a distal end and a proximal end of a covered portion of the stent; or j. the radiopaque marker is at a distal end of the flow-diverting portion and at a distal end of a covered portion of the stent device; or k. the radiopaque marker is at a proximal end of the flow-diverting portion and at a proximal end of a covered portion of the stent device; or l. the radiopaque marker is at both distal and proximal ends of the flow-diverting portion and a covered portion of the stent device; or m. the stent device comprises multiple radiopaque markers along the length (l) of the stent device and throughout the circumference of the stent device.

According to another aspect, the described invention provides an endovascular stent device comprising a tubular structure comprising a circumference; wherein a flow-diverting portion of the circumference comprises a flow-diverting material; a length (l) from a proximal end to a distal end ranging in size from about 1 mm to about 800 mm; an inner diameter (d) ranging from about 0.1 mm to about 150 mm; and two or more struts adapted to resist compression spaced at intervals along the length 1 of the stent; wherein (A) the flow-diverting portion of the circumference comprises a length (l') ranging from about 1 mm to about 800 mm; or the flow-diverting portion or portions is/are about 1% to about 100% of the length (l) of the endovascular stent device; (B) the two or more struts are coated with a non-biodegradable hydrogel adapted to expand upon exposure to blood to cover at least) 1% to at least 100% of the length (l') of the flow-diverting portion of the stent; (C) the endovascular stent device comprises (i) a constraint so that its diameter is smaller than a blood vessel until delivery to the blood vessel, and is adapted to self-expand upon removal of the constraint; or (ii) a constraint and a balloon so that its diameter is smaller than a blood vessel until delivery to the blood vessel, and the balloon is adapted to expand the stent to blood vessel diameter after inflation; or (iii) a combination of (i) and (ii); (D) the endovascular stent device (i) is adapted to be retrieved from a blood vessel when about 0% to about 100% of the stent device is deployed in the blood vessel; or (ii) is adapted to be re-positioned in a blood vessel when about 0% to about 100% of the stent device is deployed in the blood vessel; or (iii) is adapted to be re-sheathed in a blood vessel when about 0% to about 100% of the stent device is deployed in the blood vessel; (E) the endovascular stent device is connected to (i) a mechanically detachable site(s) on a wire; or (ii) an electrolytically detachable site(s) on a wire; or (iii) a hydrostatically detachable site(s) on a wire; or (iv) the endovascular stent device is not connected to a wire; and (F) the endovascular stent device is tapered at the proximal end and/or at the distal end or is flared at the proximal end and/or at the distal end.

According to another aspect, the described invention provides an endovascular stent device comprising a tubular structure comprising a circumference; wherein a flow-diverting portion of the circumference is covered by a flow-diverting material; a length (l) from a proximal end to a distal end ranging in size from about 1 mm to about 800 mm; an inner diameter (d) ranging from about 0.1 mm to about 150 mm; wherein (A) the flow-diverting portion of the circumference comprises a length (l') ranging from about 0.1 mm to about 800 mm; or the flow-diverting portion is about 1% to about 100% of the length (l) of the endovascular stent device; (B) the flow-diverting material is polyethylene terephthalate (PET) (Dacron®) or other material coated with a non-biodegradable hydrogel adapted to expand upon exposure to blood to cover 100% of the length (l') of the flow-diverting portion of the stent; (C) the endovascular stent device comprises (i) a constraint so that its diameter is smaller than a blood vessel until delivery to the blood vessel, and is adapted to self-expand upon removal of the constraint; or (ii) a constraint and a balloon so that its diameter is smaller than a blood vessel until delivery to the blood vessel, and the balloon is adapted to expand the stent to blood vessel diameter after inflation; (D) the endovascular stent device (i) is adapted to be retrieved from a blood vessel when about 0% to about 100% of the stent device is deployed in the blood vessel; or (ii) is adapted to be re-positioned in a blood vessel when about 0% to about 100% of the stent device is deployed in the blood vessel; or (iii) is adapted to be re-sheathed in a blood vessel when about 0% to about 100% of the stent device is deployed in the blood vessel; (E) the endovascular stent device is connected to (i) a mechanically detachable site on a wire; or (ii) an electrolytically detachable site on a wire; or (iii) a hydrostatically detachable site on a wire; or (iv) the endovascular stent device is not connected to a wire; and (F) the endovascular stent device is tapered or flared at the proximal end and/or at the distal end.

According to another aspect, the described invention provides an endovascular stent device for intracranial use comprising a tubular structure comprising a circumference; wherein a flow-diverting portion of the circumference is covered by a flow-diverting material that is non-permeable or selectively-permeable; a length (l) from a proximal end to a distal end ranging in size from about 1 mm to about 100 mm; an inner diameter (d) ranging from about 0.1 mm to about 6.5 mm; wherein (A) the flow-diverting portion of the circumference: (i) comprises a length (l') ranging from about 1 mm to about 1000 mm; or (ii) the flow-diverting material covers 100% of the length (l') of the flow-diverting portion of the stent; or (iii) the flow-diverting portion is about 1% to about 100% of the length (l) of the endovascular stent device; and (B) the flow-diverting material is polyethylene terephthalate (PET) (Dacron®); or any other material, with or without outer coating of hydrogel, or any metal struts coated in any portion with any thickness of hydrogel (C) the endovascular stent device comprises (i) a constraint so that its diameter is smaller than a blood vessel until delivery to the blood vessel, and is adapted to self-expand upon removal of the constraint; or (ii) a constraint and a balloon so that its diameter is smaller than a blood vessel until delivery to the blood vessel, and the balloon is adapted to expand the stent to blood vessel diameter after inflation; or (iii) a combination thereof; (D) the endovascular stent device (i) is adapted to be retrieved from a blood vessel when about 0% to about 100% of the stent device is deployed in the blood vessel; or (ii) is adapted to be re-positioned in a blood vessel when about 0% to about 100% of the stent device is deployed in the blood vessel; or (iii) is adapted to be re-sheathed in a blood vessel when about 0% to about 100% of the stent device is deployed in the blood vessel; (E) the endovascular stent device is connected to (i) a mechanically detachable site on a wire; or (ii) an electrolytically detachable site on a wire; or (iii) a hydrostatically detachable site on a wire; or (iv) the endovascular stent device is not connected to a wire; and (F) the endovascular stent device is tapered and/or flared at the proximal end and/or at the distal end and/or any other portion of the stent.

These and other advantages of the invention will be apparent to those of ordinary skill in the art by reference to the following detailed description and the accompanying drawings.

In the various views of the drawings, like reference characters designate like or similar parts.

BRIEF DESCRIPTION OF THE DRAWINGS

FIGS. 9A and 9B show an illustrative embodiment of a constraint 920 adapted to reduce the diameter of the endovascular device 910, a balloon 930 adapted to expand the endovascular device 910 to blood vessel diameter, and a wire 940. FIG. 9A shows the endovascular device with a reduced diameter and the noninflated balloon; FIG. 9B shows the balloon-expanded endovascular device.

DETAILED DESCRIPTION OF THE INVENTION

Glossary

Figure 1:
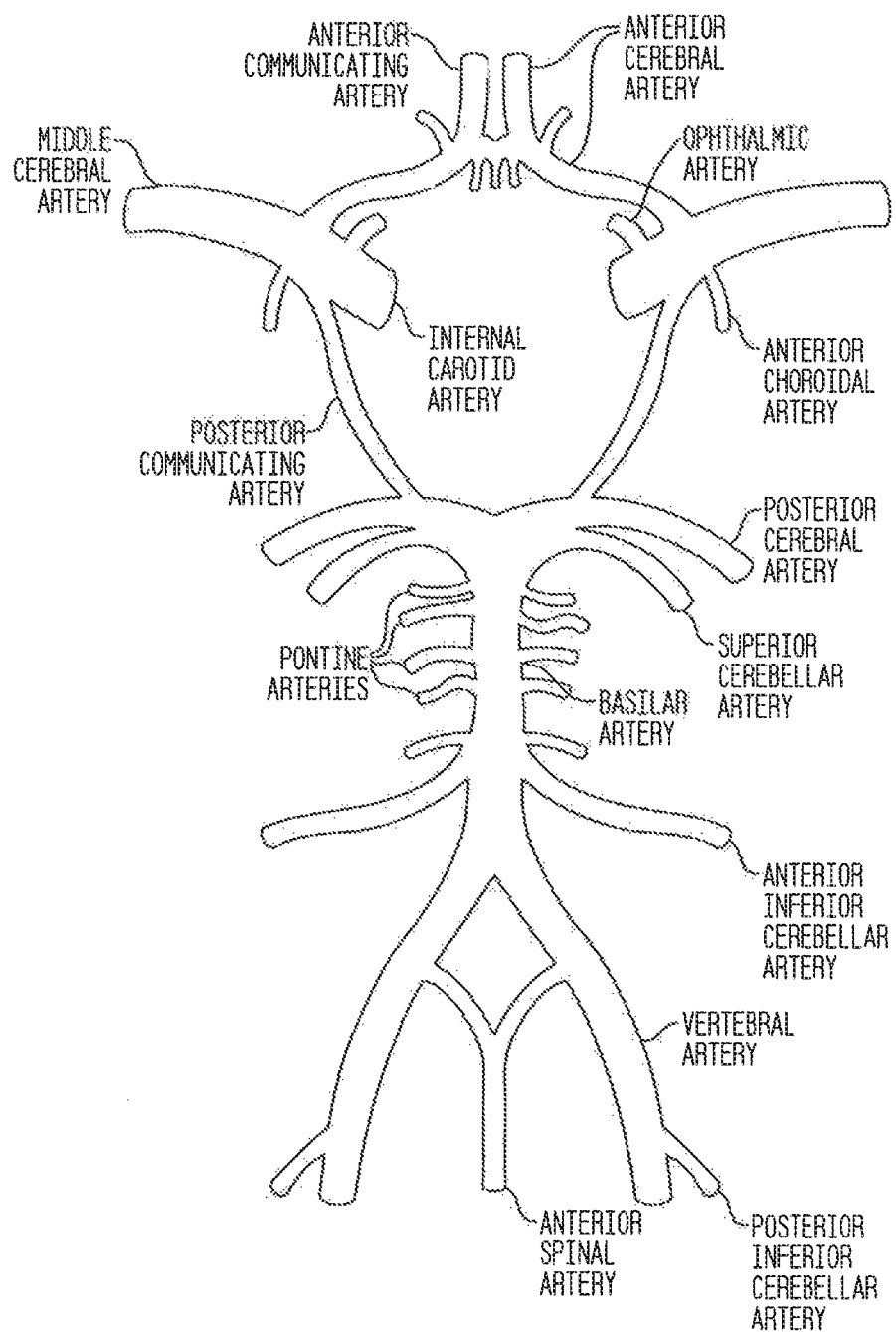
FIG. 1 shows an illustrative view of the cerebral arteries.
Figure 2:
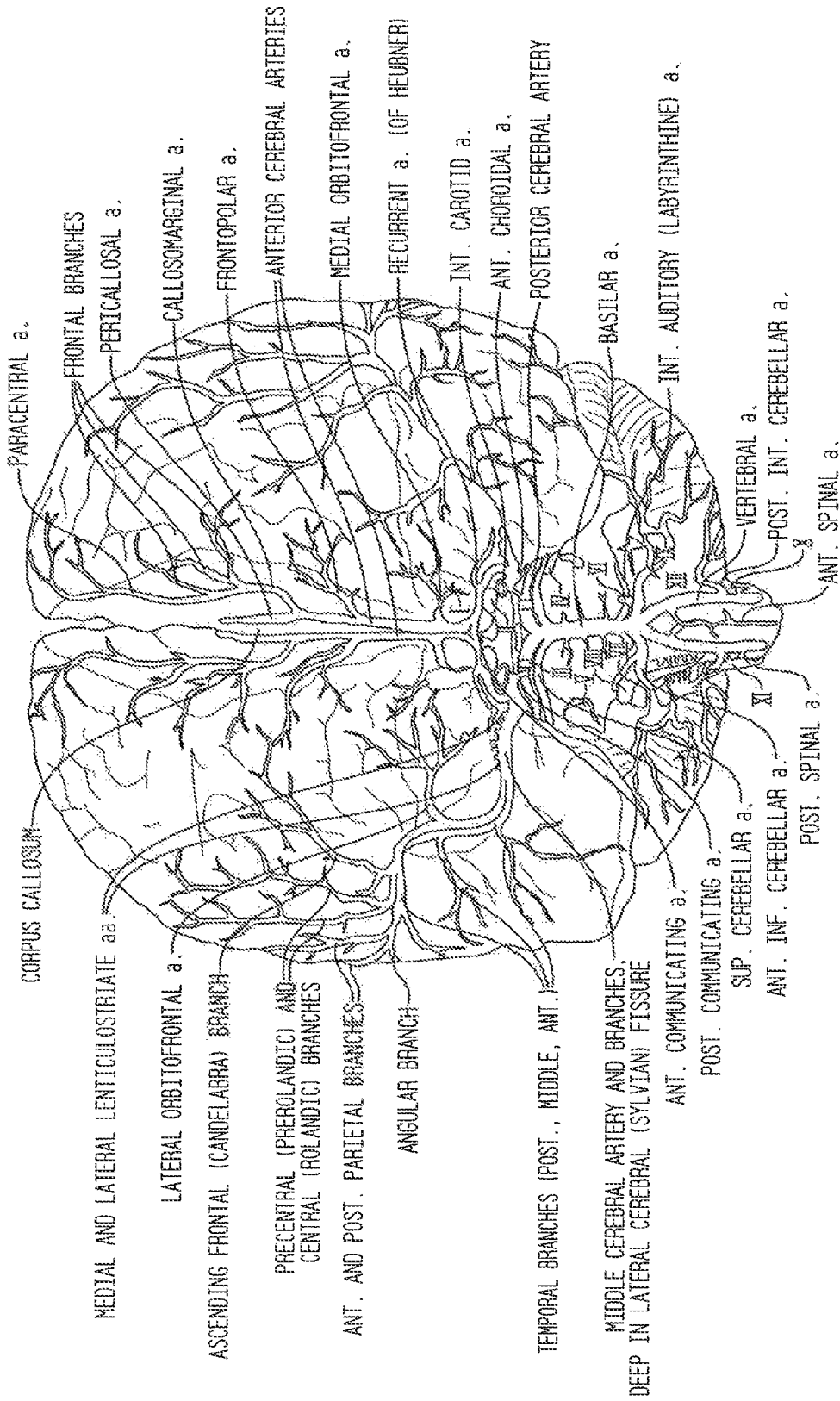
FIG. 2 shows an illustrative view of the cerebral arteries. (from Netter F H. The CIBA Collection of Medical Illustrations: Volumes 1, Nervous System. Vol. 1. Part I. CIBA: USA. 1986. pp. 256).

The terms "acute angle" and "acute angulation" are used interchangeably herein to refer to a sharp, obstructive or abnormal bend (e.g., less than 90 degrees) in an organ, artery, vessel, etc.

Anatomical Terms:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The terms "anomaly", "variation", "abnormality" and "aberration" are used interchangeably herein to refer to a deviation from what is standard, normal or expected. For example, "bovine arch variation" is an anatomical deviation from the most common aortic arch branching pattern in humans. By way of additional example, an anomaly can occur in a blood vessel having tortuosity.

The term "aneurysm", as used herein, refers to a localized widening (dilatation) of an artery, a vein, or the heart. At the point of an aneurysm, there is typically a bulge, where the wall of the blood vessel or organ is weakened and may rupture.

Blood flow in most aneurysms is regular and predictable primarily according to the geometric relationship between the aneurysm and its parent artery. As blood flows within the parent artery with an aneurysm, divergence of blood flow, as occurs at the inlet of the aneurysm, leads to dynamic disturbances, producing increased lateral pressure and retrograde vortices that are easily converted to turbulence. Blood flow proceeds from the parent vessel into the aneurysm at the distal or downstream extent of the aneurysm neck (i.e., the transition from the sac to the parent artery), circulates around the periphery along the aneurysm wall from the neck to the top of the fundus (i.e., aneurysm sac) (downstream to upstream), returning in a type of "isotropic shower" along the aneurysm wall toward the neck region, and exits the closest extent of the aneurysm neck into the parent vessel (See, e.g., Strother C. M. Neuroradiology 1994; 36: 530-536; Moulder P. V. Physiology and biomechanics of aneurysms. In: Kerstein M D, Moulder P V, Webb W R, eds. *Aneurysms*. Baltimore, Md.: Williams & Wilkins; 1983:20).

As flow persists, areas of stagnation or vortices develop within a central zone of the aneurysm. These rotating vortices, formed at the entrance to the aneurysm at each systole (i.e., ventricle contraction) and then circulated around the aneurysm, are caused by the slipstreams or regions of recirculating flow rolling upon themselves when they enter the aneurysm at its downstream wall during systole. The stagnant vortex zone occurs in the center and at the fundus or upper portion of the aneurysm and becomes more pronounced in larger aneurysms. It is this stagnant zone that is believed to promote the formation of thrombi or blood clots, particularly in giant aneurysms (See, e.g., Gobin Y. P. et al. Neuroradiology 1994; 36: 530-536; Hademenos G. J. and Massoud T. F. Stroke 1997; 28: 2067-2077).

The term "aneurysm neck", as used herein, refers to the portion of the blood vessel wall that connects the aneurysm dome or "bulge" to the parent blood vessel.

The term "brain aneurysm", as used herein, refers to a cerebrovascular disease that manifests as a pouching or ballooning of the vessel wall (i.e., vascular dilation). The vascular dilation develops at a diseased site along the arterial wall into a distended sac of stressed and thinned arterial tissue. A fully developed cerebral aneurysm typically ranges in size from a few millimeters to 15 mm but can attain sizes greater than 2.5 cm. If left untreated, the aneurysm may continue to expand until it ruptures, causing hemorrhage, severe neurological complications and deficits, and possibly death (Hademenos G. J. and Massoud T. F. Stroke 1997; 28: 2067-2077; Hademenos G. J. Phys Today 1995; 48: 24-30).

The three main treatment options for a patient suffering from a brain aneurysm are (i) surgical clipping; (ii) endovascular coiling; and (iii) flow diversion. Surgical clipping is an intracranial procedure in which a small metallic clip is placed along the neck of the aneurysm. The clip prevents blood from entering into the aneurysm sac so that it no longer poses a risk for bleeding. The clip remains in place, causing the aneurysm to shrink and permanently scar. Endovascular coiling is a minimally invasive technique in which a catheter is inserted into the femoral artery and navigated through the blood vessels to the vessels of the brain and into the aneurysm. Coils are then packed into the aneurysm to the point where it arises from the blood vessel, thus preventing blood flow from entering the aneurysm. Additional devices, such as a stent or balloon, for example, may be needed to keep the coils in place. Flow diversion is a minimally invasive technique in which a flow diversion device is used to divert blood flow away from an aneurysm by placing a mesh structure, similar to a stent, on the aneurysm neck along the parent artery. A flow diverter can create blood stasis to allow for thrombus formation inside an aneurysm.

The terms "cavernous carotid aneurysm" or "carotid cavernous aneurysm" are used interchangeably herein to refer to an aneurysm of the cavernous segment of the internal carotid artery.

The terms "cavernous carotid fistula" or "carotid cavernous fistula" are used interchangeably herein to refer to an abnormal connection between blood vessels that take blood to and from the brain which are result of trauma, a rupture of a cavernous carotid aneurysm, or a tear in the wall of a weak cavernous internal carotid artery caused by congenital collagen vascular disease.

The term "dissecting vertebral artery aneurysm", as used herein, refers to an aneurysm formed by blood collecting within the walls of the vertebral artery. Most cases result from head or neck trauma, however, this type of aneurysm can arise spontaneously (no previous history of trauma).

The term "aspect ratio", as used herein, refers to the ratio of the width (w) to the height (h) (w:h) of an object.

The term "braid", as used herein, refers to an interlace of three or more strands of a flexible material to form a length.

The term "branch", as used herein, refers to something that extends from or enters into a main body or source; a division or offshoot from a main stem (e.g., blood vessels); one of the primary divisions of a blood vessel.

The term "carotid-cavernous fistula" as used herein refers to a fistulous communication, of spontaneous or traumatic origin, between the cavernous sinus and the traversing carotid artery.

The term "contact", as used herein, refers to a union, junction, touching, association or immediate proximity of surfaces.

The terms "contrast medium" and "contrast agent" are used interchangeably herein to refer to a substance used to enhance the contrast of structures or fluids within the body in medical imaging such as to enhance the visibility of blood vessels.

The term "dimensional stability", as used herein, refers to the property of a material to retain its size and form.

The term "distal", as used herein, refers to the state of being situated away from a point of attachment or origin.

The term "divert" and its other grammatical forms as used herein refers to turning aside or from a path or course.

The term "distensible", as used herein, refers to the ability of an object or material to become larger and rounder due to internal pressure.

The term "endoleak", as used herein, refers to persistent blood flow within an aneurysmal sac following endovascular aneurysm repair (i.e., flow diversion and/or covered stent) procedure.

The term "endoluminal", as used herein, refers to the state of being within a tubular organ or structure (e.g., blood vessel, duct, gastrointestinal tract, etc.) or within a lumen. The term "lumen", as used herein, refers to the inner open space or cavity of a tubular structure.

The term "extensible", as used herein, refers to the ability of an object or material to be stretched or drawn out in length.

The term "filament", as used herein, refers to a very fine thread or threadlike structure, fiber or fibril.

The term "fistula" as used herein refers to an abnormal passage from one epithelial surface to another epithelial surface, or from the lumen of one vessel to the lumen of another vessel that is not normally connected.

The term "flow-diverting", as used herein, refers to the act of re-routing, re-directing or changing the course or direction of blood flow from a parent blood vessel away from an aneurysm.

The term "hemorrhage", as used herein, refers to the escape of blood from a ruptured blood vessel.

Blood vessels typically are structurally adept at withstanding the dynamic quantities required to maintain circulatory function. For reasons that are not entirely understood, the vessel wall can become fatigued and abnormally weak and possibly rupture. With vessel rupture in the brain, hemorrhage occurs with blood seeping into the surrounding brain tissue. As the blood accumulates within the brain, the displaced volume causes the blood, now thrombosed, to ultimately compress the surrounding vessels. The compression of vessels translates into a reduced vessel diameter and a corresponding reduction in flow to surrounding tissue, thereby enlarging the insult (See, e.g., Hademenos G. J. and Massoud T. F. Stroke 1997; 28: 2067-2077).

In the brain, hemorrhage may occur at the brain surface (extraparenchymal), for example, from the rupture of congenital aneurysms at the circle of Willis, causing subarachnoid hemorrhage (SAH). Hemorrhage also may be intraparenchymal, for example, from rupture of vessels damaged by long-standing hypertension, and may cause a blood clot (intracerebral hematoma) within the cerebral hemispheres, in the brain stem, or in the cerebellum. Hemorrhage may be accompanied by ischemia or infarction. The mass effect of an intracerebral hematoma may compromise the blood supply of adjacent brain tissue; or SAH may cause reactive vasospasm of cerebral surface vessels, leading to further ischemic brain damage. Infarcted tissue may also become secondarily hemorrhagic. Among the vascular lesions that can lead to hemorrhagic strokes are aneurysms and arteriovenous malformations (AVMs) (See, e.g., Hademenos G. J. and Massoud T. F. Stroke 1997; 28: 2067-2077).

The term "hydrogel" as used herein refers to a substance resulting in a solid, semisolid, pseudoplastic, or plastic structure containing a necessary aqueous component to produce a gelatinous or jelly-like mass.

The term "interstices", as used herein, refers to small intervening spaces, especially between closely spaced objects; a gap or break in something generally continuous.

The term "introducer", as used herein, refers to an instrument such as a tube or a sheath that is placed within a vein or artery for introduction of a flexible device, for example, a catheter, needle, wire, etc.

The terms "lenticulostriate" and "lenticulostriate artery" are used interchangeably herein to refer to a small perforating artery arising from the anterior part of the circle of Willis and supplying blood to the basal ganglia.

The term "linear density", as used herein, refers to an amount of mass per unit of length.

The term "mesh", as used herein, refers to an interlaced structure or material made of a network of wire or thread.

The term "mesh-free area", as used herein, refers to the closed, mesh-covered area of a stent divided by the total stent area.

The term "occlude", as used herein, refers to the act of stopping, closing up, or obstructing an opening, orifice or passage. By way of example, the endovascular stent device of the described invention can be used to occlude an aneurysm, resulting in blood stasis and thrombus formation within the aneurysm.

The terms "perforator" and "perforating artery" are used interchangeably herein to refer to a blood vessel forming a connection between a deep system and a superficial one.

The term "pore density", as used herein, refers to the number of pores (small apertures) per unit area (pores/mm$^2$).

The term "porosity", as used herein, is a measure of the fraction of small apertures or voids in a material relative to the total area and is usually expressed as a percentage. It also refers to the area of flow-diverting mesh over the neck of an aneurysm relative to the total area of the stent, expressed as a percentage.

The term "proximal", as used herein, refers to the state of being situated next to or nearest the point of attachment or origin.

The term "radial", as used herein, refers to the state of being arranged or having parts arranged in straight lines coming out from a common center.

The term "radial compliance", as used herein, refers to the ability of a stent to bend.

The term "radial pressure", as used herein, refers to the pressure applied to the circumference of a stent.

The term "radial stiffness", as used herein, refers to the change in stent diameter as a function of uniformly applied external radial pressure.

The term "radial strength", as used herein, refers to the pressure at which a stent experiences irrecoverable deformation.

The terms "re-position" and "re-deployment" are used interchangeably herein, to refer to moving from one area to another, adjusting or altering the position of, for example, a stent.

The terms "retrieve" and "recover" are used interchangeably herein to refer to an act of regaining or repossessing into one's grasp or control.

The term "sheath", as used herein, refers to a close fitting cover. By way of example, in an endovascular procedure, a sheath may be a tube placed into an access artery to facilitate catheter exchanges.

The term "re-sheath", as used herein, refers to the act of being returned to a sheath.

The term "steerability", as used herein, refers to an ability to turn or rotate the distal end of a catheter with like-for-like movement of the proximal section or the catheter handle.

The term "string", as used herein, refers to a slender cord or thread.

The term "stroke" or "cerebrovascular accident", as used herein, refers to neurological signs and symptoms, usually focal and acute, which result from diseases involving blood vessels that supply blood to the brain. Strokes are either occlusive (due to closure of a blood vessel) or hemorrhagic (due to bleeding from a vessel). Although most occlusive strokes are due to atherosclerosis and thrombosis, and most hemorrhagic strokes are associated with hypertension or aneurysms, strokes of either type may occur at any age from many causes, including cardiac disease, trauma, infection, neoplasm, blood dyscrasia, vascular malformation, immunological disorder, and exogenous toxins. An ischemia stroke results from a lack of blood supply and oxygen to the brain that occurs when reduced perfusion pressure distal to an abnormal narrowing (stenosis) of a blood vessel is not compensated by autoregulatory dilation of the resistance vessels. When ischemia is sufficiently severe and prolonged, neurons and other cellular elements die. This condition is referred to as "infarction" (See, e.g., Hart R. G. et al., Stroke 1990; 21:1111-1121). Although the consequences of both ischemic and hemorrhagic stroke are similar (i.e., vessel obstruction, resultant reduced blood flow to the brain, neurological deficits and possibly death), the biophysical and hemodynamic mechanisms behind the obstruction of blood flow are different. Biophysical mechanisms for the development of obstructions that ultimately lead to stroke can arise by six distinct processes: atherosclerosis, embolus, thrombus, reduced systemic pressure, hemorrhage, and vasospasm (See, e.g., Hademenos G. J. and Massoud T. F., Stroke 1997; 28: 2067-2077).

The term "strut", as used herein, refers to a structure forming part of a framework to resist compression.

The term "taper", as used herein, refers to the reduction of thickness toward one end; the gradual diminution of width or thickness in an elongated object; i.e., to become more slender toward one end.

The term "thread", as used herein, refers to a cord of a material composed of two or more filaments twisted together.

The term "tortuosity" and other grammatical forms of the term "tortuous" is used herein to refer to a property of a tube, passage or blood vessel (e.g., an artery or a vein) being twisted, crooked or having many turns.

The term "twist", as used herein, refers to a spiral arrangement of fibers around an axis.

The term "twist level", as used herein, refers to an amount of twist per unit length of thread, yarn, cord, etc.

The term "twist factor", as used herein, refers to the product of the twist level and the square root of the linear density.

The term "vasospasm", as used herein, refers to the sudden constriction of a blood vessel, reducing its diameter and flow rate. When bleeding occurs in the subarachnoid space, the arteries in the subarachnoid space can become spastic with a muscular contraction that produces a focal constriction of sufficient severity to cause total occlusion. The length of time that the vessel is contracted during vasospasm varies from hours to days. However, regardless of the duration of vessel constriction, reduction of blood flow induces cerebral ischemia, thought to be reversible within the first 6 hours and irreversible thereafter. It has been shown that vasospasm is maximal between 5 and 10 days after subarachnoid hemorrhage and can occur up to 2 weeks after subarachnoid hemorrhage (See, e.g., Wilkins R. H. Contemp Neurosurg. 1988; 10:1-66; Hademenos G. J. and Massoud T. F. Stroke 1997; 28: 2067-2077).

Figure 3:
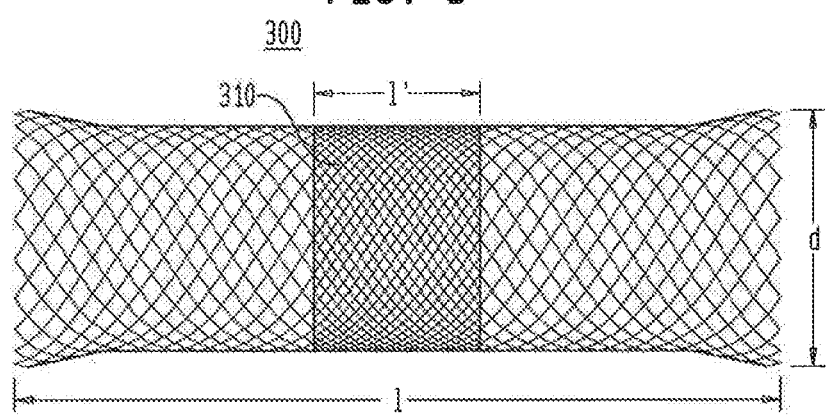
FIG. 3 shows an illustrative embodiment of an endovascular stent device 300. 310 is an illustration of a flow-diverting portion of an endovascular stent device 300 according to the described invention. "d" represents the inner diameter of the endovascular stent; "l" represents the length of the endovascular stent; and "l'" represents the length of the flow-diverting portion of the endovascular stent.

FIG. 3 shows an exemplary and non-limiting example of an embodiment of an endovascular stent device 300 of the described invention. According to one embodiment, FIG. 3 illustrates an endovascular stent device 300 comprising a flow-diverting portion 310. FIG. 3 shows an illustrative embodiment of an endovascular stent device 300. 310 is an illustration of a flow-diverting portion of an endovascular stent device 300 according to the described invention. "d" represents the inner diameter of the endovascular stent; "l" represents the length of the endovascular stent; and "l'" represents the length of the flow-diverting portion of the endovascular stent.

Figure 4:
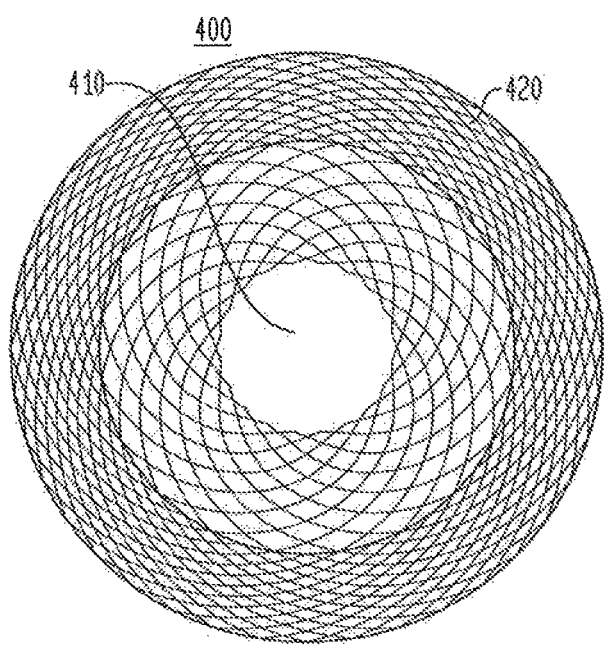
FIG. 4 shows an cross-sectional view of an embodiment of an endovascular stent device 400. 410 shows a cross-sectional view of an embodiment of the inside of the endovascular stent. 420 shows a cross-sectional view of an embodiment of the flow-diverting portion of the endovascular stent.

FIG. 4 shows an cross-sectional view of an embodiment of an endovascular stent device 400. 410 shows a cross-sectional view of an embodiment of the inside of the endovascular stent. 420 shows a cross-sectional view of an embodiment of the flow-diverting portion of the endovascular stent.

According to some embodiments, the stent device 300 is an intracranial endovascular stent device. According to some embodiments, the stent device 300 is a peripheral blood vessel endovascular stent device.

According to some embodiments, the described invention provides an endovascular stent which transitions from a non-flow-diverting portion, to a flow-diverting portion, back to a non-flow-diverting portion. According to some embodiments, the flow-diverting portion is located at a distal portion of the stent. According to some embodiments, the flow-diverting portion is located at a proximal portion of the stent. According to some embodiments, the flow-diverting portion is located in the center of the stent (i.e., equidistant from the distal portion and the proximal portion of the stent). According to some embodiments, the flow-diverting portion covers one side of the endovascular stent. According to some embodiments, the flow-diverting portion completely covers one side of the endovascular stent. According to some embodiments, the flow-diverting portion partially covers one side of the endovascular stent. According to some embodiments, the flow-diverting portion covers one side of the endovascular stent along a single portion of the stent. According to some embodiments, the flow-diverting portion covers one side of the endovascular stent, along multiple portions of the stent, on the same side or different sides of the stent.

According to some embodiments, the endovascular stent of the described invention is in a form of a geometric shape. Such shapes include, but are not limited to, a tube, a coil, a ring, a mesh and a combination thereof.

According to some embodiments, the stent is flexible. According to some embodiments, the stent is rigid.

According to some embodiments, the inner diameter (d) of the stent ranges from about 0.1 mm to about 150 mm. According to some embodiments, the inner diameter (d) of the stent is about 0.1 mm. According to some embodiments, the inner diameter (d) of the stent is about 0.2 mm. According to some embodiments, the inner diameter (d) of the stent is about 0.3 mm. According to some embodiments, the inner diameter (d) of the stent is about 0.4 mm. According to some embodiments, the inner diameter (d) of the stent is about 0.5 mm. According to some embodiments, the inner diameter (d) of the stent is about 0.6 mm. According to some embodiments, the inner diameter (d) of the stent is about 0.7 mm. According to some embodiments, the inner diameter (d) of the stent is about 0.8 mm. According to some embodiments, the inner diameter (d) of the stent is about 0.9 mm. According to some embodiments, the inner diameter (d) of the stent is about 1 mm. According to some embodiments, the inner diameter (d) of the stent is about 2 mm. According to some embodiments, the inner diameter (d) of the stent is about 3 mm. According to some embodiments, the inner diameter (d) of the stent is about 4 mm. According to some embodiments, the inner diameter (d) of the stent is about 5 mm. According to some embodiments, the inner diameter (d) of the stent is about 6 mm. According to some embodiments, the inner diameter (d) of the stent is about 7 mm. According to some embodiments, the inner diameter (d) of the stent is about 8 mm. According to some embodiments, the inner diameter (d) of the stent is about 9 mm. According to some embodiments, the inner diameter (d) of the stent is about 10 mm. According to some embodiments, the inner diameter (d) of the stent is about 11 mm. According to some embodiments, the inner diameter (d) of the stent is about 12 mm. According to some embodiments, the inner diameter (d) of the stent is about 13 mm. According to some embodiments, the inner diameter (d) of the stent is about 14 mm. According to some embodiments, the inner diameter (d) of the stent is about 15 mm. According to some embodiments, the inner diameter (d) of the stent is about 16 mm. According to some embodiments, the inner diameter (d) of the stent is about 17 mm. According to some embodiments, the inner diameter (d) of the stent is about 18 mm. According to some embodiments, the inner diameter (d) of the stent is about 19 mm. According to some embodiments, the inner diameter (d) of the stent is about 20 mm. According to some embodiments, the inner diameter (d) of the stent is about 21 mm. According to some embodiments, the inner diameter (d) of the stent is about 22 mm. According to some embodiments, the inner diameter (d) of the stent is about 23 mm. According to some embodiments, the inner diameter (d) of the stent is about 24 mm. According to some embodiments, the inner diameter (d) of the stent is about 25 mm. According to some embodiments, the inner diameter (d) of the stent is about 26 mm. According to some embodiments, the inner diameter (d) of the stent is about 27 mm. According to some embodiments, the inner diameter (d) of the stent is about 28 mm. According to some embodiments, the inner diameter (d) of the stent is about 29 mm. According to some embodiments, the inner diameter (d) of the stent is about 30 mm. According to some embodiments, the inner diameter (d) of the stent is about 31 mm. According to some embodiments, the inner diameter (d) of the stent is about 32 mm. According to some embodiments, the inner diameter (d) of the stent is about 33 mm. According to some embodiments, the inner diameter (d) of the stent is about 34 mm. According to some embodiments, the inner diameter (d) of the stent is about 35 mm. According to some embodiments, the inner diameter (d) of the stent is about 36 mm. According to some embodiments, the inner diameter (d) of the stent is about 37 mm. According to some embodiments, the inner diameter (d) of the stent is about 38 mm. According to some embodiments, the inner diameter (d) of the stent is about 39 mm. According to some embodiments, the inner diameter (d) of the stent is about 40 mm. According to some embodiments, the inner diameter (d) of the stent is about 41 mm. According to some embodiments, the inner diameter (d) of the stent is about 42 mm. According to some embodiments, the inner diameter (d) of the stent is about 43 mm. According to some embodiments, the inner diameter (d) of the stent is about 44 mm. According to some embodiments, the inner diameter (d) of the stent is about 45 mm. According to some embodiments, the inner diameter (d) of the stent is about 46 mm. According to some embodiments, the inner diameter (d) of the stent is about 47 mm. According to some embodiments, the inner diameter (d) of the stent is about 48 mm. According to some embodiments, the inner diameter (d) of the stent is about 49 mm. According to some embodiments, the inner diameter (d) of the stent is about 50 mm. According to some embodiments, the inner diameter (d) of the stent is about 51 mm. According to some embodiments, the inner diameter (d) of the stent is about 52 mm. According to some embodiments, the inner diameter (d) of the stent is about 53 mm. According to some embodiments, the inner diameter (d) of the stent is about 54 mm. According to some embodiments, the inner diameter (d) of the stent is about 55 mm. According to some embodiments, the inner diameter (d) of the stent is about 56 mm. According to some embodiments, the inner diameter (d) of the stent is about 57 mm. According to some embodiments, the inner diameter (d) of the stent is about 58 mm. According to some embodiments, the inner diameter (d) of the stent is about 59 mm. According to some embodiments, the inner diameter (d) of the stent is about 60 mm. According to some embodiments, the inner diameter (d) of the stent is about 61 mm. According to some embodiments, the inner diameter (d) of the stent is about 62 mm. According to some embodiments, the inner diameter (d) of the stent is about 63 mm. According to some embodiments, the inner diameter (d) of the stent is about 64 mm. According to some embodiments, the inner diameter (d) of the stent is about 65 mm. According to some embodiments, the inner diameter (d) of the stent is about 66 mm. According to some embodiments, the inner diameter (d) of the stent is about 67 mm. According to some embodiments, the inner diameter (d) of the stent is about 68 mm. According to some embodiments, the inner diameter (d) of the stent is about 69 mm. According to some embodiments, the inner diameter (d) of the stent is about 70 mm. According to some embodiments, the inner diameter (d) of the stent is about 71 mm. According to some embodiments, the inner diameter (d) of the stent is about 72 mm. According to some embodiments, the inner diameter (d) of the stent is about 73 mm. According to some embodiments, the inner diameter (d) of the stent is about 74 mm. According to some embodiments, the inner diameter (d) of the stent is about 75 mm. According to some embodiments, the inner diameter (d) of the stent is about 76 mm. According to some embodiments, the inner diameter (d) of the stent is about 77 mm. According to some embodiments, the inner diameter (d) of the stent is about 78 mm. According to some embodiments, the inner diameter (d) of the stent is about 79 mm. According to some embodiments, the inner diameter (d) of the stent is about 80 mm. According to some embodiments, the inner diameter (d) of the stent is about 81 mm. According to some embodiments, the inner diameter (d) of the stent is about 82 mm. According to some embodiments, the inner diameter (d) of the stent is about 83 mm. According to some embodiments, the inner diameter (d) of the stent is about 84 mm. According to some embodiments, the inner diameter (d) of the stent is about 85 mm. According to some embodiments, the inner diameter (d) of the stent is about 86 mm. According to some embodiments, the inner diameter (d) of the stent is about 87 mm. According to some embodiments, the inner diameter (d) of the stent is about 88 mm. According to some embodiments, the inner diameter (d) of the stent is about 89 mm. According to some embodiments, the inner diameter (d) of the stent is about 90 mm. According to some embodiments, the inner diameter (d) of the stent is about 91 mm. According to some embodiments, the inner diameter (d) of the stent is about 92 mm. According to some embodiments, the inner diameter (d) of the stent is about 93 mm. According to some embodiments, the inner diameter (d) of the stent is about 94 mm. According to some embodiments, the inner diameter (d) of the stent is about 95 mm. According to some embodiments, the inner diameter (d) of the stent is about 96 mm. According to some embodiments, the inner diameter (d) of the stent is about 97 mm. According to some embodiments, the inner diameter (d) of the stent is about 98 mm. According to some embodiments, the inner diameter (d) of the stent is about 99 mm. According to some embodiments, the inner diameter (d) of the stent is about 100 mm. According to some embodiments, the inner diameter (d) of the stent is about 101 mm. According to some embodiments, the inner diameter (d) of the stent is about 102 mm. According to some embodiments, the inner diameter (d) of the stent is about 103 mm. According to some embodiments, the inner diameter (d) of the stent is about 104 mm. According to some embodiments, the inner diameter (d) of the stent is about 105 mm. According to some embodiments, the inner diameter (d) of the stent is about 106 mm. According to some embodiments, the inner diameter (d) of the stent is about 107 mm. According to some embodiments, the inner diameter (d) of the stent is about 108 mm. According to some embodiments, the inner diameter (d) of the stent is about 109 mm. According to some embodiments, the inner diameter (d) of the stent is about 110 mm. According to some embodiments, the inner diameter (d) of the stent is about 111 mm. According to some embodiments, the inner diameter (d) of the stent is about 112 mm. According to some embodiments, the inner diameter (d) of the stent is about 113 mm. According to some embodiments, the inner diameter (d) of the stent is about 114 mm. According to some embodiments, the inner diameter (d) of the stent is about 115 mm. According to some embodiments, the inner diameter (d) of the stent is about 116 mm. According to some embodiments, the inner diameter (d) of the stent is about 117 mm. According to some embodiments, the inner diameter (d) of the stent is about 118 mm. According to some embodiments, the inner diameter (d) of the stent is about 119 mm. According to some embodiments, the inner diameter (d) of the stent is about 120 mm. According to some embodiments, the inner diameter (d) of the stent is about 121 mm. According to some embodiments, the inner diameter (d) of the stent is about 122 mm. According to some embodiments, the inner diameter (d) of the stent is about 123 mm. According to some embodiments, the inner diameter (d) of the stent is about 124 mm. According to some embodiments, the inner diameter (d) of the stent is about 125 mm. According to some embodiments, the inner diameter (d) of the stent is about 126 mm. According to some embodiments, the inner diameter (d) of the stent is about 127 mm. According to some embodiments, the inner diameter (d) of the stent is about 128 mm. According to some embodiments, the inner diameter (d) of the stent is about 129 mm. According to some embodiments, the inner diameter (d) of the stent is about 130 mm. According to some embodiments, the inner diameter (d) of the stent is about 131 mm. According to some embodiments, the inner diameter (d) of the stent is about 132 mm. According to some embodiments, the inner diameter (d) of the stent is about 133 mm. According to some embodiments, the inner diameter (d) of the stent is about 134 mm. According to some embodiments, the inner diameter (d) of the stent is about 135 mm. According to some embodiments, the inner diameter (d) of the stent is about 136 mm. According to some embodiments, the inner diameter (d) of the stent is about 137 mm. According to some embodiments, the inner diameter (d) of the stent is about 138 mm. According to some embodiments, the inner diameter (d) of the stent is about 139 mm. According to some embodiments, the inner diameter (d) of the stent is about 140 mm.

According to some embodiments, the inner diameter (d) of the stent is about 141 mm. According to some embodiments, the inner diameter (d) of the stent is about 142 mm. According to some embodiments, the inner diameter (d) of the stent is about 143 mm. According to some embodiments, the inner diameter (d) of the stent is about 144 mm. According to some embodiments, the inner diameter (d) of the stent is about 145 mm. According to some embodiments, the inner diameter (d) of the stent is about 146 mm. According to some embodiments, the inner diameter (d) of the stent is about 147 mm. According to some embodiments, the inner diameter (d) of the stent is about 148 mm. According to some embodiments, the inner diameter (d) of the stent is about 149 mm. According to some embodiments, the inner diameter (d) of the stent is about 150 mm.

According to some embodiments, the length (l) of the stent ranges from about 1 mm to about 800 mm. According to some embodiments, the length (l) of the stent ranges from about 5 mm to about 50 mm. According to some embodiments, the length (l) of the stent ranges from about 12 mm to about 20 mm. According to some embodiments, the length (l) of the stent is about 1 mm. According to some embodiments, the length (l) of the stent is about 2 mm. According to some embodiments, the length (l) of the stent is about 3 mm. According to some embodiments, the length (l) of the stent is about 4 mm. According to some embodiments, the length (l) of the stent is about 5 mm. According to some embodiments, the length (l) of the stent is about 6 mm. According to some embodiments, the length (l) of the stent is about 7 mm. According to some embodiments, the length (l) of the stent is about 8 mm. According to some embodiments, the length (l) of the stent is about 9 mm. According to some embodiments, the length (l) of the stent is about 10 mm. According to some embodiments, the length (l) of the stent is about 11 mm. According to some embodiments, the length (l) of the stent is about 12 mm. According to some embodiments, the length (l) of the stent is about 13 mm. According to some embodiments, the length (l) of the stent is about 14 mm. According to some embodiments, the length (l) of the stent is about 15 mm. According to some embodiments, the length (l) of the stent is about 16 mm. According to some embodiments, the length (l) of the stent is about 17 mm. According to some embodiments, the length (l) of the stent is about 18 mm. According to some embodiments, the length (l) of the stent is about 19 mm. According to some embodiments, the length (l) of the stent is about 20 mm. According to some embodiments, the length (l) of the stent is about 21 mm. According to some embodiments, the length (l) of the stent is about 22 mm. According to some embodiments, the length (l) of the stent is about 23 mm. According to some embodiments, the length (l) of the stent is about 24 mm. According to some embodiments, the length (l) of the stent is about 25 mm. According to some embodiments, the length (l) of the stent is about 26 mm. According to some embodiments, the length (l) of the stent is about 27 mm. According to some embodiments, the length (l) of the stent is about 28 mm. According to some embodiments, the length (l) of the stent is about 29 mm. According to some embodiments, the length (l) of the stent is about 30 mm. According to some embodiments, the length (l) of the stent is about 31 mm. According to some embodiments, the length (l) of the stent is about 32 mm. According to some embodiments, the length (l) of the stent is about 33 mm. According to some embodiments, the length (l) of the stent is about 34 mm. According to some embodiments, the length (l) of the stent is about 35 mm. According to some embodiments, the length (l) of the stent is about 36 mm. According to some embodiments, the length (l) of the stent is about 37 mm. According to some embodiments, the length (l) of the stent is about 38 mm. According to some embodiments, the length (l) of the stent is about 39 mm. According to some embodiments, the length (l) of the stent is about 40 mm. According to some embodiments, the length (l) of the stent is about 41 mm. According to some embodiments, the length (l) of the stent is about 42 mm. According to some embodiments, the length (l) of the stent is about 43 mm. According to some embodiments, the length (l) of the stent is about 44 mm. According to some embodiments, the length (l) of the stent is about 45 mm. According to some embodiments, the length (l) of the stent is about 46 mm. According to some embodiments, the length (l) of the stent is about 47 mm. According to some embodiments, the length (l) of the stent is about 48 mm. According to some embodiments, the length (l) of the stent is about 49 mm. According to some embodiments, the length (l) of the stent is about 50 mm. According to some embodiments, the length (l) of the stent is about 60 mm. According to some embodiments, the length (l) of the stent is about 70 mm. According to some embodiments, the length (l) of the stent is about 80 mm. According to some embodiments, the length (l) of the stent is about 90 mm. According to some embodiments, the length (l) of the stent is about 100 mm. According to some embodiments, the length (l) of the stent is about 110 mm. According to some embodiments, the length (l) of the stent is about 120 mm. According to some embodiments, the length (l) of the stent is about 130 mm. According to some embodiments, the length (l) of the stent is about 140 mm. According to some embodiments, the length (l) of the stent is about 150 mm. According to some embodiments, the length (l) of the stent is about 160 mm. According to some embodiments, the length (l) of the stent is about 170 mm. According to some embodiments, the length (l) of the stent is about 180 mm. According to some embodiments, the length (l) of the stent is about 190 mm. According to some embodiments, the length (l) of the stent is about 200 mm. According to some embodiments, the length (l) of the stent is about 210 mm. According to some embodiments, the length (l) of the stent is about 220 mm. According to some embodiments, the length (l) of the stent is about 230 mm. According to some embodiments, the length (l) of the stent is about 240 mm. According to some embodiments, the length (l) of the stent is about 250 mm. According to some embodiments, the length (l) of the stent is about 260 mm. According to some embodiments, the length (l) of the stent is about 270 mm. According to some embodiments, the length (l) of the stent is about 280 mm. According to some embodiments, the length (l) of the stent is about 290 mm. According to some embodiments, the length (l) of the stent is about 300 mm. According to some embodiments, the length (l) of the stent is about 310 mm. According to some embodiments, the length (l) of the stent is about 320 mm. According to some embodiments, the length (l) of the stent is about 330 mm. According to some embodiments, the length (l) of the stent is about 340 mm. According to some embodiments, the length (l) of the stent is about 350 mm. According to some embodiments, the length (l) of the stent is about 360 mm. According to some embodiments, the length (l) of the stent is about 370 mm. According to some embodiments, the length (l) of the stent is about 380 mm. According to some embodiments, the length (l) of the stent is about 390 mm. According to some embodiments, the length (l) of the stent is about 400 mm. According to some embodiments, the length (l) of the stent is about 410 mm. According to some embodiments, the length (l) of the stent is about 420 mm. According to some embodiments, the length (l) of the stent is about 430 mm. According to some embodiments, the length (l) of the stent is about 440 mm. According to some embodiments, the length (l) of the stent is about 450 mm. According to some embodiments, the length (l) of the stent is about 460 mm. According to some embodiments, the length (l) of the stent is about 470 mm. According to some embodiments, the length (l) of the stent is about 480 mm. According to some embodiments, the length (l) of the stent is about 490 mm. According to some embodiments, the length (l) of the stent is about 500 mm. According to some embodiments, the length (l) of the stent is about 510 mm. According to some embodiments, the length (l) of the stent is about 520 mm. According to some embodiments, the length (l) of the stent is about 530 mm. According to some embodiments, the length (l) of the stent is about 540 mm. According to some embodiments, the length (l) of the stent is about 550 mm. According to some embodiments, the length (l) of the stent is about 560 mm. According to some embodiments, the length (l) of the stent is about 570 mm. According to some embodiments, the length (l) of the stent is about 580 mm. According to some embodiments, the length (l) of the stent is about 590 mm. According to some embodiments, the length (l) of the stent is about 600 mm. According to some embodiments, the length (l) of the stent is about 610 mm. According to some embodiments, the length (l) of the stent is about 620 mm. According to some embodiments, the length (l) of the stent is about 630 mm. According to some embodiments, the length (l) of the stent is about 640 mm. According to some embodiments, the length (l) of the stent is about 650 mm. According to some embodiments, the length (l) of the stent is about 660 mm. According to some embodiments, the length (l) of the stent is about 670 mm. According to some embodiments, the length (l) of the stent is about 680 mm. According to some embodiments, the length (l) of the stent is about 690 mm. According to some embodiments, the length (l) of the stent is about 700 mm. According to some embodiments, the length (l) of the stent is about 710 mm. According to some embodiments, the length (l) of the stent is about 720 mm. According to some embodiments, the length (l) of the stent is about 730 mm. According to some embodiments, the length (l) of the stent is about 740 mm. According to some embodiments, the length (l) of the stent is about 750 mm. According to some embodiments, the length (l) of the stent is about 760 mm. According to some embodiments, the length (l) of the stent is about 770 mm. According to some embodiments, the length (l) of the stent is about 780 mm. According to some embodiments, the length (l) of the stent is about 790 mm. According to some embodiments, the length (l) of the stent is about 800 mm.

According to some embodiments, the length (l') of the flow-diverting portion of the endovascular stent ranges from about 1 mm to about 800 mm. According to some embodiments, the length (l') of the flow-diverting portion ranges from about 5 mm to about 10 mm. According to some embodiments, the length (l') of the flow-diverting portion is about 1 mm. According to some embodiments, the length (l') of the flow-diverting portion is about 2 mm. According to some embodiments, the length (l') of the flow-diverting portion is about 3 mm. According to some embodiments, the length (l') of the flow-diverting portion is about 4 mm. According to some embodiments, the length (l') of the flow-diverting portion is about 5 mm. According to some embodiments, the length (l') of the flow-diverting portion is about 6 mm. According to some embodiments, the length (l') of the flow-diverting portion is about 7 mm. According to some embodiments, the length (l') of the covered portion is about 8 mm. According to some embodiments, the length (l') of the flow-diverting portion is about 9 mm. According to some embodiments, the length (l') of the flow-diverting portion is about 10 mm. According to some embodiments, the length (l') of the flow-diverting portion is about 11 mm. According to some embodiments, the length (l') of the flow-diverting portion is about 12 mm. According to some embodiments, the length (l') of the flow-diverting portion is about 13 mm. According to some embodiments, the length (l') of the flow-diverting portion is about 14 mm. According to some embodiments, the length (l') of the flow-diverting portion is about 15 mm. According to some embodiments, the length (l') of the flow-diverting portion is about 16 mm. According to some embodiments, the length (l') of the flow-diverting portion is about 17 mm. According to some embodiments, the length (l') of the flow-diverting portion is about 18 mm. According to some embodiments, the length (l') of the flow-diverting portion is about 19 mm. According to some embodiments, the length (l') of the flow-diverting portion is about 20 mm. According to some embodiments, the length (l') of the flow-diverting portion is about 21 mm. According to some embodiments, the length (l') of the flow-diverting portion is about 22 mm. According to some embodiments, the length (l') of the flow-diverting portion is about 23 mm. According to some embodiments, the length (l') of the flow-diverting portion is about 24 mm. According to some embodiments, the length (l') of the flow-diverting portion is about 25 mm. According to some embodiments, the length (l') of the flow-diverting portion is about 26 mm. According to some embodiments, the length (l') of the flow-diverting portion is about 27 mm. According to some embodiments, the length (l') of the flow-diverting portion is about 28 mm. According to some embodiments, the length (l') of the flow-diverting portion is about 29 mm. According to some embodiments, the length (l') of the flow-diverting portion is about 30 mm. According to some embodiments, the length (l') of the flow-diverting portion is about 31 mm. According to some embodiments, the length (l') of the flow-diverting portion is about 32 mm. According to some embodiments, the length (l') of the flow-diverting portion is about 33 mm. According to some embodiments, the length (l') of the flow-diverting portion is about 34 mm. According to some embodiments, the length (l') of the flow-diverting portion is about 35 mm. According to some embodiments, the length (l') of the flow-diverting portion is about 36 mm. According to some embodiments, the length (l') of the flow-diverting portion is about 37 mm. According to some embodiments, the length (l') of the flow-diverting portion is about 38 mm. According to some embodiments, the length (l') of the flow-diverting portion is about 39 mm. According to some embodiments, the length (l') of the flow-diverting portion is about 40 mm. According to some embodiments, the length (l') of the flow-diverting portion is about 41 mm. According to some embodiments, the length (l') of the flow-diverting portion is about 42 mm. According to some embodiments, the length (l') of the flow-diverting portion is about 43 mm. According to some embodiments, the length (l') of the flow-diverting portion is about 44 mm. According to some embodiments, the length (l') of the flow-diverting portion is about 45 mm. According to some embodiments, the length (l') of the flow-diverting portion is about 46 mm. According to some embodiments, the length (l') of the flow-diverting portion is about 47 mm. According to some embodiments, the length (l') of the flow-diverting portion is about 48 mm. According to some embodiments, the length (l') of the flow-diverting portion is about 49 mm. According to some embodiments, the length (l') of the flow-diverting portion is about 50 mm. According to some embodiments, the length (l') of the flow-diverting portion is about 60 mm. According to some embodiments, the length (l') of the flow-diverting portion is about 70 mm. According to some embodiments, the length (l') of the flow-diverting portion is about 80 mm. According to some embodiments, the length (l') of the flow-diverting portion is about 90 mm. According to some embodiments, the length (l') of the flow-diverting portion is about 100 mm. According to some embodiments, the length (l') of the flow-diverting portion is about 110 mm. According to some embodiments, the length (l') of the flow-diverting portion is about 120 mm. According to some embodiments, the length (l') of the flow-diverting portion is about 130 mm. According to some embodiments, the length (l') of the flow-diverting portion is about 140 mm. According to some embodiments, the length (l') of the flow-diverting portion is about 150 mm. According to some embodiments, the length (l') of the flow-diverting portion is about 160 mm. According to some embodiments, the length (l') of the flow-diverting portion is about 170 mm. According to some embodiments, the length (l') of the flow-diverting portion is about 180 mm. According to some embodiments, the length (l') of the flow-diverting portion is about 190 mm. According to some embodiments, the length (l') of the flow-diverting portion is about 200 mm. According to some embodiments, the length (l') of the flow-diverting portion is about 210 mm. According to some embodiments, the length (l') of the flow-diverting portion is about 220 mm. According to some embodiments, the length (l') of the flow-diverting portion is about 230 mm. According to some embodiments, the length (l') of the flow-diverting portion is about 240 mm. According to some embodiments, the length (l') of the flow-diverting portion is about 250 mm. According to some embodiments, the length (l') of the flow-diverting portion is about 260 mm. According to some embodiments, the length (l') of the flow-diverting portion is about 270 mm. According to some embodiments, the length (l') of the flow-diverting portion is about 280 mm. According to some embodiments, the length (l') of the flow-diverting portion is about 290 mm. According to some embodiments, the length (l') of the flow-diverting portion is about 300 mm. According to some embodiments, the length (l') of the flow-diverting portion is about 310 mm. According to some embodiments, the length (l') of the flow-diverting portion is about 320 mm. According to some embodiments, the length (l') of the flow-diverting portion is about 330 mm. According to some embodiments, the length (l') of the flow-diverting portion is about 340 mm. According to some embodiments, the length (l') of the flow-diverting portion is about 350 mm. According to some embodiments, the length (l') of the flow-diverting portion is about 360 mm. According to some embodiments, the length (l') of the flow-diverting portion is about 370 mm. According to some embodiments, the length (l') of the flow-diverting portion is about 380 mm. According to some embodiments, the length (l') of the flow-diverting portion is about 390 mm. According to some embodiments, the length (l') of the flow-diverting portion is about 400 mm. According to some embodiments, the length (l') of the flow-diverting portion is about 410 mm. According to some embodiments, the length (l') of the flow-diverting portion is about 420 mm. According to some embodiments, the length (l') of the flow-diverting portion is about 430 mm. According to some embodiments, the length (l') of the flow-diverting portion is about 440 mm. According to some embodiments, the length (l') of the flow-diverting portion is about 450 mm. According to some embodiments, the length (l') of the flow-diverting portion is about 460 mm. According to some embodiments, the length (l') of the flow-diverting portion is about 470 mm. According to some embodiments, the length (l') of the flow-diverting portion is about 480 mm. According to some embodiments, the length (l') of the flow-diverting portion is about 490 mm. According to some embodiments, the length (l') of the flow-diverting portion is about 500 mm. According to some embodiments, the length (l') of the flow-diverting portion is about 510 mm. According to some embodiments, the length (l') of the flow-diverting portion is about 520 mm. According to some embodiments, the length (l') of the flow-diverting portion is about 530 mm. According to some embodiments, the length (l') of the flow-diverting portion is about 540 mm. According to some embodiments, the length (l') of the flow-diverting portion is about 550 mm. According to some embodiments, the length (l') of the flow-diverting portion is about 560 mm. According to some embodiments, the length (l') of the flow-diverting portion is about 570 mm. According to some embodiments, the length (l') of the flow-diverting portion is about 580 mm. According to some embodiments, the length (l') of the flow-diverting portion is about 590 mm. According to some embodiments, the length (l') of the flow-diverting portion is about 600 mm. According to some embodiments, the length (l') of the flow-diverting portion is about 610 mm. According to some embodiments, the length (l') of the flow-diverting portion is about 620 mm. According to some embodiments, the length (l') of the flow-diverting portion is about 630 mm. According to some embodiments, the length (l') of the flow-diverting portion is about 640 mm. According to some embodiments, the length (l') of the flow-diverting portion is about 650 mm. According to some embodiments, the length (l') of the flow-diverting portion is about 660 mm. According to some embodiments, the length (l') of the flow-diverting portion is about 670 mm. According to some embodiments, the length (l') of the flow-diverting portion is about 680 mm. According to some embodiments, the length (l') of the flow-diverting portion is about 690 mm. According to some embodiments, the length (l') of the flow-diverting portion is about 700 mm. According to some embodiments, the length (l') of the flow-diverting portion is about 710 mm. According to some embodiments, the length (l') of the flow-diverting portion is about 720 mm. According to some embodiments, the length (l') of the flow-diverting portion is about 730 mm. According to some embodiments, the length (l') of the flow-diverting portion is about 740 mm. According to some embodiments, the length (l') of the flow-diverting portion is about 750 mm. According to some embodiments, the length (l') of the flow-diverting portion is about 760 mm. According to some embodiments, the length (l') of the flow-diverting portion is about 770 mm. According to some embodiments, the length (l') of the flow-diverting portion is about 780 mm. According to some embodiments, the length (l') of the flow-diverting portion is about 790 mm. According to some embodiments, the length (l') of the flow-diverting portion is about 800 mm.

According to some embodiments, the length (l') of the flow-diverting portion covers at least 1% to at least 100% of the length (l) of the stent. According to some embodiments, the length (l') of the flow-diverting portion covers at least 1% of the length (l) of the stent. According to some embodiments, the length (l') of the flow-diverting portion covers at least 2% of the length (l) of the stent. According to some embodiments, the length (l') of the flow-diverting portion covers at least 3% of the length (l) of the stent. According to some embodiments, the length (l') of the flow-diverting portion covers at least 4% of the length (l) of the stent. According to some embodiments, the length (l') of the flow-diverting portion covers at least 5% of the length (l) of the stent. According to some embodiments, the length (l') of the flow-diverting portion covers at least 6% of the length (l) of the stent. According to some embodiments, the length (l') of the flow-diverting portion covers at least 7% of the length (l) of the stent. According to some embodiments, the length (l') of the flow-diverting portion covers at least 8% of the length (l) of the stent. According to some embodiments, the length (l') of the flow-diverting portion covers at least 9% of the length (l) of the stent. According to some embodiments, the length (l') of the flow-diverting portion covers at least 10% of the length (l) of the stent. According to some embodiments, the length (l') of the flow-diverting portion covers at least 11% of the length (l) of the stent. According to some embodiments, the length (l') of the flow-diverting portion covers at least 12% of the length (l) of the stent. According to some embodiments, the length (l') of the flow-diverting portion covers at least 13% of the length (l) of the stent. According to some embodiments, the length (l') of the flow-diverting portion covers at least 14% of the length (l) of the stent. According to some embodiments, the length (l') of the flow-diverting portion covers at least 15% of the length (l) of the stent. According to some embodiments, the length (l') of the flow-diverting portion covers at least 16% of the length (l) of the stent. According to some embodiments, the length (l') of the flow-diverting portion covers at least 17% of the length (l) of the stent. According to some embodiments, the length (l') of the flow-diverting portion covers at least 18% of the length (l) of the stent. According to some embodiments, the length (l') of the flow-diverting portion covers at least 19% of the length (l) of the stent. According to some embodiments, the length (l') of the flow-diverting portion covers at least 20% of the length (l) of the stent. According to some embodiments, the length (l') of the flow-diverting portion covers at least 21% of the length (l) of the stent. According to some embodiments, the length (l') of the flow-diverting portion covers at least 22% of the length (l) of the stent. According to some embodiments, the length (l') of the flow-diverting portion covers at least 23% of the length (l) of the stent. According to some embodiments, the length (l') of the flow-diverting portion covers at least 24% of the length (l) of the stent. According to some embodiments, the length (l') of the flow-diverting portion covers at least 25% of the length (l) of the stent. According to some embodiments, the length (l') of the flow-diverting portion covers at least 26% of the length (l) of the stent. According to some embodiments, the length (l') of the flow-diverting portion covers at least 27% of the length (l) of the stent. According to some embodiments, the length (l') of the flow-diverting portion covers at least 28% of the length (l) of the stent. According to some embodiments, the length (l') of the flow-diverting portion covers at least 29% of the length (l) of the stent. According to some embodiments, the length (l') of the flow-diverting portion covers at least 30% of the length (l) of the stent. According to some embodiments, the length (l') of the flow-diverting portion covers at least 31% of the length (l) of the stent. According to some embodiments, the length (l') of the flow-diverting portion covers at least 32% of the length (l) of the stent. According to some embodiments, the length (l') of the flow-diverting portion covers at least 33% of the length (l) of the stent. According to some embodiments, the length (l') of the flow-diverting portion covers at least 34% of the length (l) of the stent. According to some embodiments, the length (l') of the flow-diverting portion covers at least 35% of the length (l) of the stent. According to some embodiments, the length (l') of the flow-diverting portion covers at least 36% of the length (l) of the stent. According to some embodiments, the length (l') of the flow-diverting portion covers at least 37% of the length (l) of the stent. According to some embodiments, the length (l') of the flow-diverting portion covers at least 38% of the length (l) of the stent. According to some embodiments, the length (l') of the flow-diverting portion covers at least 39% of the length (l) of the stent. According to some embodiments, the length (l') of the flow-diverting portion covers at least 40% of the length (l) of the stent. According to some embodiments, the length (l') of the flow-diverting portion covers at least 41% of the length (l) of the stent. According to some embodiments, the length (l') of the flow-diverting portion covers at least 42% of the length (l) of the stent. According to some embodiments, the length (l') of the flow-diverting portion covers at least 43% of the length (l) of the stent. According to some embodiments, the length (l') of the flow-diverting portion covers at least 44% of the length (l) of the stent. According to some embodiments, the length (l') of the flow-diverting portion covers at least 45% of the length (l) of the stent. According to some embodiments, the length (l') of the flow-diverting portion covers at least 46% of the length (l) of the stent. According to some embodiments, the length (l') of the flow-diverting portion covers at least 47% of the length (l) of the stent. According to some embodiments, the length (l') of the flow-diverting portion covers at least 48% of the length (l) of the stent. According to some embodiments, the length (l') of the flow-diverting portion covers at least 49% of the length (l) of the stent. According to some embodiments, the length (l') of the flow-diverting portion covers at least 50% of the length (l) of the stent. According to some embodiments, the length (l') of the flow-diverting portion covers at least 51% of the length (l) of the stent. According to some embodiments, the length (l') of the flow-diverting portion covers at least 52% of the length (l) of the stent. According to some embodiments, the length (l') of the flow-diverting portion covers at least 53% of the length (l) of the stent. According to some embodiments, the length (l') of the flow-diverting portion covers at least 54% of the length (l) of the stent. According to some embodiments, the length (l') of the flow-diverting portion covers at least 55% of the length (l) of the stent. According to some embodiments, the length (l') of the flow-diverting portion covers at least 56% of the length (l) of the stent. According to some embodiments, the length (l') of the flow-diverting portion covers at least 57% of the length (l) of the stent. According to some embodiments, the length (l') of the flow-diverting portion covers at least 58% of the length (l) of the stent. According to some embodiments, the length (l') of the flow-diverting portion covers at least 59% of the length (l) of the stent. According to some embodiments, the length (l') of the flow-diverting portion covers at least 60% of the length (l) of the stent. According to some embodiments, the length (l') of the flow-diverting portion covers at least 61% of the length (l) of the stent. According to some embodiments, the length (l') of the flow-diverting portion covers at least 62% of the length (l) of the stent. According to some embodiments, the length (l') of the flow-diverting portion covers at least 63% of the length (l) of the stent. According to some embodiments, the length (l') of the flow-diverting portion covers at least 64% of the length (l) of the stent. According to some embodiments, the length (l') of the flow-diverting portion covers at least 65% of the length (l) of the stent. According to some embodiments, the length (l') of the flow-diverting portion covers at least 66% of the length (l) of the stent. According to some embodiments, the length (l') of the flow-diverting portion covers at least 67% of the length (l) of the stent. According to some embodiments, the length (l') of the flow-diverting portion covers at least 68% of the length (l) of the stent. According to some embodiments, the length (l') of the flow-diverting portion covers at least 69% of the length (l) of the stent. According to some embodiments, the length (l') of the flow-diverting portion covers at least 70% of the length (l) of the stent. According to some embodiments, the length (l') of the flow-diverting portion covers at least 71% of the length (l) of the stent. According to some embodiments, the length (l') of the flow-diverting portion covers at least 72% of the length (l) of the stent. According to some embodiments, the length (l') of the flow-diverting portion covers at least 73% of the length (l) of the stent. According to some embodiments, the length (l') of the flow-diverting portion covers at least 74% of the length (l) of the stent. According to some embodiments, the length (l') of the flow-diverting portion covers at least 75% of the length (l) of the stent. According to some embodiments, the length (l') of the flow-diverting portion covers at least 76% of the length (l) of the stent. According to some embodiments, the length (l') of the flow-diverting portion covers at least 77% of the length (l) of the stent. According to some embodiments, the length (l') of the flow-diverting portion covers at least 78% of the length (l) of the stent. According to some embodiments, the length (l') of the flow-diverting portion covers at least 79% of the length (l) of the stent. According to some embodiments, the length (l') of the flow-diverting portion covers at least 80% of the length (l) of the stent. According to some embodiments, the length (l') of the flow-diverting portion covers at least 81% of the length (l) of the stent. According to some embodiments, the length (l') of the flow-diverting portion covers at least 82% of the length (l) of the stent. According to some embodiments, the length (l') of the flow-diverting portion covers at least 83% of the length (l) of the stent. According to some embodiments, the length (l') of the flow-diverting portion covers at least 84% of the length (l) of the stent. According to some embodiments, the length (l') of the flow-diverting portion covers at least 85% of the length (l) of the stent. According to some embodiments, the length (l') of the flow-diverting portion covers at least 86% of the length (l) of the stent. According to some embodiments, the length (l') of the flow-diverting portion covers at least 87% of the length (l) of the stent. According to some embodiments, the length (l') of the flow-diverting portion covers at least 88% of the length (l) of the stent. According to some embodiments, the length (l') of the flow-diverting portion covers at least 89% of the length (l) of the stent. According to some embodiments, the length (l') of the flow-diverting portion covers at least 90% of the length (l) of the stent. According to some embodiments, the length (l') of the flow-diverting portion covers at least 91% of the length (l) of the stent. According to some embodiments, the length (l') of the flow-diverting portion covers at least 92% of the length (l) of the stent. According to some embodiments, the length (l') of the flow-diverting portion covers at least 93% of the length (l) of the stent. According to some embodiments, the length (l') of the flow-diverting portion covers at least 94% of the length (l) of the stent. According to some embodiments, the length (l') of the flow-diverting portion covers at least 95% of the length (l) of the stent. According to some embodiments, the length (l') of the flow-diverting portion covers at least 96% of the length (l) of the stent. According to some embodiments, the length (l') of the flow-diverting portion covers at least 97% of the length (l) of the stent. According to some embodiments, the length (l') of the flow-diverting portion covers at least 98% of the length (l) of the stent. According to some embodiments, the length (l') of the flow-diverting portion covers at least 99% of the length (l) of the stent. According to some embodiments, the length (l') of the flow-diverting portion covers at least 100% of the length (l) of the stent.

According to some embodiments, the flow-diverting portion covers the entire circumference of the stent. According to some embodiments, the flow-diverting portion partially covers the circumference of the stent. According to some embodiments, the circumference of the stent covered by the flow-diverting portion ranges from about 1% to about 100% of the total circumference of the stent. According to some embodiments, the circumference of the stent covered by the flow-diverting portion is about 1%. According to some embodiments, the circumference of the stent covered by the flow-diverting portion is about 2%. According to some embodiments, the circumference of the stent covered by the flow-diverting portion is about 3%. According to some embodiments, the circumference of the stent covered by the flow-diverting portion is about 4%. According to some embodiments, the circumference of the stent covered by the flow-diverting portion is about 5%. According to some embodiments, the circumference of the stent covered by the flow-diverting portion is about 6%. According to some embodiments, the circumference of the stent covered by the flow-diverting portion is about 7%. According to some embodiments, the circumference of the stent covered by the flow-diverting portion is about 8%. According to some embodiments, the circumference of the stent covered by the flow-diverting portion is about 9%. According to some embodiments, the circumference of the stent covered by the flow-diverting portion is about 10%. According to some embodiments, the circumference of the stent covered by the flow-diverting portion is about 11%. According to some embodiments, the circumference of the stent covered by the flow-diverting portion is about 12%. According to some embodiments, the circumference of the stent covered by the flow-diverting portion is about 13%. According to some embodiments, the circumference of the stent covered by the flow-diverting portion is about 14%. According to some embodiments, the circumference of the stent covered by the flow-diverting portion is about 15%. According to some embodiments, the circumference of the stent covered by the flow-diverting portion is about 16%. According to some embodiments, the circumference of the stent covered by the flow-diverting portion is about 17%. According to some embodiments, the circumference of the stent covered by the flow-diverting portion is about 18%. According to some embodiments, the circumference of the stent covered by the flow-diverting portion is about 19%. According to some embodiments, the circumference of the stent covered by the flow-diverting portion is about 20%. According to some embodiments, the circumference of the stent covered by the flow-diverting portion is about 21%. According to some embodiments, the circumference of the stent covered by the flow-diverting portion is about 22%. According to some embodiments, the circumference of the stent covered by the flow-diverting portion is about 23%. According to some embodiments, the circumference of the stent covered by the flow-diverting portion is about 24%. According to some embodiments, the circumference of the stent covered by the flow-diverting portion is about 25%. According to some embodiments, the circumference of the stent covered by the flow-diverting portion is about 26%. According to some embodiments, the circumference of the stent covered by the flow-diverting portion is about 27%. According to some embodiments, the circumference of the stent covered by the flow-diverting portion is about 28%. According to some embodiments, the circumference of the stent covered by the flow-diverting portion is about 29%. According to some embodiments, the circumference of the stent covered by the flow-diverting portion is about 30%. According to some embodiments, the circumference of the stent covered by the flow-diverting portion is about 31%. According to some embodiments, the circumference of the stent covered by the flow-diverting portion is about 32%. According to some embodiments, the circumference of the stent covered by the flow-diverting portion is about 33%. According to some embodiments, the circumference of the stent covered by the flow-diverting portion is about 34%. According to some embodiments, the circumference of the stent covered by the flow-diverting portion is about 35%. According to some embodiments, the circumference of the stent covered by the flow-diverting portion is about 36%. According to some embodiments, the circumference of the stent covered by the flow-diverting portion is about 37%. According to some embodiments, the circumference of the stent covered by the flow-diverting portion is about 38%. According to some embodiments, the circumference of the stent covered by the flow-diverting portion is about 39%. According to some embodiments, the circumference of the stent covered by the flow-diverting portion is about 40%. According to some embodiments, the circumference of the stent covered by the flow-diverting portion is about 41%. According to some embodiments, the circumference of the stent covered by the flow-diverting portion is about 42%. According to some embodiments, the circumference of the stent covered by the flow-diverting portion is about 43%. According to some embodiments, the circumference of the stent covered by the flow-diverting portion is about 44%. According to some embodiments, the circumference of the stent covered by the flow-diverting portion is about 45%. According to some embodiments, the circumference of the stent covered by the flow-diverting portion is about 46%. According to some embodiments, the circumference of the stent covered by the flow-diverting portion is about 47%. According to some embodiments, the circumference of the stent covered by the flow-diverting portion is about 48%. According to some embodiments, the circumference of the stent covered by the flow-diverting portion is about 49%. According to some embodiments, the circumference of the stent covered by the flow-diverting portion is about 50%. According to some embodiments, the circumference of the stent covered by the flow-diverting portion is about 51%. According to some embodiments, the circumference of the stent covered by the flow-diverting portion is about 52%. According to some embodiments, the circumference of the stent covered by the flow-diverting portion is about 53%. According to some embodiments, the circumference of the stent covered by the flow-diverting portion is about 54%. According to some embodiments, the circumference of the stent covered by the flow-diverting portion is about 55%. According to some embodiments, the circumference of the stent covered by the flow-diverting portion is about 56%. According to some embodiments, the circumference of the stent covered by the flow-diverting portion is about 57%. According to some embodiments, the circumference of the stent covered by the flow-diverting portion is about 58%. According to some embodiments, the circumference of the stent covered by the flow-diverting portion is about 59%. According to some embodiments, the circumference of the stent covered by the flow-diverting portion is about 60%. According to some embodiments, the circumference of the stent covered by the flow-diverting portion is about 61%. According to some embodiments, the circumference of the stent covered by the flow-diverting portion is about 62%. According to some embodiments, the circumference of the stent covered by the flow-diverting portion is about 63%. According to some embodiments, the circumference of the stent covered by the flow-diverting portion is about 64%. According to some embodiments, the circumference of the stent covered by the flow-diverting portion is about 65%. According to some embodiments, the circumference of the stent covered by the flow-diverting portion is about 66%. According to some embodiments, the circumference of the stent covered by the flow-diverting portion is about 67%. According to some embodiments, the circumference of the stent covered by the flow-diverting portion is about 68%. According to some embodiments, the circumference of the stent covered by the flow-diverting portion is about 69%. According to some embodiments, the circumference of the stent covered by the flow-diverting portion is about 70%. According to some embodiments, the circumference of the stent covered by the flow-diverting portion is about 71%. According to some embodiments, the circumference of the stent covered by the flow-diverting portion is about 72%. According to some embodiments, the circumference of the stent covered by the flow-diverting portion is about 73%. According to some embodiments, the circumference of the stent covered by the flow-diverting portion is about 74%. According to some embodiments, the circumference of the stent covered by the flow-diverting portion is about 75%. According to some embodiments, the circumference of the stent covered by the flow-diverting portion is about 76%. According to some embodiments, the circumference of the stent covered by the flow-diverting portion is about 77%. According to some embodiments, the circumference of the stent covered by the flow-diverting portion is about 78%. According to some embodiments, the circumference of the stent covered by the flow-diverting portion is about 79%. According to some embodiments, the circumference of the stent covered by the flow-diverting portion is about 80%. According to some embodiments, the circumference of the stent covered by the flow-diverting portion is about 81%. According to some embodiments, the circumference of the stent covered by the flow-diverting portion is about 82%. According to some embodiments, the circumference of the stent covered by the flow-diverting portion is about 83%. According to some embodiments, the circumference of the stent covered by the flow-diverting portion is about 84%. According to some embodiments, the circumference of the stent covered by the flow-diverting portion is about 85%. According to some embodiments, the circumference of the stent covered by the flow-diverting portion is about 86%. According to some embodiments, the circumference of the stent covered by the flow-diverting portion is about 87%. According to some embodiments, the circumference of the stent covered by the flow-diverting portion is about 88%. According to some embodiments, the circumference of the stent covered by the flow-diverting portion is about 89%. According to some embodiments, the circumference of the stent covered by the flow-diverting portion is about 90%. According to some embodiments, the circumference of the stent covered by the flow-diverting portion is about 91%. According to some embodiments, the circumference of the stent covered by the flow-diverting portion is about 92%. According to some embodiments, the circumference of the stent covered by the flow-diverting portion is about 93%. According to some embodiments, the circumference of the stent covered by the flow-diverting portion is about 94%. According to some embodiments, the circumference of the stent covered by the flow-diverting portion is about 95%. According to some embodiments, the circumference of the stent covered by the flow-diverting portion is about 96%. According to some embodiments, the circumference of the stent covered by the flow-diverting portion is about 97%. According to some embodiments, the circumference of the stent covered by the flow-diverting portion is about 98%. According to some embodiments, the circumference of the stent covered by the flow-diverting portion is about 99%. According to some embodiments, the circumference of the stent covered by the flow-diverting portion is about 100% of the total circumference of the stent.

According to some embodiments, the flow-diverting portion is placed on an aneurysm neck. According to some embodiments, the stent is adapted to be rotated. According to some embodiments, the stent is capable of being rotated in vivo so that the flow-diverting portion is placed in contact with an aneurysm neck.

According to some embodiments, the stent may be in the form of a braid, a mesh or a combination thereof. According to some embodiments, the stent comprises interstices (meaning very small, intervening spaces).

According to some embodiments, the stent of the described invention may be comprised of one or more materials. For example, these materials may include, without limitation, polytetrafluoroethylene (PTFE), chromium alloys, steel-chromium alloy (stainless steel), platinum alloys, platinum-tungsten alloy, cobalt alloys, cobalt-chromium alloy, nickel alloys, nickel-cobalt alloy, nickel-titanium alloy (Nitinol™), molybdenum alloys, polycarbonates (i.e., linear polyesters of carbonic acids in which carbonate groups recur in the polymer chain by phosgenation of a dihydroxy aromatic) such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in a linear chain, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, olefins such as polyethylene and polypropylene, porous rubber, cross-linked poly(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers, polyamides, polyurethanes, polyethylene oxides, polyox, polyox blended with polyacrylic acid or Carbopol™, cellulose derivatives such as hydroxypropyl methyl cellulose, hydroxyethyl cellulose, hydroxypropyl cellulose, pectin, starch, guar gum, locust bean gum, and the like.

According to some embodiments, the flow-diverting portion comprises a flow diverting material. According to some embodiments, the flow-diverting material is non-permeable. According to some embodiments, the flow-diverting material is selectively permeable. According to some embodiments, the flow-diverting material is a thermoplastic, a hydrogel or a combination thereof. According to some embodiments, the flow-diverting material is adapted to increase blood vessel wall adherence and minimize risk of an endoleak. According to some embodiments, the flow-diverting material is adapted to increase blood vessel wall adherence and minimize risk of an endoleak by the addition of a hydrogel adhered to the outer surface of the non-permeable material which abuts a vessel wall. According to some embodiments, the flow-diverting material is adapted to increase blood vessel wall adherence and minimize risk of an endoleak by the addition of a hydrogel adhered to the outer surface of the selectively permeable material which abuts a vessel wall. According to some embodiments, the flow-diverting portion comprises a metal alloy. According to some embodiments, the metal alloy is coated with a hydrogel. According to some embodiments, the entire metal alloy is coated with a hydrogel. According to some embodiments, a portion of the metal alloy is coated with a hydrogel.

According to some embodiments, the flow-diverting material is a thermoplastic. According to some embodiments, the thermoplastic is non-permeable. According to some embodiments, the thermoplastic is selectively permeable. According to some embodiments, the thermoplastic covers at least 1% to at least 100% of the length (l') of the flow-diverting portion of the stent. Thermoplastics include, but are not limited to, nylon, polyethylene terephthalate (PET) (Dacron®), urethane, polyethylene, polyvinyl chloride (PVC), polyether ether ketone (PEEK) and polyester. According to some embodiments, the thermoplastic is on the outside of the stent. According to some embodiments, the thermoplastic is on the inside of the stent. According to some embodiments, the thermoplastic is sewn to the stent. According to some embodiments, the thermoplastic is sewn to the outside of the stent. According to some embodiments, the thermoplastic is sewn to the inside of the stent. According to some embodiments, polyethylene terephthalate (PET) (Dacron®) is sewn to the stent. According to some embodiments, the polyethylene terephthalate (PET) (Dacron®) is sewn to the outside of the stent. According to some embodiments, the polyethylene terephthalate (PET) (Dacron®) is sewn to the inside of the stent. According to some embodiments, a hydrogel is applied to a surface of the thermoplastic material. According to some embodiments, the hydrogel is applied to an outer surface of the thermoplastic material. According to some embodiments, the hydrogel is applied to an inner surface of the thermoplastic material. According to some embodiments, the hydrogel expands upon exposure to blood. According to some embodiments, a hydrogel is applied to a surface of the polyethylene terephthalate (PET) (Dacron®). According to some embodiments, the hydrogel is applied to an outer surface of the polyethylene terephthalate (PET) (Dacron®). According to some embodiments, the hydrogel is applied to an inner surface of the polyethylene terephthalate (PET) (Dacron®). According to some embodiments, the hydrogel expands upon exposure to blood. According to some embodiments, the inner diameter (d) of the stent ranges from about 0.1 mm to about 600 mm. According to some embodiments, the inner diameter (d) ranges from about 0.5 mm to about 150 mm. According to some embodiments, the inner diameter (d) of the stent ranges from about 0.1 mm to about 60 m. According to some embodiments, the length (l) of the stent ranges from about 1 mm to about 800 mm. According to some embodiments, the stent is connected to a wire. According to some embodiments, the wire is connected to the proximal end of an existing stent. According to some embodiments, the wire is connected to the distal end of the stent. According to some embodiments, the wire is detachable. According to some embodiments, the wire is mechanically detachable. According to some embodiments, the stent connects to a single, or to multiple, mechanically-detachable site on the wire. According to some embodiments, the wire is electrolytically detachable. According to some embodiments, the stent connects to a single or to multiple, electrolytically-detachable site on the wire. According to some embodiments, the wire is hydrostatically detachable. According to some embodiments, the stent connects to a single, or to multiple, hydrostatically-detachable site on the wire. According to some embodiments, the stent is retrieved from a blood vessel. According to some embodiments, the stent is retrievable when about 0% to about 100% of the stent is deployed, before detachment. According to some embodiments, the stent can be re-positioned in a blood vessel. According to some embodiments, the stent can be re-positioned when about 0% to about 100% of the stent is deployed. According to some embodiments, the stent can be re-sheathed in a blood vessel. According to some embodiments, the stent can be re-sheathed up to the flow-diverting portion of the stent. According to some embodiments, the stent can be re-sheathed when about 0% to about 100% of the stent is deployed. According to some embodiments, the stent is tapered. According to some embodiments, the stent is tapered at a proximal end. According to some embodiments, the stent is tapered at a distal end. According to some embodiments, the stent is tapered at a site along the length (l) of the stent. According to some embodiments, the stent is tapered at a single site along the length (l) of the stent. According to some embodiments, the stent is tapered at multiple sites along the length (l) of the stent. According to some embodiments, the stent is flared. According to some embodiments, the stent is flared at a proximal end. According to some embodiments, the stent is flared at a distal end. According to some embodiments, the stent is flared at a site along the length (l) of the stent. According to some embodiments, the stent is flared at a single site along the length (l) of the stent. According to some embodiments, the stent is flared at multiple sites along the length (l) of the stent.

According to some embodiments, the flow diverting-material is in form of a sheet. According to some embodiments, the sheet covers the flow-diverting portion of the stent. According to some embodiments, the sheet covers the inside of the flow-diverting portion of the stent. According to some embodiments, the sheet covers the outside of the flow-diverting portion of the stent. According to some embodiments, the sheet is a non-permeable material. According to some embodiments, the sheet is a selectively permeable material. According to some embodiments, the sheet is a thermoplastic. According to some embodiments, the thermoplastic is non-permeable. According to some embodiments, the thermoplastic is selectively permeable. Thermoplastics include, but are not limited to, nylon, polyethylene terephthalate (PET) (Dacron®), urethane, polyethylene, polyvinyl chloride (PVC), polyether ether ketone (PEEK) and polyester. According to some embodiments, a hydrogel is applied to a surface of the sheet. According to some embodiments, the hydrogel is applied to an outer surface of the sheet. According to some embodiments, the hydrogel is applied to an inner surface of the sheet. According to some embodiments, the hydrogel expands upon exposure to blood.

According to some embodiments, the sheet is polyethylene terephthalate (PET) (Dacron®). According to some embodiments, a hydrogel is applied to a surface of the polyethylene terephthalate (PET) (Dacron®) sheet. According to some embodiments, the hydrogel is applied to an outer surface of the polyethylene terephthalate (PET) (Dacron®) sheet. According to some embodiments, the hydrogel is applied to an inner surface of the polyethylene terephthalate (PET) (Dacron®) sheet. According to some embodiments, the hydrogel expands upon exposure to blood.

Polyethylene terephthalate (PET) (Dacron®) is a condensation polymer produced from ethylene glycol and terephthalic acid. Its properties include tensile strength, resistance to stretching (both wet and dry) and resistance to degradation by chemical bleaches and by abrasion. For biomedical applications, PET is the most important polymer of its family due to its dimensional stability, durability, and its resistance to sterilization and biodegradation. Dacron® fabrics can be knitted or woven. The weaving technique involves at least two sets of yarn: a warp (longitudinal) yarn; and a weft/filling (crosswise) yarn laced at right angles to each other. The fabric's characteristics can be varied by modifying parameters, such as the type of weave, thread spacing, linear density and twist factors of the warp and filling yarns. Compared to other structures, woven fabrics are dimensionally stable and less extensible and porous. PET yarn is available in several geometries including, but not limited to, monofilaments with rectangular cross-section (e.g., ≥16×7 µm$^2$) and thin monofilaments (e.g., 10-12.5 µm diameter). There are two types of knitted structures: a warp-knit structure (similar to tricot) and a weft-knit structure (similar to a hand-knit sweater). The warp-knit structure involves loops made from each warp thread that are formed along the length of the fabric. Warp-knitted structures are versatile and can be engineered with a variety of mechanical properties matching those of woven structures. The weft-knit structure involves loops made from each weft thread formed across the width of the fabric. Weft-knitted structures are highly extensible; however, dimensional stability can be compromised if additional yarns are not used to interlock the loops. Flexibility, pore size and distribution of knitted structures can be controlled by varying the density of the knit. Compared to woven structures, knitted structures are more flexible, radially distensible and are highly porous. Porosity of the knitted structure can be overcome by the addition of gelatin, collagen and/or albumin.

According to some embodiments, the flow-diverting material is a hydrogel. According to some embodiments, the hydrogel is non-biodegradable. According to some embodiments, the hydrogel is non-permeable. According to some embodiments, the hydrogel is selectively permeable. Hydrogels include, without limitation, synthetic polymer hydrogels, natural polymer hydrogels and mixed synthetic-natural polymer hydrogels. Non-limiting examples of synthetic polymer hydrogels include acrylic acid and its sodium and potassium salts, acrylamide, polyacrylates including, without limitation, poly (hydroxyethyl methacrylate) (PHEMA), poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), N-isopropylacrylamide, polyethylene glycol (PEG), PEG derivatives including, but not limited to, polyethylene oxide (PEO), polyethylene glycol methacrylate (PEGMA), polyethylene glycol dimethacrylate (PEGMA) and polyethylene glycol diacrylate (PEGDA), polyvinyl alcohol (PVA), polyvinyl pyrrolidone (PVP), polyimide (PI), polyurethane and crosslinked acrylamide-sodium acrylate co-polymer. Natural polymer hydrogels include, without limitation, hyaluronic acid, polyhyaluronic acid, casein, gelatin, glutin, alginate, chitosan, carboxymethyl cellulose, dextran and methylcellulose. Mixed synthetic-natural polymer hydrogels include, without limitation, PEG hydrogels mixed with methacrylate gelatin and N-isopropylacrylamide oligomers mixed with at least one of hyaluronic acid, carboxymethyl cellulose, dextran and methylcellulose.

According to some embodiments, the hydrogel is applied to a surface of the endovascular stent. According to some embodiments, the hydrogel is applied to an inside surface of the stent. According to some embodiments, the hydrogel is applied to an outside surface of the stent. According to some embodiments, the hydrogel is applied to a filament woven onto or into the stent. Non-limiting examples of filaments include threads, strands, strings, fibers, fibrils, yarns, braids, cords and wires. According to some embodiments, the filament is a natural filament. According to some embodiments, the filament is a synthetic filament. According to some embodiments, when the stent of the described invention comprising a covered portion comprising a hydrogel is advanced through a blood vessel, the hydrogel expands and fills the interstices of the covered portion of the stent to create the flow-diverting portion in vivo. According to some embodiments, the hydrogel expands upon exposure to blood.

According to some embodiments, the endovascular stent of the described invention is connected to a wire. According to some embodiments, the wire is connected to the proximal end of the stent. According to some embodiments, the wire is connected to the distal end of the stent. According to some embodiments, the stent is connected to a single site on the wire. According to some embodiments, multiple sites on the stent connect to a single site on the wire. According to some embodiments, multiple sites on the stent connect to multiple sites on the wire. According to some embodiments, the wire is detachable. According to some embodiments, the wire is mechanically detachable. According to some embodiments, the stent connects to a single, mechanically-detachable site on the wire. According to some embodiments, the wire is electrolytically detachable. According to some embodiments, the stent connects to a single, electrolytically-detachable site on the wire. According to some embodiments, the wire is hydrostatically detachable. According to some embodiments, the stent connects to a single, hydrostatically-detachable site on the wire.

Figure 5:
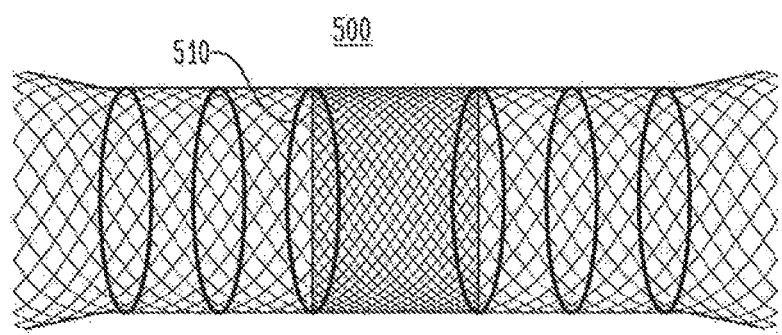
FIG. 5 shows an illustrative embodiment of an endovascular stent device 500. 510 shows an illustrative embodiment of a strut of the endovascular stent.

According to some embodiments, the stent of the described invention comprises a strut (meaning a structure forming part of a framework to resist compression). According to some embodiments, the stent of the described invention comprises multiple struts. According to one embodiment, FIG. 5 illustrates an endovascular stent device 500 comprising a strut 510.

According to some embodiments, the strut is comprised of a metal material. According to some embodiments, the metal material is a metal alloy. Non-limiting examples of metal alloys include steel-chromium alloy (stainless steel), platinum-tungsten alloy, cobalt-chromium alloy, nickel-cobalt alloy and nickel-titanium alloy (Nitinol™).

According to some embodiments, the stent of the described invention comprises two or more struts, for example, 2 struts, 3 struts, 4 struts, 5 struts, 6 struts, 7 struts, 8 struts, 9 struts and 10 struts. According to some embodiments, the struts are evenly or unevenly spaced at intervals along the length of the stent.

According to some embodiments, the strut is in a form of geometric shape. According to some embodiments, the geometric shape includes, but is not limited to, a square, a circle, an ellipse, a tear drop, a rectangle, a cylinder, and a circular arc. According to some embodiments, the geometric shape comprises varying aspect ratios (AR) of width to height (w:h). Such aspect ratios include, but are not limited to, 2:1 (w:h), 4:1 (w:h), 8:1 (w:h) and the like.

Figure 6:
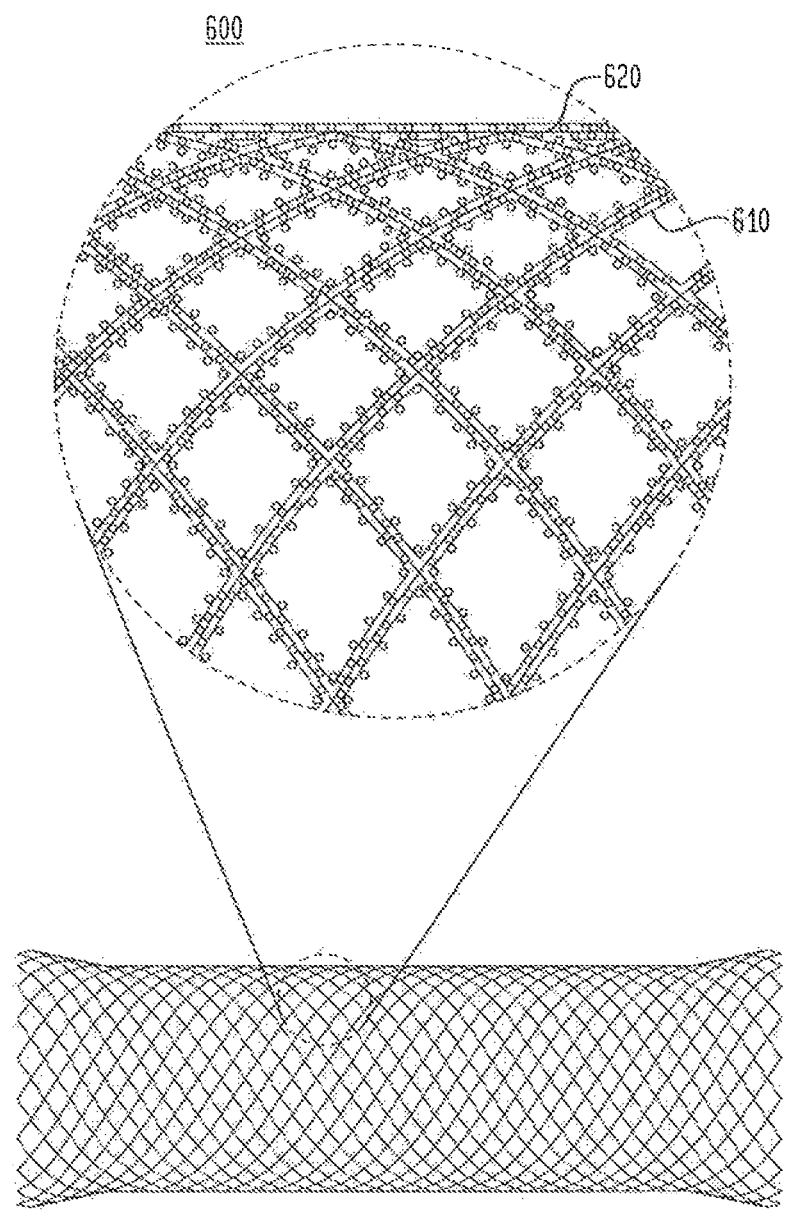
FIG. 6 shows an illustrative embodiment of an endovascular stent device 600, having a strut 610, coated with a hydrogel 620.
Figure 7:
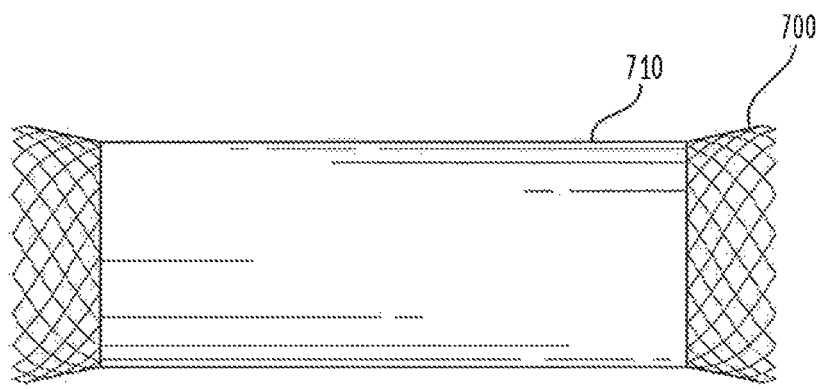
FIG. 7 shows an illustrative embodiment of a flow-impeding cover material 710 on a portion of the outer surface of the circumference of an endovascular device 700.
Figure 8:
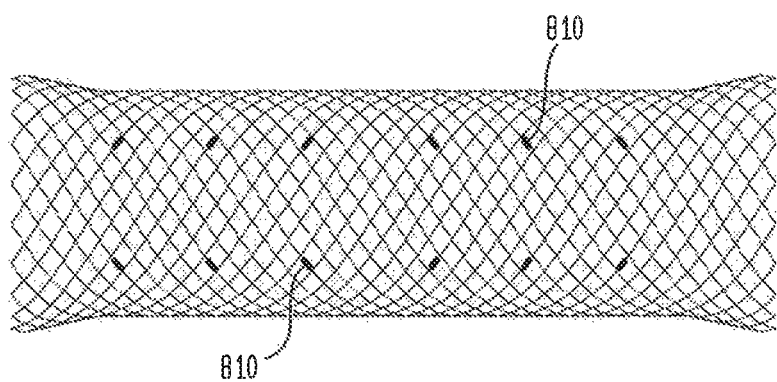
FIG. 8 shows an illustrative embodiment of radiopaque markers 810 for positioning the endovascular device in a blood vessel.
Figure 9A:
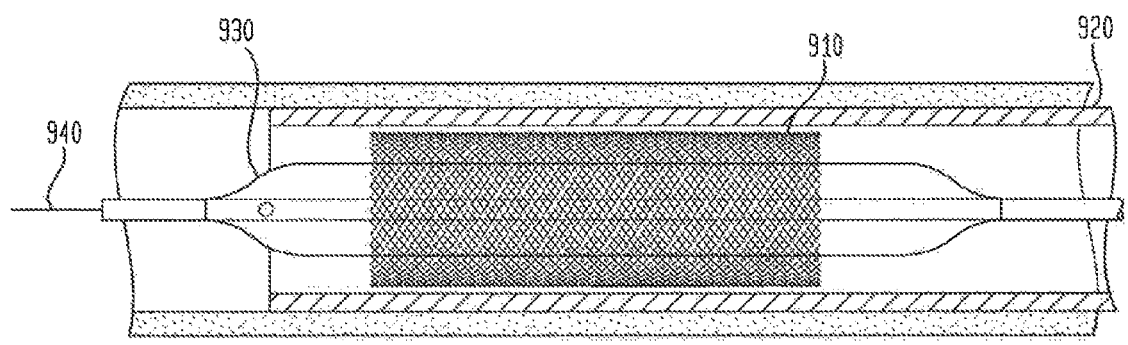
FIGS. 9A and 9B.
Figure 9B:
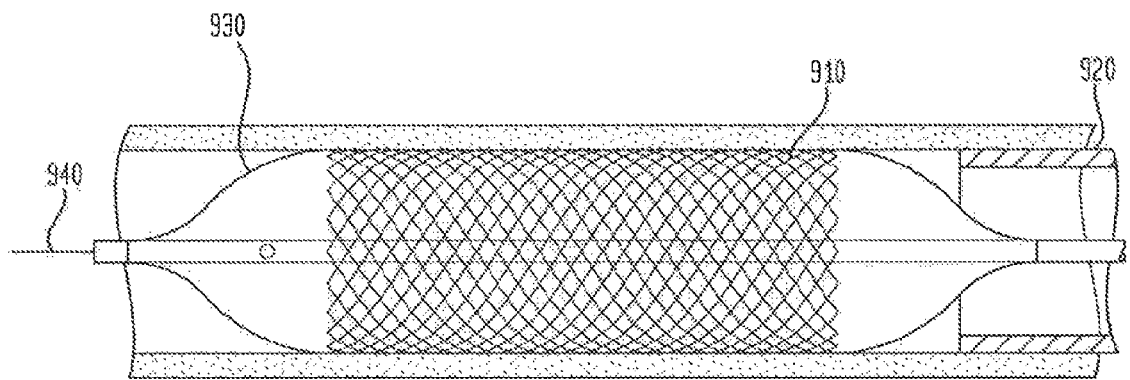
Figure 10:
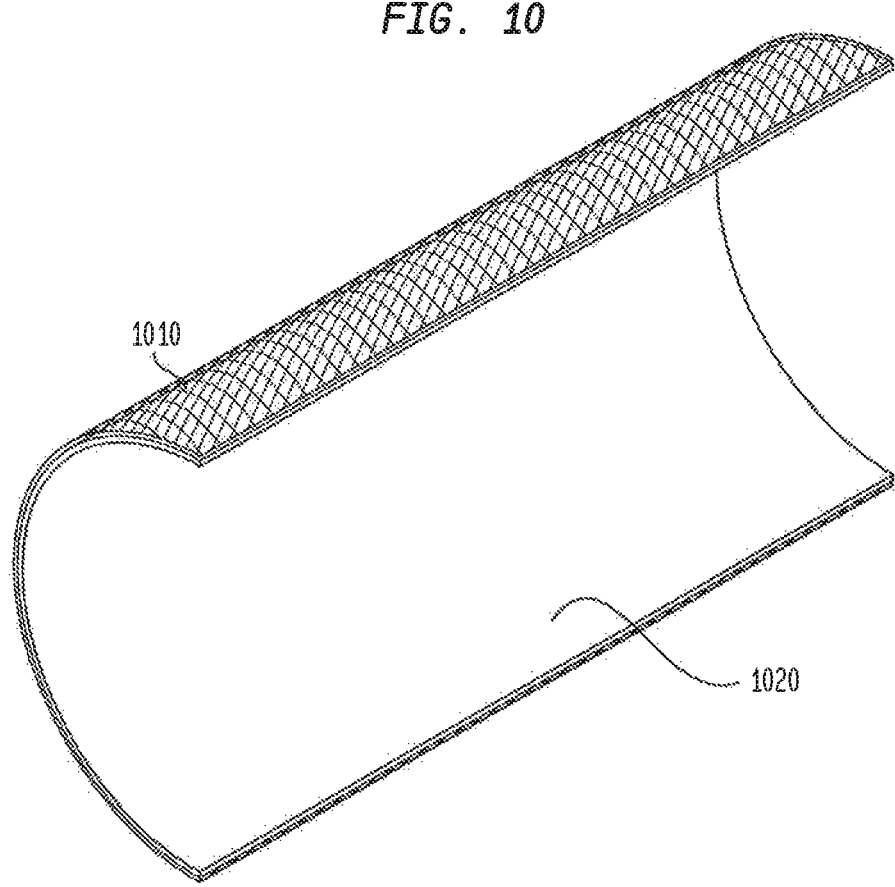
FIG. 10 shows an illustrative embodiment of an endovascular device comprising a circumference comprising an outer surface (1010) and an inner surface (1020). The flow-impeding material is shown on the inner surface of the circumference of the endovascular device.

According to some embodiments, the flow-diverting portion of the endovascular stent comprises two or more struts. According to some embodiments, diversion of blood flow is achieved by increasing the density of the struts within the flow-diverting portion of the endovascular stent. According to some embodiments, the flow-diverting portion of the stent comprising two or more struts comprises a flow diverting material. According to some embodiments, the flow diverting material is a metal, a cloth, a cloth-like material or a combination thereof. According to some embodiments, the flow-diverting material is a hydrogel. According to some embodiments, the hydrogel is applied to a surface of the strut. According to one embodiment, FIG. 6 illustrates an endovascular stent device 600 comprising a strut 610 coated with a hydrogel 620. According to some embodiments, the hydrogel is applied to an inner wall of the strut. According to some embodiments, the hydrogel is applied to an outer wall of the strut. According to some embodiments, the hydrogel is applied to a surface of the strut facing adjacent struts.

According to some embodiments, the hydrogel expands upon exposure to blood. According to some embodiments, the hydrogel applied to one strut expands in vivo to contact the hydrogel applied to adjacent struts. According to some embodiments, the hydrogel expands upon exposure to blood to cover at least 1% to at least 100% of the length (l') of the flow-diverting portion of the stent. According to some embodiments, the hydrogel expands upon exposure to blood to cover at least 1% of the length (l') of the flow-diverting portion of the stent. According to some embodiments, the hydrogel expands upon exposure to blood to cover at least 2% of the length (l') of the flow-diverting portion of the stent. According to some embodiments, the hydrogel expands upon exposure to blood to cover at least 3% of the length (l') of the flow-diverting portion of the stent. According to some embodiments, the hydrogel expands upon exposure to blood to cover at least 4% of the length (l') of the flow-diverting portion of the stent. According to some embodiments, the hydrogel expands upon exposure to blood to cover at least 5% of the length (l') of the flow-diverting portion of the stent. According to some embodiments, the hydrogel expands upon exposure to blood to cover at least 6% of the length (l') of the flow-diverting portion of the stent. According to some embodiments, the hydrogel expands upon exposure to blood to cover at least 7% of the length (l') of the flow-diverting portion of the stent. According to some embodiments, the hydrogel expands upon exposure to blood to cover at least 8% of the length (l') of the flow-diverting portion of the stent. According to some embodiments, the hydrogel expands upon exposure to blood to cover at least 9% of the length (l') of the flow-diverting portion of the stent. According to some embodiments, the hydrogel expands upon exposure to blood to cover at least 10% of the length (l') of the flow-diverting portion of the stent. According to some embodiments, the hydrogel expands upon exposure to blood to cover at least 11% of the length (l') of the flow-diverting portion of the stent. According to some embodiments, the hydrogel expands upon exposure to blood to cover at least 12% of the length (l') of the flow-diverting portion of the stent. According to some embodiments, the hydrogel expands upon exposure to blood to cover at least 13% of the length (l') of the flow-diverting portion of the stent. According to some embodiments, the hydrogel expands upon exposure to blood to cover at least 14% of the length (l') of the flow-diverting portion of the stent. According to some embodiments, the hydrogel expands upon exposure to blood to cover at least 15% of the length (l') of the flow-diverting portion of the stent. According to some embodiments, the hydrogel expands upon exposure to blood to cover at least 16% of the length (l') of the flow-diverting portion of the stent. According to some embodiments, the hydrogel expands upon exposure to blood to cover at least 17% of the length (l') of the flow-diverting portion of the stent. According to some embodiments, the hydrogel expands upon exposure to blood to cover at least 18% of the length (l') of the flow-diverting portion of the stent. According to some embodiments, the hydrogel expands upon exposure to blood to cover at least 19% of the length (l') of the flow-diverting portion of the stent. According to some embodiments, the hydrogel expands upon exposure to blood to cover at least 20% of the length (l') of the flow-diverting portion of the stent. According to some embodiments, the hydrogel expands upon exposure to blood to cover at least 21% of the length (l') of the flow-diverting portion of the stent. According to some embodiments, the hydrogel expands upon exposure to blood to cover at least 22% of the length (l') of the flow-diverting portion of the stent. According to some embodiments, the hydrogel expands upon exposure to blood to cover at least 23% of the length (l') of the flow-diverting portion of the stent. According to some embodiments, the hydrogel expands upon exposure to blood to cover at least 24% of the length (l') of the flow-diverting portion of the stent. According to some embodiments, the hydrogel expands upon exposure to blood to cover at least 25% of the length (l') of the flow-diverting portion of the stent. According to some embodiments, the hydrogel expands upon exposure to blood to cover at least 26% of the length (l') of the flow-diverting portion of the stent. According to some embodiments, the hydrogel expands upon exposure to blood to cover at least 27% of the length (l') of the flow-diverting portion of the stent. According to some embodiments, the hydrogel expands upon exposure to blood to cover at least 28% of the length (l') of the flow-diverting portion of the stent. According to some embodiments, the hydrogel expands upon exposure to blood to cover at least 29% of the length (l') of the flow-diverting portion of the stent. According to some embodiments, the hydrogel expands upon exposure to blood to cover at least 30% of the length (l') of the flow-diverting portion of the stent. According to some embodiments, the hydrogel expands upon exposure to blood to cover at least 31% of the length (l') of the flow-diverting portion of the stent. According to some embodiments, the hydrogel expands upon exposure to blood to cover at least 32% of the length (l') of the flow-diverting portion of the stent. According to some embodiments, the hydrogel expands upon exposure to blood to cover at least 33% of the length (l') of the flow-diverting portion of the stent. According to some embodiments, the hydrogel expands upon exposure to blood to cover at least 34% of the length (l') of the flow-diverting portion of the stent. According to some embodiments, the hydrogel expands upon exposure to blood to cover at least 35% of the length (l') of the flow-diverting portion of the stent. According to some embodiments, the hydrogel expands upon exposure to blood to cover at least 36% of the length (l') of the flow-diverting portion of the stent. According to some embodiments, the hydrogel expands upon exposure to blood to cover at least 37% of the length (l') of the flow-diverting portion of the stent. According to some embodiments, the hydrogel expands upon exposure to blood to cover at least 38% of the length (l') of the flow-diverting portion of the stent. According to some embodiments, the hydrogel expands upon exposure to blood to cover at least 39% of the length (l') of the flow-diverting portion of the stent. According to some embodiments, the hydrogel expands upon exposure to blood to cover at least 40% of the length (l') of the flow-diverting portion of the stent. According to some embodiments, the hydrogel expands upon exposure to blood to cover at least 41% of the length (l') of the flow-diverting portion of the stent. According to some embodiments, the hydrogel expands upon exposure to blood to cover at least 42% of the length (l') of the flow-diverting portion of the stent. According to some embodiments, the hydrogel expands upon exposure to blood to cover at least 43% of the length (l') of the flow-diverting portion of the stent. According to some embodiments, the hydrogel expands upon exposure to blood to cover at least 44% of the length (l') of the flow-diverting portion of the stent. According to some embodiments, the hydrogel expands upon exposure to blood to cover at least 45% of the length (l') of the flow-diverting portion of the stent. According to some embodiments, the hydrogel expands upon exposure to blood to cover at least 46% of the length (l') of the flow-diverting portion of the stent. According to some embodiments, the hydrogel expands upon exposure to blood to cover at least 47% of the length (l') of the flow-diverting portion of the stent. According to some embodiments, the hydrogel expands upon exposure to blood to cover at least 48% of the length (l') of the flow-diverting portion of the stent. According to some embodiments, the hydrogel expands upon exposure to blood to cover at least 49% of the length (l') of the flow-diverting portion of the stent. According to some embodiments, the hydrogel expands upon exposure to blood to cover at least 50% of the length (l') of the flow-diverting portion of the stent. According to some embodiments, the hydrogel expands upon exposure to blood to cover at least 51% of the length (l') of the flow-diverting portion of the stent. According to some embodiments, the hydrogel expands upon exposure to blood to cover at least 52% of the length (l') of the flow-diverting portion of the stent. According to some embodiments, the hydrogel expands upon exposure to blood to cover at least 53% of the length (l') of the flow-diverting portion of the stent. According to some embodiments, the hydrogel expands upon exposure to blood to cover at least 54% of the length (l') of the flow-diverting portion of the stent. According to some embodiments, the hydrogel expands upon exposure to blood to cover at least 55% of the length (l') of the flow-diverting portion of the stent. According to some embodiments, the hydrogel expands upon exposure to blood to cover at least 56% of the length (l') of the flow-diverting portion of the stent. According to some embodiments, the hydrogel expands upon exposure to blood to cover at least 57% of the length (l') of the flow-diverting portion of the stent. According to some embodiments, the hydrogel expands upon exposure to blood to cover at least 58% of the length (l') of the flow-diverting portion of the stent. According to some embodiments, the hydrogel expands upon exposure to blood to cover at least 59% of the length (l') of the flow-diverting portion of the stent. According to some embodiments, the hydrogel expands upon exposure to blood to cover at least 60% of the length (l') of the flow-diverting portion of the stent. According to some embodiments, the hydrogel expands upon exposure to blood to cover at least 61% of the length (l') of the flow-diverting portion of the stent. According to some embodiments, the hydrogel expands upon exposure to blood to cover at least 62% of the length (l') of the flow-diverting portion of the stent. According to some embodiments, the hydrogel expands upon exposure to blood to cover at least 63% of the length (l') of the flow-diverting portion of the stent. According to some embodiments, the hydrogel expands upon exposure to blood to cover at least 64% of the length (l') of the flow-diverting portion of the stent. According to some embodiments, the hydrogel expands upon exposure to blood to cover at least 65% of the length (l') of the flow-diverting portion of the stent. According to some embodiments, the hydrogel expands upon exposure to blood to cover at least 66% of the length (l') of the flow-diverting portion of the stent. According to some embodiments, the hydrogel expands upon exposure to blood to cover at least 67% of the length (l') of the flow-diverting portion of the stent. According to some embodiments, the hydrogel expands upon exposure to blood to cover at least 68% of the length (l') of the flow-diverting portion of the stent. According to some embodiments, the hydrogel expands upon exposure to blood to cover at least 69% of the length (l') of the flow-diverting portion of the stent. According to some embodiments, the hydrogel expands upon exposure to blood to cover at least 70% of the length (l') of the flow-diverting portion of the stent. According to some embodiments, the hydrogel expands upon exposure to blood to cover at least 71% of the length (l') of the flow-diverting portion of the stent. According to some embodiments, the hydrogel expands upon exposure to blood to cover at least 72% of the length (l') of the flow-diverting portion of the stent. According to some embodiments, the hydrogel expands upon exposure to blood to cover at least 73% of the length (l') of the flow-diverting portion of the stent. According to some embodiments, the hydrogel expands upon exposure to blood to cover at least 74% of the length (l') of the flow-diverting portion of the stent. According to some embodiments, the hydrogel expands upon exposure to blood to cover at least 75% of the length (l') of the flow-diverting portion of the stent. According to some embodiments, the hydrogel expands upon exposure to blood to cover at least 76% of the length (l') of the flow-diverting portion of the stent. According to some embodiments, the hydrogel expands upon exposure to blood to cover at least 77% of the length (l') of the flow-diverting portion of the stent. According to some embodiments, the hydrogel expands upon exposure to blood to cover at least 78% of the length (l') of the flow-diverting portion of the stent. According to some embodiments, the hydrogel expands upon exposure to blood to cover at least 79% of the length (l') of the flow-diverting portion of the stent. According to some embodiments, the hydrogel expands upon exposure to blood to cover at least 80% of the length (l') of the flow-diverting portion of the stent. According to some embodiments, the hydrogel expands upon exposure to blood to cover at least 81% of the length (l') of the flow-diverting portion of the stent. According to some embodiments, the hydrogel expands upon exposure to blood to cover at least 82% of the length (l') of the flow-diverting portion of the stent. According to some embodiments, the hydrogel expands upon exposure to blood to cover at least 83% of the length (l') of the flow-diverting portion of the stent. According to some embodiments, the hydrogel expands upon exposure to blood to cover at least 84% of the length (l') of the flow-diverting portion of the stent. According to some embodiments, the hydrogel expands upon exposure to blood to cover at least 85% of the length (l') of the flow-diverting portion of the stent. According to some embodiments, the hydrogel expands upon exposure to blood to cover at least 86% of the length (l') of the flow-diverting portion of the stent. According to some embodiments, the hydrogel expands upon exposure to blood to cover at least 87% of the length (l') of the flow-diverting portion of the stent. According to some embodiments, the hydrogel expands upon exposure to blood to cover at least 88% of the length (l') of the flow-diverting portion of the stent. According to some embodiments, the hydrogel expands upon exposure to blood to cover at least 89% of the length (l') of the flow-diverting portion of the stent. According to some embodiments, the hydrogel expands upon exposure to blood to cover at least 90% of the length (l') of the flow-diverting portion of the stent. According to some embodiments, the hydrogel expands upon exposure to blood to cover at least 91% of the length (l') of the flow-diverting portion of the stent. According to some embodiments, the hydrogel expands upon exposure to blood to cover at least 92% of the length (l') of the flow-diverting portion of the stent. According to some embodiments, the hydrogel expands upon exposure to blood to cover at least 93% of the length (l') of the flow-diverting portion of the stent. According to some embodiments, the hydrogel expands upon exposure to blood to cover at least 94% of the length (l') of the flow-diverting portion of the stent. According to some embodiments, the hydrogel expands upon exposure to blood to cover at least 95% of the length (l') of the flow-diverting portion of the stent. According to some embodiments, the hydrogel expands upon exposure to blood to cover at least 96% of the length (l') of the flow-diverting portion of the stent. According to some embodiments, the hydrogel expands upon exposure to blood to cover at least 97% of the length (l') of the flow-diverting portion of the stent. According to some embodiments, the hydrogel expands upon exposure to blood to cover at least 98% of the length (l') of the flow-diverting portion of the stent. According to some embodiments, the hydrogel expands upon exposure to blood to cover at least 99% of the length (l') of the flow-diverting portion of the stent. According to some embodiments, the hydrogel expands upon exposure to blood to cover at least 100% of the length (l') of the flow-diverting portion of the stent. According to some embodiments, the hydrogel expands upon exposure to blood to cover the entire circumference of the stent. According to some embodiments, the hydrogel expands upon exposure to blood to partially cover the circumference of the stent. According to some embodiments, the hydrogel expands upon exposure to blood to cover a range from about 1% to about 100% of the total circumference of the stent. According to some embodiments, the hydrogel expands upon exposure to blood to cover about 1% of the total circumference of the stent. According to some embodiments, the hydrogel expands upon exposure to blood to cover about 2% of the total circumference of the stent. According to some embodiments, the hydrogel expands upon exposure to blood to cover about 3% of the total circumference of the stent. According to some embodiments, the hydrogel expands upon exposure to blood to cover about 4% of the total circumference of the stent. According to some embodiments, the hydrogel expands upon exposure to blood to cover about 5% of the total circumference of the stent. According to some embodiments, the hydrogel expands upon exposure to blood to cover about 6% of the total circumference of the stent. According to some embodiments, the hydrogel expands upon exposure to blood to cover about 7% of the total circumference of the stent. According to some embodiments, the hydrogel expands upon exposure to blood to cover about 8% of the total circumference of the stent. According to some embodiments, the hydrogel expands upon exposure to blood to cover about 9% of the total circumference of the stent. According to some embodiments, the hydrogel expands upon exposure to blood to cover about 10% of the total circumference of the stent. According to some embodiments, the hydrogel expands upon exposure to blood to cover about 11% of the total circumference of the stent. According to some embodiments, the hydrogel expands upon exposure to blood to cover about 12% of the total circumference of the stent. According to some embodiments, the hydrogel expands upon exposure to blood to cover about 13% of the total circumference of the stent. According to some embodiments, the hydrogel expands upon exposure to blood to cover about 14% of the total circumference of the stent. According to some embodiments, the hydrogel expands upon exposure to blood to cover about 15% of the total circumference of the stent. According to some embodiments, the hydrogel expands upon exposure to blood to cover about 16% of the total circumference of the stent. According to some embodiments, the hydrogel expands upon exposure to blood to cover about 17% of the total circumference of the stent. According to some embodiments, the hydrogel expands upon exposure to blood to cover about 18% of the total circumference of the stent. According to some embodiments, the hydrogel expands upon exposure to blood to cover about 19% of the total circumference of the stent. According to some embodiments, the hydrogel expands upon exposure to blood to cover about 20% of the total circumference of the stent. According to some embodiments, the hydrogel expands upon exposure to blood to cover about 21% of the total circumference of the stent. According to some embodiments, the hydrogel expands upon exposure to blood to cover about 22% of the total circumference of the stent. According to some embodiments, the hydrogel expands upon exposure to blood to cover about 23% of the total circumference of the stent. According to some embodiments, the hydrogel expands upon exposure to blood to cover about 24% of the total circumference of the stent. According to some embodiments, the hydrogel expands upon exposure to blood to cover about 25% of the total circumference of the stent. According to some embodiments, the hydrogel expands upon exposure to blood to cover about 26% of the total circumference of the stent. According to some embodiments, the hydrogel expands upon exposure to blood to cover about 27% of the total circumference of the stent. According to some embodiments, the hydrogel expands upon exposure to blood to cover about 28% of the total circumference of the stent. According to some embodiments, the hydrogel expands upon exposure to blood to cover about 29% of the total circumference of the stent. According to some embodiments, the hydrogel expands upon exposure to blood to cover about 30% of the total circumference of the stent. According to some embodiments, the hydrogel expands upon exposure to blood to cover about 31% of the total circumference of the stent. According to some embodiments, the hydrogel expands upon exposure to blood to cover about 32% of the total circumference of the stent. According to some embodiments, the hydrogel expands upon exposure to blood to cover about 33% of the total circumference of the stent. According to some embodiments, the hydrogel expands upon exposure to blood to cover about 34% of the total circumference of the stent. According to some embodiments, the hydrogel expands upon exposure to blood to cover about 35% of the total circumference of the stent. According to some embodiments, the hydrogel expands upon exposure to blood to cover about 36% of the total circumference of the stent. According to some embodiments, the hydrogel expands upon exposure to blood to cover about 37% of the total circumference of the stent. According to some embodiments, the hydrogel expands upon exposure to blood to cover about 38% of the total circumference of the stent. According to some embodiments, the hydrogel expands upon exposure to blood to cover about 39% of the total circumference of the stent. According to some embodiments, the hydrogel expands upon exposure to blood to cover about 40% of the total circumference of the stent. According to some embodiments, the hydrogel expands upon exposure to blood to cover about 41% of the total circumference of the stent. According to some embodiments, the hydrogel expands upon exposure to blood to cover about 42% of the total circumference of the stent. According to some embodiments, the hydrogel expands upon exposure to blood to cover about 43% of the total circumference of the stent. According to some embodiments, the hydrogel expands upon exposure to blood to cover about 44% of the total circumference of the stent. According to some embodiments, the hydrogel expands upon exposure to blood to cover about 45% of the total circumference of the stent. According to some embodiments, the hydrogel expands upon exposure to blood to cover about 46% of the total circumference of the stent. According to some embodiments, the hydrogel expands upon exposure to blood to cover about 47% of the total circumference of the stent. According to some embodiments, the hydrogel expands upon exposure to blood to cover about 48% of the total circumference of the stent. According to some embodiments, the hydrogel expands upon exposure to blood to cover about 49% of the total circumference of the stent. According to some embodiments, the hydrogel expands upon exposure to blood to cover about 50% of the total circumference of the stent. According to some embodiments, the hydrogel expands upon exposure to blood to cover about 51% of the total circumference of the stent. According to some embodiments, the hydrogel expands upon exposure to blood to cover about 52% of the total circumference of the stent. According to some embodiments, the hydrogel expands upon exposure to blood to cover about 53% of the total circumference of the stent. According to some embodiments, the hydrogel expands upon exposure to blood to cover about 54% of the total circumference of the stent. According to some embodiments, the hydrogel expands upon exposure to blood to cover about 55% of the total circumference of the stent. According to some embodiments, the hydrogel expands upon exposure to blood to cover about 56% of the total circumference of the stent. According to some embodiments, the hydrogel expands upon exposure to blood to cover about 57% of the total circumference of the stent. According to some embodiments, the hydrogel expands upon exposure to blood to cover about 58% of the total circumference of the stent. According to some embodiments, the hydrogel expands upon exposure to blood to cover about 59% of the total circumference of the stent. According to some embodiments, the hydrogel expands upon exposure to blood to cover about 60% of the total circumference of the stent. According to some embodiments, the hydrogel expands upon exposure to blood to cover about 61% of the total circumference of the stent. According to some embodiments, the hydrogel expands upon exposure to blood to cover about 62% of the total circumference of the stent. According to some embodiments, the hydrogel expands upon exposure to blood to cover about 63% of the total circumference of the stent. According to some embodiments, the hydrogel expands upon exposure to blood to cover about 64% of the total circumference of the stent. According to some embodiments, the hydrogel expands upon exposure to blood to cover about 65% of the total circumference of the stent. According to some embodiments, the hydrogel expands upon exposure to blood to cover about 66% of the total circumference of the stent. According to some embodiments, the hydrogel expands upon exposure to blood to cover about 67% of the total circumference of the stent. According to some embodiments, the hydrogel expands upon exposure to blood to cover about 68% of the total circumference of the stent. According to some embodiments, the hydrogel expands upon exposure to blood to cover about 69% of the total circumference of the stent. According to some embodiments, the hydrogel expands upon exposure to blood to cover about 70% of the total circumference of the stent. According to some embodiments, the hydrogel expands upon exposure to blood to cover about 71% of the total circumference of the stent. According to some embodiments, the hydrogel expands upon exposure to blood to cover about 72% of the total circumference of the stent. According to some embodiments, the hydrogel expands upon exposure to blood to cover about 73% of the total circumference of the stent. According to some embodiments, the hydrogel expands upon exposure to blood to cover about 74% of the total circumference of the stent. According to some embodiments, the hydrogel expands upon exposure to blood to cover about 75% of the total circumference of the stent. According to some embodiments, the hydrogel expands upon exposure to blood to cover about 76% of the total circumference of the stent. According to some embodiments, the hydrogel expands upon exposure to blood to cover about 77% of the total circumference of the stent. According to some embodiments, the hydrogel expands upon exposure to blood to cover about 78% of the total circumference of the stent. According to some embodiments, the hydrogel expands upon exposure to blood to cover about 79% of the total circumference of the stent. According to some embodiments, the hydrogel expands upon exposure to blood to cover about 80% of the total circumference of the stent. According to some embodiments, the hydrogel expands upon exposure to blood to cover about 81% of the total circumference of the stent. According to some embodiments, the hydrogel expands upon exposure to blood to cover about 82% of the total circumference of the stent. According to some embodiments, the hydrogel expands upon exposure to blood to cover about 83% of the total circumference of the stent. According to some embodiments, the hydrogel expands upon exposure to blood to cover about 84% of the total circumference of the stent. According to some embodiments, the hydrogel expands upon exposure to blood to cover about 85% of the total circumference of the stent. According to some embodiments, the hydrogel expands upon exposure to blood to cover about 86% of the total circumference of the stent. According to some embodiments, the hydrogel expands upon exposure to blood to cover about 87% of the total circumference of the stent. According to some embodiments, the hydrogel expands upon exposure to blood to cover about 88% of the total circumference of the stent. According to some embodiments, the hydrogel expands upon exposure to blood to cover about 89% of the total circumference of the stent. According to some embodiments, the hydrogel expands upon exposure to blood to cover about 90% of the total circumference of the stent. According to some embodiments, the hydrogel expands upon exposure to blood to cover about 91% of the total circumference of the stent. According to some embodiments, the hydrogel expands upon exposure to blood to cover about 92% of the total circumference of the stent. According to some embodiments, the hydrogel expands upon exposure to blood to cover about 93% of the total circumference of the stent.

According to some embodiments, the hydrogel expands upon exposure to blood to cover about 94% of the total circumference of the stent. According to some embodiments, the hydrogel expands upon exposure to blood to cover about 95% of the total circumference of the stent. According to some embodiments, the hydrogel expands upon exposure to blood to cover about 96% of the total circumference of the stent. According to some embodiments, the hydrogel expands upon exposure to blood to cover about 97% of the total circumference of the stent. According to some embodiments, the hydrogel expands upon exposure to blood to cover about 98% of the total circumference of the stent. According to some embodiments, the hydrogel expands upon exposure to blood to cover about 99% of the total circumference of the stent. According to some embodiments, the hydrogel expands upon exposure to blood to cover about 100% of the total circumference of the stent.

According to some embodiments, one strut is connected to a wire. According to some embodiments, two or more struts are connected to a wire. According to some embodiments, the wire is connected to the proximal end of the strut.

According to some embodiments, the wire is detachable. According to some embodiments, the wire is mechanically detachable. According to some embodiments, the proximal ends of the struts connect to a single, mechanically-detachable site on the wire. According to some embodiments, the wire is electrolytically detachable. According to some embodiments, the proximal ends of the struts connect to a single, electrolytically-detachable site on the wire. According to some embodiments, the wire is hydrostatically detachable. According to some embodiments, the proximal ends of the struts connect to a single, hydrostatically-detachable site on the wire.

According to some embodiments, the struts of the stent simultaneously expand to a blood vessel wall when detached from the wire. Put another way, the struts of the stent expand and reach a blood vessel wall simultaneously, concurrently, or in synchrony when detached from the wire. According to some embodiments, each strut of the stent individually expands to contact a blood vessel wall when detached from the wire. Put another way, each strut of the stent expands and reaches a blood vessel wall at a different point in time when detached from the wire. That is, expansion of each strut of the stent to a blood vessel wall is asynchronous or non-simultaneous in relation to other struts when detached from the wire. According to some embodiments, each strut of the stent expands as it is delivered through a blood vessel. According to some embodiments, each strut of the stent expands as it is unsheathed from a delivery catheter/sheath. According to some embodiments, one or more balloons is/are mounted to each strut of the stent. According to some embodiments, each strut of the stent expands as the one or more balloons is/are expanded or inflated.

According to some embodiments, the hydrogel is applied to an existing stent. According to some embodiments, the existing stent comprises a strut. According to some embodiments, the existing stent comprises multiple struts. According to some embodiments, the strut is woven into the existing stent. According to some embodiments, diversion of blood flow is achieved by increasing the density of the struts along a segment of the existing stent. According to some embodiments, the hydrogel is applied to a surface of a strut or multiple struts of an existing stent. According to some embodiments, the existing stent comprises two or more struts. According to some embodiments, the two or more struts are located in a flow-diverting portion of the existing stent. According to some embodiments the one, two, or more struts are not within a flow diverting segment of the stent. According to some embodiments, the hydrogel is applied to an inner wall of the strut or multiple struts. According to some embodiments, the hydrogel is applied to an outer wall of the strut. According to some embodiments, the hydrogel is applied to the intervening surfaces of the strut(s) (the surfaces facing the other struts). According to some embodiments, the hydrogel expands upon exposure to blood. According to some embodiments, the hydrogel applied to one strut expands in vivo to contact the hydrogel applied to adjacent struts. According to some embodiments, the hydrogel expands upon exposure to blood to cover at least 5% to at least 100% of the length of the existing stent. According to some embodiments, the hydrogel is non-permeable. According to some embodiments, the hydrogel is selectively-permeable. According to some embodiments when the hydrogel expands there may flow across the stent can be reduced by as little as 5% to as much as 100%. According to some embodiments, the flow-diverting portion of the existing stent is about 1% to about 100% the length of the existing stent. According to some embodiments, the flow-diverting portion of the existing stent is located at the proximal end of the existing stent. According to some embodiments, the flow-diverting portion of the existing stent is located at the distal end of the existing stent. According to some embodiments, the flow-diverting portion of the existing stent is located in the center of the existing stent (equidistant from the distal portion and the proximal portion of the stent). According to some embodiments, the existing stent is a laser cut stent. According to some embodiments, the existing stent is weaved stent. According to some embodiments, the existing stent is a balloon-expanding stent. According to some embodiments, the existing stent is a self-expanding stent. According to some embodiments, the existing stent comprises an inner diameter ranging from about 0.1 mm to about 150 mm. According to some embodiments, the existing stent comprises a length from about 1 mm to about 800 mm. According to some embodiments, the existing stent is connected to a wire. According to some embodiments, the wire is connected to the proximal end of the existing stent. According to some embodiments, the wire is connected to the distal end of the existing stent. According to some embodiments, the wire is detachable. According to some embodiments, the wire is mechanically detachable. According to some embodiments, the existing stent connects to a single, mechanically-detachable site on the wire. According to some embodiments, the wire is electrolytically detachable. According to some embodiments, the existing stent connects to a single, electrolytically-detachable site on the wire. According to some embodiments, the wire is hydrostatically detachable. According to some embodiments, the existing stent connects to a single, hydrostatically-detachable site on the wire. According to some embodiments, the existing stent is retrieved from a blood vessel. According to some embodiments, the existing stent is retrievable when about 0% to about 100% of the stent is deployed. According to some embodiments, the existing stent is re-positioned in a blood vessel. According to some embodiments, the existing stent can be re-positioned when about 0% to about 100% of the stent is deployed. According to some embodiments, the existing stent can be re-sheathed in a blood vessel. According to some embodiments, the existing stent can be re-sheathed up to the flow-diverting portion of the stent. According to some embodiments, the existing stent can be re-sheathed when about 0% to about 100% of the stent is deployed. According to some embodiments, the existing stent is tapered. According to some embodiments, the existing stent is tapered at a proximal end. According to some embodiments, the existing stent is tapered at a distal end. According to some embodiments, the existing stent is flared. According to some embodiments, the existing stent is flared at a proximal end. According to some embodiments, the existing stent is flared at a distal end.

According to some embodiments, the stent comprises a non-anchor portion and an anchor portion. According to some embodiments, the anchor portion is located at a distal end, at a proximal end or at both ends of the stent. According to some embodiments, the anchor portion is located at multiple intervals along the length (l) of the stent. According to the some embodiments, the anchor portion comprises interstices. According to some embodiments, the interstices of the anchor portion and/or the portion adjacent to the anchor portion of the stent are larger than the interstices of the non-anchor portion of the stent. According to some embodiments, the larger interstices of the anchor portion and/or the portion adjacent to the anchor portion of the stent may reduce the risk of occlusion of critical small blood vessel branches. Such blood vessel branches include, but are not limited to, basilar artery perforators, anterior cerebral artery (ACA) lenticulostriates and middle cerebral artery (MCA) lenticulostriates. According to some embodiments, the interstices of the anchor portion of the stent may reduce the risk of occlusion of blood vessel side branches. Such side-branches include, but are not limited to, the ophthalmic artery.

According to some embodiments, the endovascular stent of the described invention is self-expanding. Self-expanding stents are manufactured at or slightly above blood vessel diameter and are crimped and constrained to a smaller diameter until the intended delivery site of the stent is reached. Once the intended delivery site is reached, the constraint is removed and the stent is deployed. A non-limiting example of a constraint is a sheath. Sheaths include, but are not limited to, a catheter.

According to some embodiments, the endovascular stent of the described invention is balloon-expanding. Balloon-expanding stents are manufactured in a crimped state and are expanded to blood vessel diameter by inflating a balloon. The inflated balloon plastically deforms (i.e., expands) the stent.

According to some embodiments, the balloon is comprised of various shapes including, but not limited to, a cylinder, a sphere, an oval, a cone, a step, a taper and a dog bone.

According to some embodiments, the balloon is comprised of a material such as, for example, a polyamide, a polyethylene terephthalate (PET), a polyurethane, a composite, and an engineered nylons. Exemplary engineered nylons include, but are not limited to, Pebax®, Grilamid®, and Vestamid®.

According to some embodiments, the balloon ends are comprised of various shapes including, but not limited to, a conical sharp corner, a conical radius corner, an offset neck, a spherical end and a square.

According to some embodiments, the balloon is filled with a fluid. Non-limiting examples of fluid include sterile water, saline and contrast medium. Non-limiting examples of contrast medium include barium-containing medium and iodine-containing medium.

According to some embodiments, the endovascular stent of the described invention comprises a radiopaque marker at the distal end of the endovascular stent. According to some embodiments, the stent comprises a radiopaque marker at the proximal end. According to some embodiments, the stent comprises a radiopaque marker at both the distal and proximal ends of the stent. According to some embodiments, the stent of the described invention comprises a radiopaque marker at the distal end of the covered portion of the stent. According to some embodiments, the stent comprises a radiopaque marker at the proximal end of the covered portion stent. According to some embodiments, the stent comprises a radiopaque marker at both the distal and proximal ends of the covered portion of the stent. According to some embodiments, the stent comprises a radiopaque marker at the distal end of the flow-diverting portion of the stent. According to some embodiments, the stent comprises a radiopaque marker at the proximal end of the flow-diverting portion of the stent. According to some embodiments, the stent comprises a radiopaque marker at both the distal and proximal ends of the flow-diverting portion of the stent. According to some embodiments, the stent of the described invention comprises a radiopaque marker at the distal end of the covered portion and at the distal end of the flow-diverting portion of the stent. According to some embodiments, the stent comprises a radiopaque marker at the proximal end of the covered portion and at the proximal end of the flow-diverting portion of the stent. According to some embodiments, the stent comprises a radiopaque marker at both the distal and proximal ends of the covered portion and the flow-diverting portion of the stent. According to some embodiments, the stent comprises multiple radiopaque markers along its length (l) and throughout its circumference. Non-limiting examples of radiopaque markers include platinum, gold, barium sulfate, bismuth oxychloride, tantalum and the like.

According to some embodiments, the endovascular stent of the described invention is retrieved from a blood vessel. According to some embodiments, the stent is retrievable when about 0% to about 100% of the stent is deployed. According to some embodiments, the stent is retrievable when about 0% of the stent is deployed. According to some embodiments, the stent is retrievable when about 1% of the stent is deployed. According to some embodiments, the stent is retrievable when about 2% of the stent is deployed. According to some embodiments, the stent is retrievable when about 3% of the stent is deployed. According to some embodiments, the stent is retrievable when about 4% of the stent is deployed. According to some embodiments, the stent is retrievable when about 5% of the stent is deployed. According to some embodiments, the stent is retrievable when about 6% of the stent is deployed. According to some embodiments, the stent is retrievable when about 7% of the stent is deployed. According to some embodiments, the stent is retrievable when about 8% of the stent is deployed. According to some embodiments, the stent is retrievable when about 9% of the stent is deployed. According to some embodiments, the stent is retrievable when about 10% of the stent is deployed. According to some embodiments, the stent is retrievable when about 11% of the stent is deployed. According to some embodiments, the stent is retrievable when about 12% of the stent is deployed. According to some embodiments, the stent is retrievable when about 13% of the stent is deployed. According to some embodiments, the stent is retrievable when about 14% of the stent is deployed. According to some embodiments, the stent is retrievable when about 15% of the stent is deployed. According to some embodiments, the stent is retrievable when about 16% of the stent is deployed. According to some embodiments, the stent is retrievable when about 17% of the stent is deployed. According to some embodiments, the stent is retrievable when about 18% of the stent is deployed. According to some embodiments, the stent is retrievable when about 19% of the stent is deployed. According to some embodiments, the stent is retrievable when about 20% of the stent is deployed. According to some embodiments, the stent is retrievable when about 21% of the stent is deployed. According to some embodiments, the stent is retrievable when about 22% of the stent is deployed. According to some embodiments, the stent is retrievable when about 23% of the stent is deployed. According to some embodiments, the stent is retrievable when about 24% of the stent is deployed. According to some embodiments, the stent is retrievable when about 25% of the stent is deployed. According to some embodiments, the stent is retrievable when about 26% of the stent is deployed. According to some embodiments, the stent is retrievable when about 27% of the stent is deployed. According to some embodiments, the stent is retrievable when about 28% of the stent is deployed. According to some embodiments, the stent is retrievable when about 29% of the stent is deployed. According to some embodiments, the stent is retrievable when about 30% of the stent is deployed. According to some embodiments, the stent is retrievable when about 31% of the stent is deployed. According to some embodiments, the stent is retrievable when about 32% of the stent is deployed. According to some embodiments, the stent is retrievable when about 33% of the stent is deployed. According to some embodiments, the stent is retrievable when about 34% of the stent is deployed. According to some embodiments, the stent is retrievable when about 35% of the stent is deployed. According to some embodiments, the stent is retrievable when about 36% of the stent is deployed. According to some embodiments, the stent is retrievable when about 37% of the stent is deployed. According to some embodiments, the stent is retrievable when about 38% of the stent is deployed. According to some embodiments, the stent is retrievable when about 39% of the stent is deployed. According to some embodiments, the stent is retrievable when about 40% of the stent is deployed. According to some embodiments, the stent is retrievable when about 41% of the stent is deployed. According to some embodiments, the stent is retrievable when about 42% of the stent is deployed. According to some embodiments, the stent is retrievable when about 43% of the stent is deployed. According to some embodiments, the stent is retrievable when about 44% of the stent is deployed. According to some embodiments, the stent is retrievable when about 45% of the stent is deployed. According to some embodiments, the stent is retrievable when about 46% of the stent is deployed. According to some embodiments, the stent is retrievable when about 47% of the stent is deployed. According to some embodiments, the stent is retrievable when about 48% of the stent is deployed. According to some embodiments, the stent is retrievable when about 49% of the stent is deployed. According to some embodiments, the stent is retrievable when about 50% of the stent is deployed. According to some embodiments, the stent is retrievable when about 51% of the stent is deployed. According to some embodiments, the stent is retrievable when about 52% of the stent is deployed. According to some embodiments, the stent is retrievable when about 53% of the stent is deployed. According to some embodiments, the stent is retrievable when about 54% of the stent is deployed. According to some embodiments, the stent is retrievable when about 55% of the stent is deployed. According to some embodiments, the stent is retrievable when about 56% of the stent is deployed. According to some embodiments, the stent is retrievable when about 57% of the stent is deployed. According to some embodiments, the stent is retrievable when about 58% of the stent is deployed. According to some embodiments, the stent is retrievable when about 59% of the stent is deployed. According to some embodiments, the stent is retrievable when about 60% of the stent is deployed. According to some embodiments, the stent is retrievable when about 61% of the stent is deployed. According to some embodiments, the stent is retrievable when about 62% of the stent is deployed. According to some embodiments, the stent is retrievable when about 63% of the stent is deployed. According to some embodiments, the stent is retrievable when about 64% of the stent is deployed. According to some embodiments, the stent is retrievable when about 65% of the stent is deployed. According to some embodiments, the stent is retrievable when about 66% of the stent is deployed. According to some embodiments, the stent is retrievable when about 67% of the stent is deployed. According to some embodiments, the stent is retrievable when about 68% of the stent is deployed. According to some embodiments, the stent is retrievable when about 69% of the stent is deployed. According to some embodiments, the stent is retrievable when about 70% of the stent is deployed. According to some embodiments, the stent is retrievable when about 71% of the stent is deployed. According to some embodiments, the stent is retrievable when about 72% of the stent is deployed. According to some embodiments, the stent is retrievable when about 73% of the stent is deployed. According to some embodiments, the stent is retrievable when about 74% of the stent is deployed. According to some embodiments, the stent is retrievable when about 75% of the stent is deployed. According to some embodiments, the stent is retrievable when about 76% of the stent is deployed. According to some embodiments, the stent is retrievable when about 77% of the stent is deployed. According to some embodiments, the stent is retrievable when about 78% of the stent is deployed. According to some embodiments, the stent is retrievable when about 79% of the stent is deployed. According to some embodiments, the stent is retrievable when about 80% of the stent is deployed. According to some embodiments, the stent is retrievable when about 81% of the stent is deployed. According to some embodiments, the stent is retrievable when about 82% of the stent is deployed. According to some embodiments, the stent is retrievable when about 83% of the stent is deployed. According to some embodiments, the stent is retrievable when about 84% of the stent is deployed. According to some embodiments, the stent is retrievable when about 85% of the stent is deployed. According to some embodiments, the stent is retrievable when about 86% of the stent is deployed. According to some embodiments, the stent is retrievable when about 87% of the stent is deployed. According to some embodiments, the stent is retrievable when about 88% of the stent is deployed. According to some embodiments, the stent is retrievable when about 89% of the stent is deployed. According to some embodiments, the stent is retrievable when about 90% of the stent is deployed. According to some embodiments, the stent is retrievable when about 91% of the stent is deployed. According to some embodiments, the stent is retrievable when about 92% of the stent is deployed. According to some embodiments, the stent is retrievable when about 93% of the stent is deployed. According to some embodiments, the stent is retrievable when about 94% of the stent is deployed. According to some embodiments, the stent is retrievable when about 95% of the stent is deployed. According to some embodiments, the stent is retrievable when about 96% of the stent is deployed. According to some embodiments, the stent is retrievable when about 97% of the stent is deployed. According to some embodiments, the stent is retrievable when about 98% of the stent is deployed. According to some embodiments, the stent is retrievable when about 99% of the stent is deployed. According to some embodiments, the stent is retrievable when about 100% of the stent is deployed.

According to some embodiments, the endovascular stent of the described invention is re-positioned in a blood vessel. According to some embodiments, the stent can be re-positioned when about 0% to about 100% of the stent is deployed. According to some embodiments, the stent can be re-positioned when about 0% of the stent is deployed. According to some embodiments, the stent can be re-positioned when about 1% of the stent is deployed. According to some embodiments, the stent can be re-positioned when about 2% of the stent is deployed. According to some embodiments, the stent can be re-positioned when about 3% of the stent is deployed. According to some embodiments, the stent can be re-positioned when about 4% of the stent is deployed. According to some embodiments, the stent can be re-positioned when about 5% of the stent is deployed. According to some embodiments, the stent can be re-positioned when about 6% of the stent is deployed. According to some embodiments, the stent can be re-positioned when about 7% of the stent is deployed. According to some embodiments, the stent can be re-positioned when about 8% of the stent is deployed. According to some embodiments, the stent can be re-positioned when about 9% of the stent is deployed. According to some embodiments, the stent can be re-positioned when about 10% of the stent is deployed. According to some embodiments, the stent can be re-positioned when about 11% of the stent is deployed. According to some embodiments, the stent can be re-positioned when about 12% of the stent is deployed. According to some embodiments, the stent can be re-positioned when about 13% of the stent is deployed. According to some embodiments, the stent can be re-positioned when about 14% of the stent is deployed. According to some embodiments, the stent can be re-positioned when about 15% of the stent is deployed. According to some embodiments, the stent can be re-positioned when about 16% of the stent is deployed. According to some embodiments, the stent can be re-positioned when about 17% of the stent is deployed. According to some embodiments, the stent can be re-positioned when about 18% of the stent is deployed. According to some embodiments, the stent can be re-positioned when about 19% of the stent is deployed. According to some embodiments, the stent can be re-positioned when about 20% of the stent is deployed. According to some embodiments, the stent can be re-positioned when about 21% of the stent is deployed. According to some embodiments, the stent can be re-positioned when about 22% of the stent is deployed. According to some embodiments, the stent can be re-positioned when about 23% of the stent is deployed. According to some embodiments, the stent can be re-positioned when about 24% of the stent is deployed. According to some embodiments, the stent can be re-positioned when about 25% of the stent is deployed. According to some embodiments, the stent can be re-positioned when about 26% of the stent is deployed. According to some embodiments, the stent can be re-positioned when about 27% of the stent is deployed. According to some embodiments, the stent can be re-positioned when about 28% of the stent is deployed. According to some embodiments, the stent can be re-positioned when about 29% of the stent is deployed. According to some embodiments, the stent can be re-positioned when about 30% of the stent is deployed. According to some embodiments, the stent can be re-positioned when about 31% of the stent is deployed. According to some embodiments, the stent can be re-positioned when about 32% of the stent is deployed. According to some embodiments, the stent can be re-positioned when about 33% of the stent is deployed. According to some embodiments, the stent can be re-positioned when about 34% of the stent is deployed. According to some embodiments, the stent can be re-positioned when about 35% of the stent is deployed. According to some embodiments, the stent can be re-positioned when about 36% of the stent is deployed. According to some embodiments, the stent can be re-positioned when about 37% of the stent is deployed. According to some embodiments, the stent can be re-positioned when about 38% of the stent is deployed. According to some embodiments, the stent can be re-positioned when about 39% of the stent is deployed. According to some embodiments, the stent can be re-positioned when about 40% of the stent is deployed. According to some embodiments, the stent can be re-positioned when about 41% of the stent is deployed. According to some embodiments, the stent can be re-positioned when about 42% of the stent is deployed. According to some embodiments, the stent can be re-positioned when about 43% of the stent is deployed. According to some embodiments, the stent can be re-positioned when about 44% of the stent is deployed. According to some embodiments, the stent can be re-positioned when about 45% of the stent is deployed. According to some embodiments, the stent can be re-positioned when about 46% of the stent is deployed. According to some embodiments, the stent can be re-positioned when about 47% of the stent is deployed. According to some embodiments, the stent can be re-positioned when about 48% of the stent is deployed. According to some embodiments, the stent can be re-positioned when about 49% of the stent is deployed. According to some embodiments, the stent can be re-positioned when about 50% of the stent is deployed. According to some embodiments, the stent can be re-positioned when about 51% of the stent is deployed. According to some embodiments, the stent can be re-positioned when about 52% of the stent is deployed. According to some embodiments, the stent can be re-positioned when about 53% of the stent is deployed. According to some embodiments, the stent can be re-positioned when about 54% of the stent is deployed. According to some embodiments, the stent can be re-positioned when about 55% of the stent is deployed. According to some embodiments, the stent can be re-positioned when about 56% of the stent is deployed. According to some embodiments, the stent can be re-positioned when about 57% of the stent is deployed. According to some embodiments, the stent can be re-positioned when about 58% of the stent is deployed. According to some embodiments, the stent can be re-positioned when about 59% of the stent is deployed. According to some embodiments, the stent can be re-positioned when about 60% of the stent is deployed. According to some embodiments, the stent can be re-positioned when about 61% of the stent is deployed. According to some embodiments, the stent can be re-positioned when about 62% of the stent is deployed. According to some embodiments, the stent can be re-positioned when about 63% of the stent is deployed. According to some embodiments, the stent can be re-positioned when about 64% of the stent is deployed. According to some embodiments, the stent can be re-positioned when about 65% of the stent is deployed. According to some embodiments, the stent can be re-positioned when about 66% of the stent is deployed. According to some embodiments, the stent can be re-positioned when about 67% of the stent is deployed. According to some embodiments, the stent can be re-positioned when about 68% of the stent is deployed. According to some embodiments, the stent can be re-positioned when about 69% of the stent is deployed. According to some embodiments, the stent can be re-positioned when about 70% of the stent is deployed. According to some embodiments, the stent can be re-positioned when about 71% of the stent is deployed. According to some embodiments, the stent can be re-positioned when about 72% of the stent is deployed. According to some embodiments, the stent can be re-positioned when about 73% of the stent is deployed. According to some embodiments, the stent can be re-positioned when about 74% of the stent is deployed. According to some embodiments, the stent can be re-positioned when about 75% of the stent is deployed. According to some embodiments, the stent can be re-positioned when about 76% of the stent is deployed. According to some embodiments, the stent can be re-positioned when about 77% of the stent is deployed. According to some embodiments, the stent can be re-positioned when about 78% of the stent is deployed. According to some embodiments, the stent can be re-positioned when about 79% of the stent is deployed. According to some embodiments, the stent can be re-positioned when about 80% of the stent is deployed. According to some embodiments, the stent can be re-positioned when about 81% of the stent is deployed. According to some embodiments, the stent can be re-positioned when about 82% of the stent is deployed. According to some embodiments, the stent can be re-positioned when about 83% of the stent is deployed. According to some embodiments, the stent can be re-positioned when about 84% of the stent is deployed. According to some embodiments, the stent can be re-positioned when about 85% of the stent is deployed. According to some embodiments, the stent can be re-positioned when about 86% of the stent is deployed. According to some embodiments, the stent can be re-positioned when about 87% of the stent is deployed. According to some embodiments, the stent can be re-positioned when about 88% of the stent is deployed. According to some embodiments, the stent can be re-positioned when about 89% of the stent is deployed. According to some embodiments, the stent can be re-positioned when about 90% of the stent is deployed. According to some embodiments, the stent can be re-positioned when about 91% of the stent is deployed. According to some embodiments, the stent can be re-positioned when about 92% of the stent is deployed. According to some embodiments, the stent can be re-positioned when about 93% of the stent is deployed. According to some embodiments, the stent can be re-positioned when about 94% of the stent is deployed. According to some embodiments, the stent can be re-positioned when about 95% of the stent is deployed. According to some embodiments, the stent can be re-positioned when about 96% of the stent is deployed. According to some embodiments, the stent can be re-positioned when about 97% of the stent is deployed. According to some embodiments, the stent can be re-positioned when about 98% of the stent is deployed. According to some embodiments, the stent can be re-positioned when about 99% of the stent is deployed. According to some embodiments, the stent can be re-positioned when about 100% of the stent is deployed.

According to some embodiments, the endovascular stent of the described invention can be re-sheathed in a blood vessel. According to some embodiments, the stent of the described invention can be re-sheathed up to the flow-diverting portion of the stent. According to some embodiments, the stent can be re-sheathed when about 0% to about 100% of the stent is deployed. According to some embodiments, the stent can be re-sheathed when about 0% of the stent is deployed. According to some embodiments, the stent can be re-sheathed when about 1% of the stent is deployed. According to some embodiments, the stent can be re-sheathed when about 2% of the stent is deployed. According to some embodiments, the stent can be re-sheathed when about 3% of the stent is deployed. According to some embodiments, the stent can be re-sheathed when about 4% of the stent is deployed. According to some embodiments, the stent can be re-sheathed when about 5% of the stent is deployed. According to some embodiments, the stent can be re-sheathed when about 6% of the stent is deployed. According to some embodiments, the stent can be re-sheathed when about 7% of the stent is deployed. According to some embodiments, the stent can be re-sheathed when about 8% of the stent is deployed. According to some embodiments, the stent can be re-sheathed when about 9% of the stent is deployed. According to some embodiments, the stent can be re-sheathed when about 10% of the stent is deployed. According to some embodiments, the stent can be re-sheathed when about 11% of the stent is deployed. According to some embodiments, the stent can be re-sheathed when about 12% of the stent is deployed. According to some embodiments, the stent can be re-sheathed when about 13% of the stent is deployed. According to some embodiments, the stent can be re-sheathed when about 14% of the stent is deployed. According to some embodiments, the stent can be re-sheathed when about 15% of the stent is deployed. According to some embodiments, the stent can be re-sheathed when about 16% of the stent is deployed. According to some embodiments, the stent can be re-sheathed when about 17% of the stent is deployed. According to some embodiments, the stent can be re-sheathed when about 18% of the stent is deployed. According to some embodiments, the stent can be re-sheathed when about 19% of the stent is deployed. According to some embodiments, the stent can be re-sheathed when about 20% of the stent is deployed. According to some embodiments, the stent can be re-sheathed when about 21% of the stent is deployed. According to some embodiments, the stent can be re-sheathed when about 22% of the stent is deployed. According to some embodiments, the stent can be re-sheathed when about 23% of the stent is deployed. According to some embodiments, the stent can be re-sheathed when about 24% of the stent is deployed. According to some embodiments, the stent can be re-sheathed when about 25% of the stent is deployed. According to some embodiments, the stent can be re-sheathed when about 26% of the stent is deployed. According to some embodiments, the stent can be re-sheathed when about 27% of the stent is deployed. According to some embodiments, the stent can be re-sheathed when about 28% of the stent is deployed. According to some embodiments, the stent can be re-sheathed when about 29% of the stent is deployed. According to some embodiments, the stent can be re-sheathed when about 30% of the stent is deployed. According to some embodiments, the stent can be re-sheathed when about 31% of the stent is deployed. According to some embodiments, the stent can be re-sheathed when about 32% of the stent is deployed. According to some embodiments, the stent can be re-sheathed when about 33% of the stent is deployed. According to some embodiments, the stent can be re-sheathed when about 34% of the stent is deployed. According to some embodiments, the stent can be re-sheathed when about 35% of the stent is deployed. According to some embodiments, the stent can be re-sheathed when about 36% of the stent is deployed. According to some embodiments, the stent can be re-sheathed when about 37% of the stent is deployed. According to some embodiments, the stent can be re-sheathed when about 38% of the stent is deployed. According to some embodiments, the stent can be re-sheathed when about 39% of the stent is deployed. According to some embodiments, the stent can be re-sheathed when about 40% of the stent is deployed. According to some embodiments, the stent can be re-sheathed when about 41% of the stent is deployed. According to some embodiments, the stent can be re-sheathed when about 42% of the stent is deployed. According to some embodiments, the stent can be re-sheathed when about 43% of the stent is deployed. According to some embodiments, the stent can be re-sheathed when about 44% of the stent is deployed. According to some embodiments, the stent can be re-sheathed when about 45% of the stent is deployed. According to some embodiments, the stent can be re-sheathed when about 46% of the stent is deployed. According to some embodiments, the stent can be re-sheathed when about 47% of the stent is deployed. According to some embodiments, the stent can be re-sheathed when about 48% of the stent is deployed. According to some embodiments, the stent can be re-sheathed when about 49% of the stent is deployed. According to some embodiments, the stent can be re-sheathed when about 50% of the stent is deployed. According to some embodiments, the stent can be re-sheathed when about 51% of the stent is deployed. According to some embodiments, the stent can be re-sheathed when about 52% of the stent is deployed. According to some embodiments, the stent can be re-sheathed when about 53% of the stent is deployed. According to some embodiments, the stent can be re-sheathed when about 54% of the stent is deployed. According to some embodiments, the stent can be re-sheathed when about 55% of the stent is deployed. According to some embodiments, the stent can be re-sheathed when about 56% of the stent is deployed. According to some embodiments, the stent can be re-sheathed when about 57% of the stent is deployed. According to some embodiments, the stent can be re-sheathed when about 58% of the stent is deployed. According to some embodiments, the stent can be re-sheathed when about 59% of the stent is deployed. According to some embodiments, the stent can be re-sheathed when about 60% of the stent is deployed. According to some embodiments, the stent can be re-sheathed when about 61% of the stent is deployed. According to some embodiments, the stent can be re-sheathed when about 62% of the stent is deployed. According to some embodiments, the stent can be re-sheathed when about 63% of the stent is deployed. According to some embodiments, the stent can be re-sheathed when about 64% of the stent is deployed. According to some embodiments, the stent can be re-sheathed when about 65% of the stent is deployed. According to some embodiments, the stent can be re-sheathed when about 66% of the stent is deployed. According to some embodiments, the stent can be re-sheathed when about 67% of the stent is deployed. According to some embodiments, the stent can be re-sheathed when about 68% of the stent is deployed. According to some embodiments, the stent can be re-sheathed when about 69% of the stent is deployed. According to some embodiments, the stent can be re-sheathed when about 70% of the stent is deployed. According to some embodiments, the stent can be re-sheathed when about 71% of the stent is deployed. According to some embodiments, the stent can be re-sheathed when about 72% of the stent is deployed. According to some embodiments, the stent can be re-sheathed when about 73% of the stent is deployed. According to some embodiments, the stent can be re-sheathed when about 74% of the stent is deployed. According to some embodiments, the stent can be re-sheathed when about 75% of the stent is deployed.

According to some embodiments, the stent can be re-sheathed when about 76% of the stent is deployed. According to some embodiments, the stent can be re-sheathed when about 77% of the stent is deployed. According to some embodiments, the stent can be re-sheathed when about 78% of the stent is deployed. According to some embodiments, the stent can be re-sheathed when about 79% of the stent is deployed. According to some embodiments, the stent can be re-sheathed when about 80% of the stent is deployed. According to some embodiments, the stent can be re-sheathed when about 81% of the stent is deployed. According to some embodiments, the stent can be re-sheathed when about 82% of the stent is deployed. According to some embodiments, the stent can be re-sheathed when about 83% of the stent is deployed. According to some embodiments, the stent can be re-sheathed when about 84% of the stent is deployed. According to some embodiments, the stent can be re-sheathed when about 85% of the stent is deployed. According to some embodiments, the stent can be re-sheathed when about 86% of the stent is deployed. According to some embodiments, the stent can be re-sheathed when about 87% of the stent is deployed. According to some embodiments, the stent can be re-sheathed when about 88% of the stent is deployed. According to some embodiments, the stent can be re-sheathed when about 89% of the stent is deployed. According to some embodiments, the stent can be re-sheathed when about 90% of the stent is deployed. According to some embodiments, the stent can be re-sheathed when about 91% of the stent is deployed. According to some embodiments, the stent can be re-sheathed when about 92% of the stent is deployed. According to some embodiments, the stent can be re-sheathed when about 93% of the stent is deployed. According to some embodiments, the stent can be re-sheathed when about 94% of the stent is deployed. According to some embodiments, the stent can be re-sheathed when about 95% of the stent is deployed. According to some embodiments, the stent can be re-sheathed when about 96% of the stent is deployed. According to some embodiments, the stent can be re-sheathed when about 97% of the stent is deployed. According to some embodiments, the stent can be re-sheathed when about 98% of the stent is deployed. According to some embodiments, the stent can be re-sheathed when about 99% of the stent is deployed. According to some embodiments, the stent can be re-sheathed when about 100% of the stent is deployed.

According to some embodiments, the endovascular stent of the described invention is tapered. According to some embodiments, the stent is tapered at a proximal end. According to some embodiments, the stent is tapered at a distal end. According to some embodiments, the stent is tapered at a site along the length (l) of the stent. According to some embodiments, the stent is tapered at a single site along the length (l) of the stent. According to some embodiments, the stent is tapered at multiple sites along the length (l) of the stent. According to some embodiments, the stent is widened and/or flared at one or multiple segments, anywhere along its length.

According to some embodiments, the endovascular stent of the described invention is a laser-cut stent. According to some embodiments, the endovascular stent of the described invention is a weave stent. According to some embodiments, the endovascular stent of the described invention is a combination weave stent and laser-cut stent. According to some embodiments, the endovascular stent of the described invention is a laser-cut stent at a proximal end, a weave stent, and a laser-cut stent at a distal end. According to some embodiments, the endovascular stent of the described invention is a laser-cut stent at a proximal end, a laser-cut stent at a distal end, and a weave stent in the center (equidistant from the distal end and the proximal end of the stent). According to some embodiments, a weave stent is connected to the outside or to the inside of a segment of another stent. According to some embodiments, the weave stent is connected to a segment of another stent by a weld. According to some embodiments, the weave stent is connected to a segment of another stent by a suture. According to some embodiments, the weave stent is connected to a segment of another weave stent. According to some embodiments, the weave stent is connected to a segment of a laser-cut stent. According to some embodiments, the weave stent is a flow-diverting stent. According to some embodiments, the combination weave stent and laser-cut stent is a balloon-expanding stent. According to some embodiments, the combination weave stent and laser-cut stent is a self-expanding stent. According to some embodiments, the combination weave stent and laser-cut stent is connected to a wire. According to some embodiments, the wire is connected to the proximal end of the combination weave stent and laser-cut stent. According to some embodiments, the wire is connected to the distal end of the combination weave stent and laser-cut stent. According to some embodiments, the combination weave stent and laser-cut stent is connected to a single site on the wire. According to some embodiments, multiple sites on the combination weave stent and laser-cut stent connect to a single site on the wire. According to some embodiments, multiple sites on the combination weave stent and laser-cut stent connect to multiple sites on the wire. According to some embodiments, the wire is detachable. According to some embodiments, the wire is mechanically detachable. According to some embodiments, the combination weave stent and laser-cut stent connects to a single, mechanically-detachable site on the wire. According to some embodiments, the wire is electrolytically detachable. According to some embodiments, the combination weave stent and laser-cut stent connects to a single, electrolytically-detachable site on the wire. According to some embodiments, the wire is hydrostatically detachable. According to some embodiments, the combination weave stent and laser-cut stent connects to a single, hydrostatically-detachable site on the wire.

According to some embodiments, the combination weave stent and laser-cut stent can be retrieved from a blood vessel. According to some embodiments, the combination weave stent and laser-cut stent is retrievable when about 0% to about 100% of the stent is deployed. According to some embodiments, the combination weave stent and laser-cut stent is re-positioned in a blood vessel. According to some embodiments, the combination weave stent and laser-cut stent can be re-positioned when about 0% to about 100% of the stent is deployed. According to some embodiments, the combination weave stent and laser-cut stent can be re-sheathed in a blood vessel. According to some embodiments, the combination weave stent and laser-cut stent can be re-sheathed up to the flow-diverting portion of the stent. According to some embodiments, the combination weave stent and laser-cut stent can be re-sheathed when about 0% to about 100% of the combination weave stent and laser-cut stent is deployed. According to some embodiments, the combination weave stent and laser-cut stent is tapered. According to some embodiments, the combination weave stent and laser-cut stent is tapered at a proximal end. According to some embodiments, the combination weave stent and laser-cut stent is tapered at a distal end. According to some embodiments, the combination weave stent and laser-cut stent is tapered at a site along the length of the combination weave stent and laser-cut stent. According to some embodiments, the combination weave stent and laser-cut stent is tapered at a single site along the length of the combination weave stent and laser-cut stent. According to some embodiments, the combination weave stent and laser-cut stent is tapered at multiple sites along the length of the combination weave stent and laser-cut stent. According to some embodiments, the combination weave stent and laser-cut stent is flared. According to some embodiments, the combination weave stent and laser-cut stent is flared at a proximal end. According to some embodiments, the combination weave stent and laser-cut stent is flared at a distal end. According to some embodiments, the combination weave stent and laser-cut stent is flared at a site along the length of the combination weave stent and laser-cut stent. According to some embodiments, the combination weave stent and laser-cut stent is flared at a single site along the length of the combination weave stent and laser-cut stent. According to some embodiments, the combination weave stent and laser-cut stent is flared at multiple sites along the length of the combination weave stent and laser-cut stent.

According to some embodiments, the described invention, when used in an endovascular procedure, is effective to divert blood flow away from an aneurysm. According to some embodiments, the described invention, when used in an endovascular procedure, is effective to divert blood flow away from an aneurysm, while allowing blood to flow to healthy adjacent side branching arteries. Exemplary side branching arteries include, but are not limited to, the middle cerebral artery (MCA) and the anterior cerebral artery (ACA). According to some embodiments, the described invention, when used in an endovascular procedure, is effective to divert blood flow away from a cavernous carotid aneurysm. According to some embodiments, the described invention, when used in an endovascular procedure, is effective to divert blood flow away from a cavernous carotid fistula. According to some embodiments, the described invention, when used in an endovascular procedure, is effective to blood flow away from a dissecting vertebral artery aneurysm. According to some embodiments, the described invention, when used in an endovascular procedure, is effective to divert blood flow away from an aneurysm that has ruptured during surgical treatment, endovascular treatment or both.

According to some embodiments, the described invention, when used in an endovascular procedure, is effective to occlude an aneurysm. According to some embodiments, the described invention, when used in an endovascular procedure, is effective to occlude an aneurysm while not occluding healthy adjacent side branching arteries. Exemplary side branching arteries include, but are not limited to, the middle cerebral artery (MCA) and the anterior cerebral artery (ACA). According to some embodiments, the described invention, when used in an endovascular procedure, is effective to occlude a cavernous carotid aneurysm. According to some embodiments, the described invention, when used in an endovascular procedure, is effective to occlude a cavernous carotid fistula. According to some embodiments, the described invention, when used in an endovascular procedure, is effective to occlude a dissecting vertebral artery aneurysm. According to some embodiments, the described invention, when used in an endovascular procedure, is effective to occlude an aneurysm at risk of rupture during surgical treatment, endovascular treatment or both.

According to some embodiments, the described invention provides two or more stents with overlapping flow-diverting portions, that when used in an endovascular procedure, are effective to divert blood flow away from an aneurysm. According to some embodiments, the described invention provides two or more stents with overlapping flow-diverting and/or covered portions, that when used in an endovascular procedure, are effective to divert blood flow away from an aneurysm while allowing blood to flow to healthy adjacent side branching arteries. Exemplary side branching arteries include, but are not limited to, the middle cerebral artery (MCA) and the anterior cerebral artery (ACA). According to some embodiments, the described invention provides two or more stents with overlapping flow-diverting portions, that when used in an endovascular procedure, are effective to divert blood flow away from a cavernous carotid aneurysm. According to some embodiments, the described invention provides two or more stents with overlapping flow-diverting portions, that when used in an endovascular procedure, are effective to divert blood flow away from a cavernous carotid fistula. According to some embodiments, the described invention provides two or more stents with overlapping flow-diverting portions, that when used in an endovascular procedure, are effective to divert blood flow away from a dissecting vertebral artery aneurysm. According to some embodiments, the described invention provides two or more stents with overlapping flow-diverting portions, that when used in an endovascular procedure, are effective to divert blood flow away from an aneurysm at risk of rupture during surgical treatment. Without being bound by theory, the two or more stents with overlapping flow-diverting and/or covered portions may be easier to maneuver through a blood vessel and to deliver to their intended target than a single, larger device with more mass.

According to some embodiments, the described invention provides two or more stents with overlapping flow-diverting portions, that when used in an endovascular procedure, are effective to occlude an aneurysm. According to some embodiments, the described invention provides two or more stents with overlapping flow-diverting portions, that when used in an endovascular procedure, are effective to occlude an aneurysm while not occluding healthy adjacent side branching arteries. Exemplary side branching arteries include, but are not limited to, the middle cerebral artery (MCA) and the anterior cerebral artery (ACA). According to some embodiments, the described invention provides two or more stents with overlapping flow-diverting portions, that when used in an endovascular procedure, are effective to occlude a cavernous carotid aneurysm. According to some embodiments, the described invention provides two or more stents with overlapping flow-diverting portions, that when used in an endovascular procedure, are effective to occlude a cavernous carotid fistula. According to some embodiments, the described invention provides two or more stents with overlapping flow-diverting portions, that when used in an endovascular procedure, are effective to occlude a dissecting vertebral artery aneurysm. According to some embodiments, the described invention provides two or more stents with overlapping flow-diverting portions, that when used in an endovascular procedure, are effective to occlude an aneurysm at risk of rupture during surgical treatment.

According to some embodiments, the described invention is effective to cause blood stasis within an aneurysm, thrombus formation within an aneurysm or both.

According to some embodiments, the stent 300 is advanced through the femoral artery, the subclavian artery, radial artery or brachial artery to the arm, or alternatively, any other artery or vein. According to some embodiments, the flow-diverting portion 310 is positioned on an aneurysm neck.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A flow-impeding covered endovascular stent device comprising
    a tubular structure comprising:
        a proximal end and a distal end;
        struts that define small intervening spaces or interstices between the struts; and a hydrogel layer on the struts that define the interstices, wherein the hydrogel layer on one strut is adapted to expand to reach the hydrogel layer applied to adjacent struts and to fill the interstices after implantation;
        a circumference comprising an inner surface and an outer surface; and
        a length (l) from the proximal end to the distal end; and an inner diameter (d);
    wherein,
        the circumference comprises a flow-impeding covering material that is arranged around the circumference:
            on a portion of the length of the inner surface of the circumference,
            on a portion of the length (l) of the outer surface of the circumference; or
            on a portion of the length (l) in a single layer in series with the endovascular device;
        the flow-impeding covering material covers 55-100% of a surface area of the device within the flow-impeding segment, and porosity of the flow-impeding covered segment is from 0% to 45%; and
        the device is adapted to occlude an aneurysm and shut down blood flow, resulting in blood stasis and thrombus formation within an aneurysm or fistula.

2. The flow-impeding covered endovascular stent device according to claim 1, wherein the hydrogel layer comprises a filament woven onto the struts.

3. The flow-impeding covered endovascular stent device according to claim 1, wherein the hydrogel layer is directly adherent to the struts.

4. The flow-impeding covered endovascular stent device according to claim 1, wherein the hydrogel layer is adapted to expand in vivo.

5. The flow-impeding covered endovascular stent device according to claim 4, wherein the hydrogel layer is adapted to expand upon exposure to blood, upon exposure to body temperature, or both.

6. The flow-impeding covered endovascular stent device according to claim 1, wherein the hydrogel layer comprises a synthetic polymer, a natural polymer or a mixed synthetic-natural polymer.

7. The flow-impeding covered endovascular stent device according to claim 1, the hydrogel is a non-biodegradable polymer.

8. The flow-impeding covered endovascular stent device according to claim 7, wherein the hydrogel is a crosslinked acrylamide-sodium acrylate co-polymer.

9. The flow-impeding covered endovascular stent device according to claim 1, wherein the covering flow-impeding material is a polyethylene terephthalate (PET) (Dacron®) or a polyester.

10. The flow-impeding covered endovascular stent device according to claim 9, wherein the covering flow-impeding material comprises an adhered hydrogel on its outer surface that is adapted for expansion to fill any empty spaces between the covering flow-impeding material and the vessel wall and for minimization of a risk of an endoleak after placement of the endovascular device.

11. The flow-impeding covered endovascular stent device according to claim 1, wherein the portion of the length (l) covered by the flow-impeding material is from at least 1% to at least 100% of the endovascular stent device.

12. The flow-impeding covered endovascular stent device according to claim 1, wherein the endovascular stent device comprises a constraint so that a portion of a diameter of the endovascular stent device is smaller than a blood vessel until delivery to the blood vessel, wherein the endovascular device is adapted to self-expand upon removal of the constraint.

13. The flow-impeding covered endovascular stent device according to claim 1, wherein the endovascular stent device comprises a balloon so that a portion of a diameter of the endovascular stent device is smaller than a blood vessel until delivery to the blood vessel, wherein the balloon is adapted to expand the stent to blood vessel diameter after the balloon's inflation.

14. The flow-impeding covered endovascular stent device according to claim 1, wherein the endovascular stent device comprises a constraint and a balloon so that a portion of a diameter of the endovascular stent device is smaller than a blood vessel until delivery to the blood vessel, wherein the balloon is adapted to expand the stent to blood vessel diameter after inflation.

15. The flow-impeding covered endovascular stent device according to claim 1, wherein the endovascular stent device comprises a radiopaque marker for positioning the stent device in the blood vessel.

16. The flow-impeding covered endovascular stent device according to claim 15, wherein the covering flow-impeding material is a polyethylene terephthalate (PET) (Dacron®) or a polyester.

17. The flow-impeding covered endovascular stent device according to claim 16, wherein the covering flow-impeding material comprises an adhered hydrogel on its outer surface that is adapted for expansion to fill any empty spaces between the covering flow-impeding material and the vessel wall and for minimization of a risk of an endoleak after placement of the endovascular device.

18. The flow-impeding endovascular stent device according to claim 16, wherein
   (a) the detachable site on the wire is a mechanically detachable site; or
   (b) the detachable site on the wire is an electrolytically detachable site; or
   (c) the detachable site on the wire is a hydrostatically detachable site.

19. The flow-impeding endovascular stent device according to claim 1, wherein
   (a) the endovascular stent device is adapted for an intracranial blood vessel application; or
   (b) the endovascular stent device is adapted for a peripheral blood vessel application; or
   (c) the endovascular stent device is adapted for a cardiac vessel application.

20. The flow-impeding endovascular stent device according to claim 1, wherein the endovascular stent device is connected to a detachable site on a wire.

21. The flow-impeding endovascular stent device according to claim 1, wherein the device is tapered at the proximal end, at the distal end, or at a site along the length (l) of the device.

22. The flow-impeding endovascular stent device according to claim 1, wherein the device is flared at the proximal end, at the distal end, or at a site along the length (l) of the device.

* * * * *